(12) United States Patent
Van Delft et al.

(10) Patent No.: US 11,168,085 B2
(45) Date of Patent: Nov. 9, 2021

(54) PROCESS FOR THE CYCLOADDITION OF A HETERO(ARYL) 1,3-DIPOLE COMPOUND WITH A (HETERO)CYCLOALKYNE

(71) Applicant: SynAffix B.V., Oss (NL)

(72) Inventors: Floris Louis Van Delft, Nijmegen (NL); Frederik Jan Dommerholt, Beuningen (NL)

(73) Assignee: SYNAFFIX B.V., Oss (NL)

( * ) Notice: Subject to any disclaimer, the term of this patent is extended or adjusted under 35 U.S.C. 154(b) by 0 days.

(21) Appl. No.: 15/113,730

(22) PCT Filed: Jan. 26, 2015

(86) PCT No.: PCT/NL2015/050045
§ 371 (c)(1),
(2) Date: Jul. 22, 2016

(87) PCT Pub. No.: WO2015/112014
PCT Pub. Date: Jul. 30, 2015

(65) Prior Publication Data
US 2017/0002012 A1    Jan. 5, 2017

(30) Foreign Application Priority Data

Jan. 24, 2014 (EP) ..................... 14152420

(51) Int. Cl.

| C07D 487/04 | (2006.01) |
| C07H 19/10 | (2006.01) |
| C07D 225/08 | (2006.01) |
| C07D 225/02 | (2006.01) |
| C07D 231/54 | (2006.01) |
| C07D 261/20 | (2006.01) |
| C07D 249/16 | (2006.01) |
| A61K 47/68 | (2017.01) |
| A61K 47/54 | (2017.01) |
| A61K 47/60 | (2017.01) |
| C07C 269/06 | (2006.01) |
| C07C 271/18 | (2006.01) |
| C07K 14/47 | (2006.01) |

(52) U.S. Cl.
CPC .......... *C07D 487/04* (2013.01); *A61K 47/545* (2017.08); *A61K 47/60* (2017.08); *A61K 47/6855* (2017.08); *C07C 269/06* (2013.01); *C07C 271/18* (2013.01); *C07D 225/02* (2013.01); *C07D 225/08* (2013.01); *C07D 231/54* (2013.01); *C07D 249/16* (2013.01); *C07D 261/20* (2013.01); *C07H 19/10* (2013.01); *C07K 14/473* (2013.01); *C07C 2602/22* (2017.05); *C07C 2603/50* (2017.05)

(58) Field of Classification Search
None
See application file for complete search history.

(56) References Cited

U.S. PATENT DOCUMENTS

| 8,008,252 B2 | 8/2011 | Defrees et al. |
| 2005/0256030 A1 | 11/2005 | Feng |
| 2007/0059275 A1 | 3/2007 | Defrees et al. |
| 2009/0068738 A1 | 3/2009 | Bertozzi et al. |
| 2011/0207147 A1 | 8/2011 | Jewett et al. |
| 2012/0076727 A1 | 3/2012 | McBride et al. |
| 2013/0011901 A1 | 1/2013 | Hosoya et al. |

FOREIGN PATENT DOCUMENTS

| JP | 2005-314382 A | 11/2005 |
| WO | WO-03/031464 A2 | 4/2003 |
| WO | WO-2004/063344 A2 | 7/2004 |
| WO | WO-2005/051249 A1 | 7/2005 |
| WO | WO-2005/063784 A1 | 7/2005 |
| WO | WO-2006/035057 A1 | 4/2006 |
| WO | WO-2006/102717 A1 | 10/2006 |
| WO | WO-2007/081031 A1 | 7/2007 |
| WO | WO-2007/095506 A1 | 8/2007 |
| WO | WO-2007/133855 A2 | 11/2007 |
| WO | WO-2008/029281 A2 | 3/2008 |
| WO | WO-2008/071672 A2 | 6/2008 |
| WO | WO-2009/025645 A1 | 2/2009 |
| WO | WO-2009/067663 A1 | 5/2009 |
| WO | WO-2009/102820 A2 | 8/2009 |
| WO | WO-2010/125065 A2 | 11/2010 |
| WO | WO-2011/136645 A1 | 11/2011 |
| WO | WO-2012/047663 A2 | 4/2012 |
| WO | WO-2012/121973 A1 | 9/2012 |
| WO | WO-2012/134925 A1 | 10/2012 |
| WO | WO-2013/013244 A2 | 1/2013 |
| WO | WO-2013/036748 A1 | 3/2013 |
| WO | WO-2013/037824 A1 | 3/2013 |
| WO | WO-2013/132268 A1 | 9/2013 |
| WO | WO-2013/151697 A1 | 10/2013 |
| WO | WO-2014/065661 A1 | 5/2014 |

OTHER PUBLICATIONS

Hospital, Audrey. Access to functionalised silver(I) and gold(I) N-heterocylic carbenes by [2+3] dipolar cycloadditions. Dalton Trans. 2012, 41, 6803-6812.*

Beal et al., "Click-enabled heterotrifunctional template for sequential bioconjugations" Organic & Biomolecular Chemistry, 2012, vol. 10, pp. 548-554.

Bertozzi et al.,. "Second-generation difluorinated cyclooctynes for copper-free click chemistry", J Am Chem Soc, 2008, vol. 130, pp. 11486-11493.

(Continued)

*Primary Examiner* — Samantha L Shterengarts
(74) *Attorney, Agent, or Firm* — Foley & Lardner LLP

(57) ABSTRACT

A process is provided, comprising reacting a (hetero)aryl 1,3-dipole compound with a (hetero)cycloalkyne, wherein the (hetero)aryl 1,3-dipole compound comprises a 1,3-dipole functional group bonded to a (hetero)aryl group, and wherein the (hetero)aryl 1,3-dipole compound is a (hetero)aryl azide or a (hetero)aryl diazo compound;
wherein:
(i) the (hetero)aryl group of the (hetero)aryl 1,3-dipole compound comprises a substituent
(ii) the (hetero)aryl group of the (hetero)aryl 1,3-dipole compound is an electron-poor (hetero)aryl group
and wherein the (hetero)cycloalkyne is a (hetero)cyclooctyne or a (hetero)cyclononyne according to Formula (1). The invention also relates to the products obtainable by the process according to the invention.

28 Claims, 9 Drawing Sheets

(56) References Cited

OTHER PUBLICATIONS

Bertozzi et al., "A hydrophilic azacyclooctyne for cu-free click chemistry", Org. Lett., Jun. 2008, vol. 10, No. 14, pp. 3097-3099.
Bertozzi et al., "A strain-promoted [3 2] azide-alkyne cycloaddition for covalent modification of biomolecules in living systems", J Am Chem Soc, 2004, vol. 126, pp. 15046-15047.
Bertozzi et al., "Copper-free click chemistry for dynamic in vivo imaging", PNAS, Oct. 2007, vol. 104, No. 43, pp. 16793-16797.
Boeggeman et al., "Site specific conjugation of fluoroprobes to the remodeled Fc N-Glycans of monoclonal antibodies using mutant glycosyltransferases: Application for cell surface antigen detection", Bioconjugate Chemistry, 2009, vol. 20, pp. 1228-1236.
Boons et al., "Polar dibenzocyclooctynes for selective labeling of extracellular glycoconjugates of living cells", Journal of the American Chemical Society, 2012, vol. 134, pp. 5381-5389.
Dommerholt et al., "Readily accessible bicylononynes for bioorthogonal labeling and three-dimensional imaging of living cells", Angew. Chem. Int. Ed., 2010, vol. 49, pp. 9422-9425.
Elling et al., "Chemoenzymatic synthesis of biotinylated nucleotide sugars as substrates for glyosyltransferases", ChemBioChem, 2001, vol. 2, pp. 884-894.
Fang et al., "The mechanism of action of ramoplanin and enduracidin", Molecular Biosytems, 2006, vol. 2, pp. 69-76.
Fleet et al., "Affinity labeling of antibodies with aryl nitrene as reactive group", Nature, Nov. 1969, vol. 224, pp. 511-512.
Gordon et al., "Reactivity of biarylazacyclooctynones in copper-free click chemistry", Journal of the American Chemical Society, 2012, vol. 134, pp. 9199-9208.
Grenouillat et al., "Simple synthesis of nodulation-factor analogues exhibiting high affinity towards a specific binding protein", Angew. Chem. Int. Ed., 2004, vol. 43, pp. 4644-4646.
Gross et al., "Discovery of O-GlcNAc transferase inhibitors", Journal of the American Chemical Society, 2005, vol. 127, pp. 14588-14589.
Guan et al., "Highly efficient synthesis of UDP-GalNAc/GlcNAc analogues with promiscuous recombinant human UDP-GalNAc pyrophosphorylase AGX1", Chemistry—A European Journal, 2010, vol. 16, pp. 13343-13345.
International Search Report issued in International Patent Application No. PCT/NL2015/050044, dated May 27, 2015.
International Search Report issued in International Patent Application No. PCT/NL2015/050047, dated Mar. 19, 2015.
Jayaprakash et al., "Non-nucleoside building blocks for copper-assisted and copper-free click chemistry for the efficient synthesis of RNA conjugates", Organic Letters, 2010, vol. 12, No. 23, pp. 5410-5413.
Knorre et al., "Photoactivatable analogues of the initiating substrates of RNA polymerase II based on aryl azide derivatives of NTP Y-Amidophosphate: synthesis and chemical and photochemical reactions of functional groups", Russian Journal of Bioorganic Chemistry, 2005, vol. 31, No. 4, pp. 332-343.
Leeper et al., "Development and evaluation of new cyclooctynes for cell surface glycan imaging in cancer cells", Chemical Science, 2011, vol. 2, pp. 932-936.
Liu et al., "Perfluorophenyl azides: new appplications in surface functionalization and nanomaterial synthesis", Acc Chem Res., Nov. 2010, vol. 43, No. 11, pp. 1434-1443.
Manova et al., "Copper-free click biofunctionalization of silicon nitride surfaces via strain-promoted alkyne-azide cycloadditions reactions", Langmuir, 2012, vol. 28, pp. 8651-8663.
Masuko et al., "Chemoenzymatic synthesis of uridine disphosphate-GlcNAc and Uridine Diphosphate-GalNAc analogs for the preparation of unnatural glycosaminoglycans", The Journal of Organic Chemistry, 2012, vol. 77, pp. 1449-1456.
Pannecoucke et al., "6-Azido D-galactose transfer to N-acetyl-D-glucosamine derivative using commercially available B-1,4-galactosyltransferase", Tetrahedron Letters, 2008, vol. 49, pp. 2294-2297.

Qasba et al., "Structure-based design of B1,4-galactosyltransferase I (B4Gal-T1) with equally efficient N-Acetylgalactosaminyltransferase activity", The Journal of Biological Chemistry, Jun. 7, 2002, vol. 277, No. 23, pp. 20833-20839.
Temming et al., "N-terminal dual protein functionalization by strain promoted alkyne-nitrone cycloaddition" Organic & Biomolecular Chemistry, 2013, vol. 11, pp. 2772-2779.
Trinidade et al., "'Click and go': simple and fast folic acid conjugation", Organic & Biomolecular Chemistry, 2014, vol. 12, pp. 1381-3190.
Tummatorn et al., "Strain-promotes azide-alkyne cycloadditions of benzocyclononynes", The Journal of Organic Chemistry, 2012, vol. 77, pp. 2093-2097.
Van Delft et al., "Bioconjugation with strained alkenes and alkynes", Accounts of Chemical Research, 2011, vol. 44, No. 9, pp. 805-815.
Welle et al., "Tri- and tetravalent photoactivable cross-linking agents", Synthesis, 2012, vol. 44, pp. 2249-2254.
Zou et al., "One-pot three-enzyme synthesis of UDP-Glc, UDP-Gal, and their derivatives", Carbohydrate Research, 2013, vol. 373, pp. 76-81.
Etoc et al., "Subcellular control of Rac-GTPase signalling by magnetogenetic manipulation inside living cells", Nature Nanotechnology, Mar. 2013, vol. 8, pp. 193-198.
Friscourt et al., "A fluorogenic probe for the catalyst-free detection of azide-tagged molecules", Journal of the American Chemical Society, 2012, vol. 134, pp. 18809-18815.
Hospital et al., "Access to functionalised silver(I) and gold(I) N-heterocyclic carbenes by [2 3] dipolar cycloadditions", Dalton Transactions, 2012, vol. 41, pp. 6803-6812.
Jawalekar et al., "Synthesis of isoxazoles by hypervalent iodine-induced cycloaddition of nitrile oxides to alkynes", Chemical Communications, 2011, vol. 47, pp. 3198-3200.
Lisse et al., "Monofunctional stealth nanoparticle for unbiased single molecule tracking inside living cells", Nano Letters, 2014, vol. 14, pp. 2189-2195.
McKay et al., "Kinetics studies of rapid strain-promoted [3 2]-cycloadditions of nitrones with biaryl-aza-cyclooctynone", Organic & Biomolecular Chemistry, 2012, vol. 10, pp. 3066-3070.
McKay et al., "Nitrones as dipoles for rapid strain-promoted 1,3-dipolar cycloadditions with cyclooctynes", Chemical Communications, 2010, vol. 46, No. 6, pp. 931-933.
Mercer et al., "Use of novel mutant Galactosyltransferase for the bioconjugation of terminal N-Acetylglucosamine (GlcNAc) residues on live cell surface", Bioconjugate Chemistry, 2013, vol. 24, pp. 144-152.
Plougastel et al., "4-Halogeno-sydnones for fast strain promoted cycloaddition with bicycle-[6.1.0]-nonyne", Chemical Communications, 2014, vol. 50, pp. 9376-9378.
Qasba et al., "Site-specific linking of biomolecules via glycan residues using glycosyltransferases", Biotechnology Progress, 2008, vol. 24, pp. 520-526.
Sanders et al., "Metal-free sequential [3+2]-dipolar cycloadditions using cyclooctynes and 1,3-dipoles of different reactivity", Journal of the American Chemical Society, 2011, vol. 133, pp. 949-957.
Shieh et al., "Imaging bacterial peptidoglycan with near-infrared fluorogenic azide probes", PNAS, Apr. 15, 2014, vol. 111, No. 5, pp. 5456-5461.
Singh et al., "Fast RNA conjugations on solid phase by strain-promoted cycloadditions", Organic & Biomolecular Chemistry, 2012, vol. 10, pp. 6633-6639.
Wallace et al., "Strain-promoted sydnone bicycle-[6.1.0]-nonyne cycloaddition", Chemical Science, 2014, vol. 5, pp. 1742-1744.
Xie et al., 1,3-dipolar cycloaddition reactivities of perfluorinated aryl azides with enamines and strained dipolarophiles, The Journal of the American Chemical Society, 2015, vol. 137, pp. 2958-2966.
Zlatopolskiy et al., "Beyond azide-alkyne click reaction: easy access to F-labelled compounds via nitrile oxide cycloadditions", Chemical Communications, 2012, vol. 48, pp. 7134-7136.
International Search Report issued in International Patent Application No. PCT/NL2015/050045, dated Mar. 19, 2015.
Van Die et al. "The acceptor substrate specificity of human β4-galactosyltransferase V indicates its potential function in O-glycosylation." FEBS letters 450.1-2 (1999): 52-56.

(56) References Cited

OTHER PUBLICATIONS

Hansch et al. "A Survey of Hammett Substituent Constants and Resonance and Field Parameters." Chemical Reviews; vol. 91, No. 2 (1991) pp. 165-195.
"Cycloalkyne", Wikipedia; downloaded on Jan. 9, 2019.
Agard et a., "A Straom-Promoted [3+2] Azide-Alkyne Cycloaddition for Covalent Modification of Biomolecules in Living Systems", J. Am. Chern. Soc., vol. 126, pp. 15046-15047, 2004.
Aggeler et al., "Site-specific click chemistry-mediated labeling of antibody glycans using metabolic and enzymatic approaches" Poster published at The Essential Protein Engineering Summit, May 13, 2011, Boston, MA, USA.
Agnew et al., "Site-specific Labeling of Antibody N-glycans using a Click Chemistry-mediated Chemoenzymatic Approach", Journal of Biomolecular Techniques, vol. 23 (Supplement), 2012.
Allhorn et al., "Human IgG/FcyR Interactions Are Modulated by Streptococcal IgG Glycan Hydrolysis", PLoS One, vol. 3(1), e1413, 2008.
Banert et al., "Synthesis of Azidochloromethane and Azidobromomethane", Tetrahedron Letters, vol. 51, Mar. 27, 2010, pp. 2880-2882 (3 pages).
Baruah et al., "Selective Deactivation of Serum IgG: A General Strategy for the Enhancement of Monoclonal AntibodyReceptor Interactions", vol. 420(1-2), pp. 1-7, 2012.
Boeggeman et al., Direct Identification of Nonreducing GlcNac Residues on N-Glycans of Glycoproteins Using a Novel Chemoenzymatic Method, Bioconjugate Chem., vol. 18(3), pp. 806-814, 2007.
Boeggeman et al., "Site Specific Conjugation of Fluoroprobes to the Remodeled Fe N-Glycans of Monoclonal Antibodies Using Mutant Glycosyltransferases: Application for Cell Surface Antigen Detection", Bioconjugate Chem., vol. 20(6), pp. 1228-1236, 2009.
Collin et al., "EndoS, a novel secreted protein from Streptococcus pyogenes with endoglycosidase activity on human IgG", The EMBO Journal, vol. 20, No. 12, pp. 3046-3055, 2001.
Collin et al., "Extracellular Enzymes with Immunomodulating Activities: Variations on a Theme in *Streptococcus pyogenes*", Infection and Immunity, pp. 2983-2992, 2003.
De Bets et al., "Aza-dibenzocyclooctynes for fast and efficient enzyme PEGylation via copper-free (3+2) cycloaddition", ChemComm, vol. 46, pp. 97-99, 2010.
De Bets et al., "Bioconjugation with Strained Alkenes and Alkynes", Accounts of Chemical Research, vol. 44(9), pp. 805-815, 2011.
Debets et al., "Azide: A Unique Dipole for Metal-Free Bioorthogonal Ligations", Chem Bio Chem, vol. 11, pp. 1168-1184, 2010.
Dommerhold et al., "Strain-Promoted 1,3-Dipolar Cycloaddition of Cycloalkynes and Organic Azides", To Curr Chem (Z), 374:16, 2016.
European Unpublished Patent Application No. 12189604.7, dated Oct. 23, 2012.
European Unpublished Patent Application No. 13188607.9, dated Oct. 14, 2013.
Goodfellow et al., "An Endoglycosidase with Alternative Glycan Specificity Allows Broadened Glycoprotein Remodelling", J. Am. Chem. Soc., vol. 134, pp. 8080-8033, 2012.
Huang et al., "Chemoenzymatic Glycoengineering of intact IgG Antibodies for Gain of Functions", J. Am. Chem. Soc., vol. 134, pp. 12308-12318, 2012.
Juntula et al., "Engineered Thio-Trastuzumab-DM1 Conjugate with an Improved Therapeutic Index to Target Human Epidermal Growth Factor Receptor 2-Positive Breast Cancer", Clinical Cancer Research, vol. 16(19), DD. 4469-4768, 2010.
Lallana, et al., "Reliable and Efficient Procedures for the Conjugation of Biomolecules through Huisgen Azide-Alkyne Cycloadditions", Angew. Chem. Int. Ed. Engl., vol. 50, pp. 8794-8804, 2011.
Lugovskoy et al., "7th Annual European Antibody Congress 2011", mAbs 4:2, pp. 134-152, 2011.
Ning et al., Visualizing Metabolically Labeled Glycoconjugates of Living Cells by Copper-Free and Fast Huisgen Cycloadditions, Angew. Chem. Int. Ed., vol. 47, pp. 2253-2255, 2008.
Qasba, et al., "Mutant Glycosyltransferases Assist in the Development of a Targeted Drug Delivery System and Contrast Agents for MRI", The AAPS Journal, vol. 8(1), pp. E190-E 195, 2006.
Ramakrishnan et al., "Bioconjugation Using Mutant Glycosyltransferases for the Site-Specific Labeling of Biomolecules with Sugars Carrying Chemical Handles", Methods in Molecular Biology, vol. 751, pp. 281-296, 2011.
Ramakrishnan et al., Structure-based Design of 131, 4-Galactosyltransferase I (134Gal-T1) with Equally Efficient N-Acetylgalactosaminyltransferase Activity, J. Biol. Chem., 277:23, pp. 20833-20839, 2002.
Sharkey et al., "Use of antibodies and immunoconjugates for the therapy of more accessible cancers", Adv. Drug Deliv. Rev., vol. 60(12), pp. 1407-1420, 2008.
Tarentino et al., "Enzymatic Deglycosylation of Asparagine-Linked Glycans: Purification, Properties, and Specificity of Oligosaccharide-Cleaving Enzymes from Flavobacterium meningosepticum", Methods in Enzymology, vol. 230, pp. 44-57, 1994.
Trimble et al., "Identification of Distinct Endoglycosidase (Endo) Activities in Flavobacterium meningosepticum: Endo F1, Endo F2, and Endo F3", Biol. Chem., vol. 266(3), pp. 1646-1652, 1991.
Van Geel et al., "Chemoenzymatic Conjugation of Toxic Payloads to the Globally Conserved N-Glycan of Native mAbs Provides Homogeneous and Highly Efficacious Antibody-Drug Conjugates", Bioconjug Chern., vol. 26(11), pp. 2233-2242, 2015.
Wandall et al., "Substrate Specificities of Three Members of the Human", JBC, vol. 272, No. 38, Sep. 19, 1997, pp. 23503-23514, The American Society for Biochemistry and Molecular Biology, Inc. (13 pages).
Whisstock et al., "Prediction of protein function from protein sequence and structure", Quarterly Reviews of Biophysics, 2003, vol. 36, No. 3, pp. 307-340.

\* cited by examiner

PROCESS FOR THE CYCLOADDITION OF A HETERO(ARYL) 1,3-DIPOLE COMPOUND WITH A (HETERO)CYCLOALKYNE

CROSS-REFERENCE TO RELATED APPLICATIONS

This application is the National Phase of International Patent Application No. PCT/NL2015/050045, filed Jan. 26, 2015, published on Jul. 30, 2015 as WO 2015/112014 A1, which claims priority to European Patent Application No. 14152420.7, filed Jan. 24, 2014. The contents of these applications are herein incorporated by reference in their entirety.

FIELD OF THE INVENTION

The present invention is in the field of 1,3-dipolar cycloaddition reactions. The invention relates to a process for the 1,3-dipolar cycloaddition of a (hetero)aryl 1,3-dipole compound with a (hetero)cycloalkyne. In particular, the invention relates to the 1,3-dipolar cycloaddition of a (hetero)aryl azide or a (hetero)aryl diazo compound, with a (hetero)cyclooctyne or a (hetero)cyclononyne.

BACKGROUND OF THE INVENTION

A 1,3-dipolar cycloaddition, also called Huisgen (3+2) cycloaddition, is a chemical reaction between a 1,3-dipole and a dipolarophile to form a five-membered ring. Typical dipoles that are used in (3+2) cycloaddition reactions involve azides, nitrones, nitrile oxides and diazo compounds, to react with alkynes or alkenes as dipolarophile, leading to five-membered heterocycles. Typical conditions for Huisgen cycloaddition involve the prolonged heating of starting components. However, cycloaddition can also be induced by means of addition of a metal catalyst or by means of the use of a strained alkene or alkyne.

Strain-promoted azide-alkyne cycloaddition (SPAAC) involves the formation of a 1,2,3-triazole by reaction of an azide with a strained, cyclic alkyne. Apart from azides, strained alkynes also show high reactivity with other dipoles, such as nitrones and nitrile oxides (SPANOC). For example, the strain-promoted alkyne-nitrone cycloaddition (SPANC) was applied for the N-terminal modification of proteins.

SPAAC and SPANC cycloaddition reactions proceed spontaneously, hence in the absence of a (metal) catalyst, and these and a select number of additional cycloadditions are also referred to as "metal-free click reactions".

Original reports on the reaction of phenyl azide with cyclooctyne date back more than 50 years, but it was not until 2004 that the practical use of SPAAC was recognized for the functional connection of two molecular entities, connected to azide or cyclooctyne, respectively. For example, Bertozzi et al. have demonstrated in J. Am. Chem. Soc. 2004, 126, 15046 (incorporated by reference) that incubation of Jurkat cells with azide-functionalized mannosamine led to effective exposure of azide on the cell surface, as visualized by treatment with cyclooctyne-conjugated biotin, then staining with FITC-avidin and flow cytometry. However, it was also found that the reaction rate of plain cyclooctyne with azide was relatively low, for example less effective than similar staining of azide-labelled cells with copper-catalyzed cycloaddition of azide with a biotinylated terminal alkyne (CuAAC) or with a phospine reagent (Staudinger ligation). As a consequence, in subsequent years much attention has been focused on the development of cyclooctynes with superior reaction rates, for example difluorocyclooctyne (DIFO), dibenzocyclooctynol (DIBO), dibenzoazacyclooctyne (DIBAC/DBCO) and bisarylazacyclooctynone (BARAC), bicyclo[6.1.0]nonyne (BCN) and carboxymethylmonobenzocyclooctyne (COMBO). Of these, the most frequently applied cyclooctynes are DIBO, DIBAC and BCN, all of which are commercially available and display high reactivity in cycloadditions not only with azides, but also other 1,3-dipoles such as nitrones, nitrile oxides and diazo compounds.

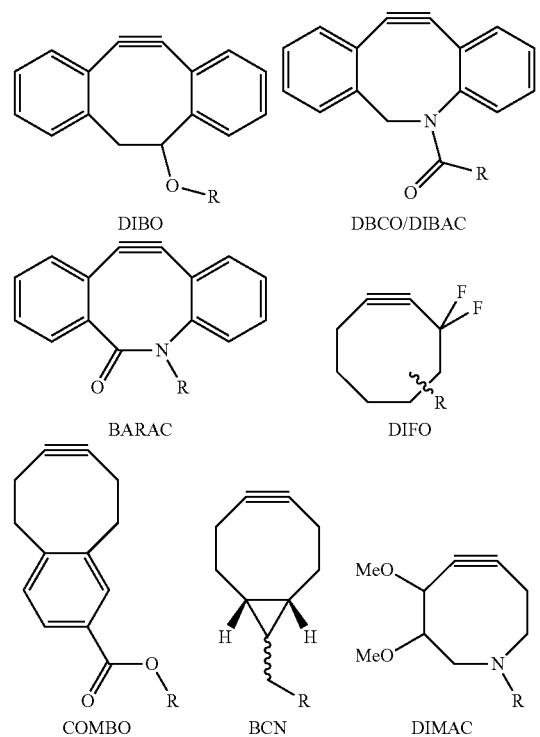

An example of a cyclononyne is the benzocyclononyne shown below, disclosed by Tummatorn et al., J. Org. Chem. 2012, 77, 2093, incorporated by reference.

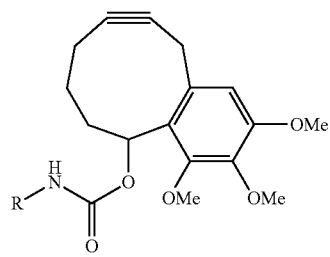

The ease of operation of SPAAC and the high stability of the resulting triazole functionality have led to a wide range of applications, including in vitro and in vivo labelling, patterning of solid surfaces, formation of bioconjugates from proteins, nucleic acid and glycans, medical applications etc. Two prime parameters that determine the choice of cyclooctyne for a particular application are lipophilicity and reaction rate. Since the vast majority of cyclooctynes exist predominantly of hydrocarbon, they are typically hydrophobic and hence poorly water-soluble. To enhance water-solubility, Bertozzi et al. developed dimethoxy-azacyclooctyne (DIMAC) from a carbohydrate precursor, as reported in Org. Lett. 2008, 10, 3097 (incorporated by reference), but the increase in polarity was accompanied by attenuated reactivity. Clearly, the earlier mentioned benzoannulated cyclooctynes (DIBO, DIBAC and BARAC) are highly reactive but application in aqueous system is suboptimal due to the hydrophobic nature of the probes. A comparison of reactivity (with azide) versus lipophilicity ($^C$ log P) for the vast majority of reported cyclooctynes is provided in FIG. 1 (taken from van Delft et al., Acc. Chem. Res. 2011, 44, 805, incorporated by reference).

Despite their suboptimal lipophilicity, SPAAC is currently most often performed with dibenzoannulated cyclooctyne DIBO or DIBAC, both of which are relatively stable, commercially available and highly reactive with a range of 1,3-dipoles, including nitrones and azides. One strategy to further enhance the properties of a benzoannulated cyclooctyne is by increase of water-solubility, as was demonstrated for derivatization of DIBO by aromatic sulfonation (Boons et al., 2012, 134, 5381, incorporated by reference) or by tetramethoxy-substitution (Leeper et al. 2011, 2, 932, incorporated by reference). However, it is also clear that from a steric perspective it would be desirable to avoid the presence of a (bulky) aromatic functionality in a cyclooctyne altogether. Another approach involves similar solubility enhancement of an aliphatic cyclooctyne, such as DIFO or BCN, but this would typically involve a lengthy synthetic route with potentially compromised reactivity. At the same time, it is generally accepted and it has been well-documented that DIFO and BCN are less reactive in dipolar cycloadditions than the benzoannulated cyclooctynes.

In summary, reaction of an azide or a nitrone, or of a 1,3-dipole in general, with a (di)benzoannulated cyclooctyne is preferable with respect to an aliphatic cyclooctyne from a reactivity point of view, but suboptimal from a steric and water-solubility perspective. Thus, the desire to optimize hand-in-hand polarity and reactivity of cyclooctynes is continuously driving research for further improvement.

In a recent report, Bertozzi et al. in J. Am. Chem. Soc. 2012, 134, 9199, incorporated by reference, explicitly mention that BARAC reacts with azide faster than any other reported cyclooctyne, thereby underlining the general perception that reaction rate of cyclooctynes is not influenced by azide substituents (aliphatic or aromatic or substituted versions). An important finding of the same report involves the enhancement of reaction rate of benzyl azide with BARAC upon difluorination of BARAC. Based on free energy calculations, it is concluded that the reaction rate enhancement is a result of electronic modulation that generates enhanced stabilizing interactions in the transition state. The finding that the introduction of electron-withdrawing fluoride substituents on the cyclooctyne BARAC leads to reaction rate increase with azide is nicely in line with earlier observations for different versions of DIFO (Bertozzi et al. Proc. Natl. Acad. Sci. 2007, 104, 16793 and J. Am. Chem. Soc. 2008, 130, 11486, incorporated by reference). In both cases, it is reasoned that installing fluorine atoms leads to lowering of the cyclooctyne LUMO, thereby increasing its interaction energy with the HOMO of the azide. Hence, it can be concluded that an electron-rich azide, with higher HOMO, will react faster with cyclooctyne than an electron-poor azide.

Pezacki et al. (Org. Biomol. Chem. 2012, 10, 3066, incorporated by reference) have explored the influence on reaction rate of aromatic substituents on benzaldehyde-derived nitrones with BARAC. Interestingly, it was established that the cycloaddition reaction is not sensitive to substituents on the dipole, so that no significant rate enhancement can be obtained through aromatic substitution.

Finally, one halogenated aryl azide with particular application in the field of labeling is 4-azido-2,3,5,6-tetrafluorobenzoic acid ($N_3$-TFBA). Originally introduced by Fleet et al. in Nature 1969, 224, 511, incorporated by reference, aryl azides have become popular precursors of nitrenes as versatile photoaffinity labeling agents. Upon photolysis, $N_2$ is liberated and a highly unstable singlet phenylnitrene is formed in situ, which reacts with neighbouring molecules in a variety of reactions. Perfluorophenyl azides are of particular interest in the field of photoaffinity labeling because highly stabilized nitrene intermediates are formed that undergo insertion and addition reaction in moderate to good yields rather than intermolecular rearrangements. For this purpose, a variety of derivatives of 4-azido-2,3,5,6-tetrafluorobenzoic acid ($N_3$-TFBA) are commercially available and have been applied for labeling of biomolecules, polymers, small molecules, carbon materials, gold/silver, metal oxides and silicate/semiconductors, as inter alia reviewed in Liu et al. Acc. Chem. Res. 2011, 43, 1434 and Welle et al. Synthesis 2012, 44, 2249, both incorporated by reference. However, none of the earlier applications of $N_3$-TFBA mention labeling or conjugation by strain-promoted cycloaddition reaction.

SUMMARY OF THE INVENTION

The present invention relates to a process comprising the step of reacting a (hetero)aryl 1,3-dipole compound with a (hetero)cycloalkyne; wherein a (hetero)aryl 1,3-dipole compound is defined as a compound comprising a 1,3-dipole functional group, wherein the 1,3-dipole functional group is bonded to a (hetero)aryl group;

wherein:
(i) the (hetero)aryl group of the (hetero)aryl 1,3-dipole compound comprises one or more substituents having a positive value for the para-Hammett substituent constant $\sigma_p$ and/or the meta-Hammett substituent constant $\sigma_m$, and/or
(ii) the (hetero)aryl group of the (hetero)aryl 1,3-dipole compound is an electron-poor (hetero)aryl group, wherein an electron-poor (hetero)aryl group is:
  (ii-a) a (hetero)aryl group wherein the (hetero)aromatic ring system is bearing a positive charge, and/or
  (ii-b) a (hetero)aryl group wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring;

and wherein the (hetero)cycloalkyne is according to Formula (1):

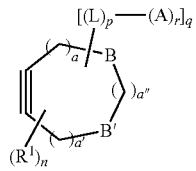

wherein:
a is 0-8;
a' is 0-8;
a" is 0-8;
with the proviso that a+a'+a"=4, 5, 6, 7 or 8;
n is 0-16;
$R^1$ is independently selected from the group consisting of —$OR^2$, —$NO_2$, —CN, —$S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein $R^2$ is independently selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups;

B and B' are independently selected from the group consisting of O, S, C(O), $NR^3$ and $C(R^3)_2$, wherein $R^3$ is independently selected from the group consisting of hydrogen, $R^1$ or $(L)_p$-$(A)_r$;

optionally, when n is 2 or more, two $R^1$ groups may together form a (hetero)cycloalkyl group, the (hetero)cycloalkyl group optionally being substituted with an $(L)_p$-$(A)_r$ substituent;

optionally, when a'' is 2 or more and n is 2 or more, two $R^1$ groups present on adjacent a''-C-atoms may together form a (hetero)aryl group, the (hetero)aryl group optionally being substituted with an $(L)_p$-$(A)_r$ substituent;

p is 0 or 1;
r is 1-4;
L is a linker;
A is independently selected from the group consisting of D, E and Q, wherein D, E and Q are as defined below;
q is 0-4;

with the proviso that if q is 0, then B and/or B' is $NR^3$ wherein $R^3$ is $(L)_p$-$(A)_r$, and/or B and/or B' is $C(R^3)_2$ wherein one or more $R^3$ is $(L)_p$-$(A)_r$, and/or n is 2 or more and two $R^1$ groups together form a (hetero)cycloalkyl group wherein the (hetero)cycloalkyl group is substituted with an $(L)_p$-$(A)_r$ substituent, and/or a'' is 2 or more and n is 2 or more and two $R^1$ groups present on adjacent a''-C-atoms together form a (hetero)aryl group wherein the (hetero)aryl group is substituted with an $(L)_p$-$(A)_r$ substituent;

D is a molecule of interest;
E is a solid surface; and
Q is a functional group.

In particular, the invention relates to a process as defined above, wherein the (hetero)aryl 1,3-dipole compound is a (hetero)aryl azide or a (hetero)aryl diazo compound; wherein the (hetero)cycloalkyne is an aliphatic (hetero)cycloalkyne, wherein an aliphatic (hetero)cycloalkyne is defined as a (hetero)cycloalkyne wherein both $sp^1$ C-atoms of the (hetero)cycloalkyne carbon-carbon triple bond are bonded to an $sp^3$ C-atom; and wherein the (hetero)cycloalkyne is a (hetero)cyclooctyne or a (hetero)cyclononyne according to Formula (1), wherein:

when the (hetero)cycloalkyne is a (hetero)cyclooctyne:
a is 1, 2, 3 or 4;
a' is 1, 2, 3 or 4;
a'' is 1, 2, 3 or 4;
with the proviso that a+a'+a''=4; and
n is 0-8; or when the (hetero)cycloalkyne is a (hetero)cyclononyne:
a is 1, 2, 3, 4 or 5;
a' is 1, 2, 3, 4 or 5;
a'' is 1, 2, 3, 4 or 5;
with the proviso that a+a'+a''=5; and
n is 0-10.

The invention further relates to compounds obtainable by the process according to the invention. In particular, the invention relates to a compound according to Formula (12a) or (12d):

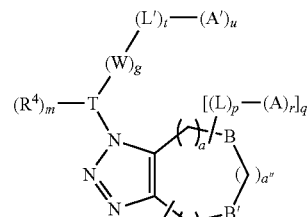

12a

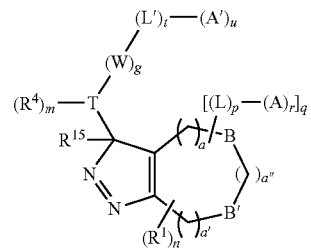

12d wherein:
$R^1$, n, B, B', a, a', a'', L, p, q, r and A are as defined above;
t is 0 or 1;
u is 1-4;
m is 0-8;
with the proviso that when m is 0, then T is an electron-poor (hetero)aryl group, wherein an electron-poor (hetero)aryl group is as defined above;
g is 0 or 1;
L' is a linker;
A' is independently selected from the group consisting of D, E and Q, wherein D, E and Q are as defined above;
T is selected from the group consisting of (hetero)aryl groups;
$R^4$ is independently selected from the group consisting of electron-withdrawing substituents having a positive value for the para-Hammett substituent constant $\sigma_p$ and/or the meta-Hammett substituent constant $\sigma_m$;
W is selected from the group consisting of $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N; and
$R^{15}$ is selected from the group consisting of hydrogen, $C_1$-$C_{24}$ alkyl groups, $C_2$-$C_{24}$ alkenyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkenyl groups, cycloalkyl groups, (hetero)aryl groups, alkyl(hetero)aryl groups and (hetero)arylalkyl groups are optionally substituted, and wherein the alkyl groups, alkenyl groups, cycloalkyl groups, (hetero)aryl groups, alkyl(hetero)aryl groups and (hetero)arylalkyl groups are optionally interrupted by one or more heteroatoms selected from the group consisting of O, S and N.

The invention particularly relates to a compound according to Formula (12a) or (12d), wherein n is 0-8 and a, a' and a'' are independently 1, 2, 3 or 4, with the proviso that a+a'+ a''=4; or wherein n is 0-10 and a, a' and a'' are independently 1, 2, 3, 4 or 5, with the proviso that a+a'+a''=5.

DETAILED DESCRIPTION OF THE INVENTION

Definitions

Figure 1:
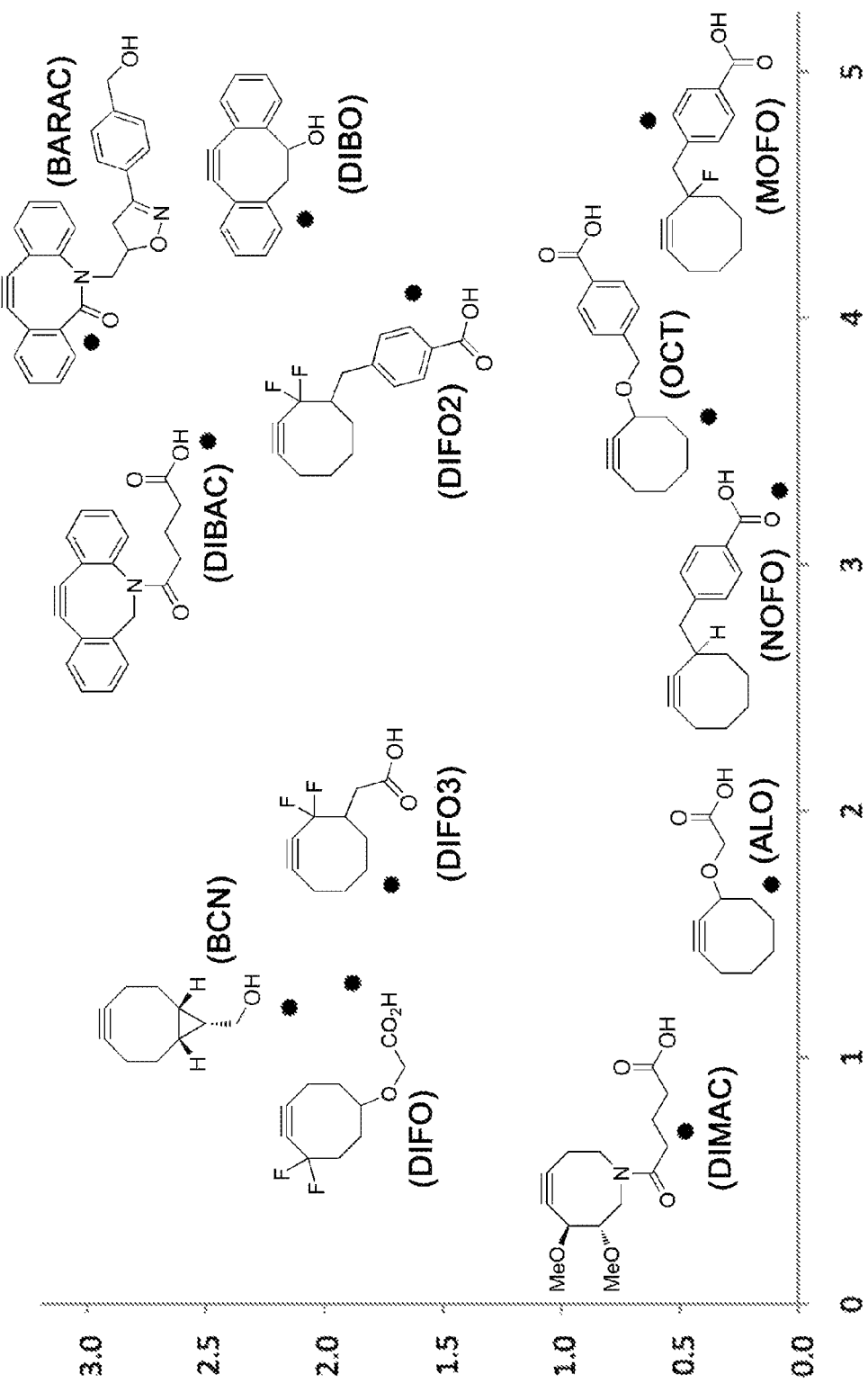
In FIG. 1, a comparison of relative reaction rate (X-axis) versus lipophilicity ($^C$log P, Y-axis) for a number of reported cyclooctynes with azides is provided.

The verb "to comprise" as is used in this description and in the claims and its conjugations is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one".

The compounds disclosed in this description and in the claims may comprise one or more asymmetric centres, and different diastereomers and/or enantiomers may exist of the compounds. The description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer.

The compounds may occur in different tautomeric forms. The compounds according to the invention are meant to include all tautomeric forms, unless stated otherwise. When the structure of a compound is depicted as a specific tautomer, it is to be understood that the invention of the present application is not limited to that specific tautomer.

The compounds disclosed in this description and in the claims may further exist as exo and endo diastereoisomers. Unless stated otherwise, the description of any compound in the description and in the claims is meant to include both the individual exo and the individual endo diastereoisomers of a compound, as well as mixtures thereof. When the structure of a compound is depicted as a specific endo or exo diastereomer, it is to be understood that the invention of the present application is not limited to that specific endo or exo diastereomer.

Furthermore, the compounds disclosed in this description and in the claims may exist as cis and trans isomers. Unless stated otherwise, the description of any compound in the description and in the claims is meant to include both the individual cis and the individual trans isomer of a compound, as well as mixtures thereof. As an example, when the structure of a compound is depicted as a cis isomer, it is to be understood that the corresponding trans isomer or mixtures of the cis and trans isomer are not excluded from the invention of the present application. When the structure of a compound is depicted as a specific cis or trans isomer, it is to be understood that the invention of the present application is not limited to that specific cis or trans isomer.

Unsubstituted alkyl groups have the general formula $C_nH_{2n+1}$ and may be linear or branched. Optionally, the alkyl groups are substituted by one or more substituents further specified in this document. Examples of alkyl groups include methyl, ethyl, propyl, 2-propyl, t-butyl, 1-hexyl, 1-dodecyl, etc.

Unsubstituted cycloalkyl groups comprise at least three carbon atoms and have the general formula $C_nH_{2n-1}$. Optionally, the cycloalkyl groups are substituted by one or more substituents further specified in this document. Examples of cycloalkyl groups include cyclopropyl, cyclobutyl, cyclopentyl, cyclohexyl, etc.

Unsubstituted alkenyl groups have the general formula $C_nH_{2n-1}$, and may be linear or branched. Examples of suitable alkenyl groups include, but are not limited to, ethenyl, propenyl, isopropenyl, butenyl, pentenyl, decenyl, octadecenyl, and eicosenyl and the like. Unsubstituted alkenyl groups may also contain a cyclic moiety, and thus have the concomitant general formula $C_nH_{2n-3}$.

An aryl group comprises six to twelve carbon atoms and may include monocyclic and bicyclic structures. Optionally, the aryl group may be substituted by one or more substituents further specified in this document. Examples of aryl groups are phenyl and naphthyl.

Arylalkyl groups and alkylaryl groups comprise at least seven carbon atoms and may include monocyclic and bicyclic structures. Optionally, the arylalkyl groups and alkylaryl may be substituted by one or more substituents further specified in this document. An arylalkyl group is for example benzyl. An alkylaryl group is for example 4-t-butylphenyl.

Heteroaryl groups comprise at least two carbon atoms (i.e. at least $C_2$) and one or more heteroatoms N, O, P or S. A heteroaryl group may have a monocyclic or a bicyclic structure. Optionally, the heteroaryl group may be substituted by one or more substituents further specified in this document. Examples of suitable heteroaryl groups include pyridinyl, quinolinyl, pyrimidinyl, pyrazinyl, pyrazolyl, imidazolyl, thiazolyl, pyrrolyl, furanyl, triazolyl, benzofuranyl, indolyl, purinyl, benzoxazolyl, thienyl, phospholyl and oxazolyl.

Heteroarylalkyl groups and alkylheteroaryl groups comprise at least three carbon atoms (i.e. at least $C_3$) and may include monocyclic and bicyclic structures. Optionally, the heteroaryl groups may be substituted by one or more substituents further specified in this document.

Where an aryl group is denoted as a (hetero)aryl group, the notation is meant to include an aryl group and a heteroaryl group. Similarly, an alkyl(hetero)aryl group is meant to include an alkylaryl group and a alkylheteroaryl group, and (hetero)arylalkyl is meant to include an arylalkyl group and a heteroarylalkyl group. A $C_2$-$C_{24}$ (hetero)aryl group is thus to be interpreted as including a $C_2$-$C_{24}$ heteroaryl group and a $C_6$-$C_{24}$ aryl group. Similarly, a $C_3$-$C_{24}$ alkyl(hetero)aryl group is meant to include a $C_7$-$C_{24}$ alkylaryl group and a $C_3$-$C_{24}$ alkylheteroaryl group, and a $C_3$-$C_{24}$ (hetero)arylalkyl is meant to include a $C_7$-$C_{24}$ arylalkyl group and a $C_3$-$C_{24}$ heteroarylalkyl group.

Unless stated otherwise, alkyl groups, alkenyl groups, alkenes, alkynes, (hetero)aryl groups, (hetero)arylalkyl groups, alkyl(hetero)aryl groups, alkylene groups, alkenylene groups, cycloalkylene groups, (hetero)arylene groups, alkyl(hetero)arylene groups, (hetero)arylalkylene groups, alkenyl groups, alkynyl groups, cycloalkyl groups, alkoxy groups, alkenyloxy groups, (hetero)aryloxy groups, alkynyloxy groups and cycloalkyloxy groups may be substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens (F, Cl, Br, I), amino groups, oxo and silyl groups, wherein the silyl groups can be represented by the formula $(R^{Si})_3Si-$, wherein $R^{Si}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S.

An alkynyl group comprises a carbon-carbon triple bond. An unsubstituted alkynyl group comprising one triple bond has the general formula $C_nH_{2n-3}$. A terminal alkynyl is an alkynyl group wherein the triple bond is located at a terminal position of a carbon chain. Optionally, the alkynyl group is substituted by one or more substituents further specified in this document, and/or interrupted by heteroatoms selected from the group of oxygen, nitrogen and sulphur. Examples of alkynyl groups include ethynyl, propynyl, butynyl, octynyl, etc.

A cycloalkynyl group is a cyclic alkynyl group. An unsubstituted cycloalkynyl group comprising one triple bond has the general formula $C_nH_{2n-5}$. Optionally, a cycloalkynyl group is substituted by one or more substituents further specified in this document. An example of a cycloalkynyl group is cyclooctynyl.

A heterocycloalkynyl group is a cycloalkynyl group interrupted by heteroatoms selected from the group of oxygen, nitrogen and sulphur. Optionally, a heterocycloalkynyl group is substituted by one or more substituents further specified in this document. An example of a heterocycloalkynyl group is azacyclooctynyl.

The term "(hetero)aryl group" comprises an aryl group and a heteroaryl group. The term "alkyl(hetero)aryl group" comprises an alkylaryl group and an alkylheteroaryl group. The term "(hetero)arylalkyl group" comprises an arylalkyl group and a heteroarylalkyl group. The term "(hetero)alkynyl group" comprises an alkynyl group and a heteroalkynyl group. The term "(hetero)cycloalkynyl group" comprises an cycloalkynyl group and a heterocycloalkynyl group.

A (hetero)cycloalkyne compound is herein defined as a compound comprising a (hetero)cycloalkynyl group.

Several of the compounds described in this description and in the claims may be described as fused (hetero)cycloalkyne compounds, i.e. (hetero)cycloalkyne compounds wherein a second ring structure is fused, i.e. annulated, to the (hetero)cycloalkynyl group. For example in a fused (hetero)cyclooctyne compound, a cycloalkyl (e.g. a cyclopropyl) may be annulated to the (hetero)cyclooctynyl group. Unless otherwise stated, the triple bond of the (hetero)cyclooctynyl group in a fused (hetero)cyclooctyne compound wherein a (hetero)cycloalkyl group is fused to a (hetero)cyclooctyne may be located on either one of the three possible locations, i.e. on the 2, 3 or 4 position of the cyclooctyne moiety (numbering according to "IUPAC Nomenclature of Organic Chemistry", Rule A31.2). The description of a fused (hetero)cyclooctyne compound wherein a (hetero)cycloalkyl group is fused to a (hetero)cycloalkyne, in this description and in the claims is meant to include all three individual regioisomers of the cyclooctyne moiety.

Cycloaddition of a (hetero)aryl 1,3-dipole compound with a (hetero)cycloalkyne

The present invention discloses a process for the cycloaddition of a (hetero)aryl 1,3-dipole compound with a (hetero)cycloalkyne. A cycloaddition of a 1,3-dipole compound with an alkyne is also referred to as a 1,3-dipolar cycloaddition.

In a first aspect, the invention relates to a process comprising the step of reacting a (hetero)aryl 1,3-dipole compound with a (hetero)cycloalkyne;

wherein a (hetero)aryl 1,3-dipole compound is defined as a compound comprising a 1,3-dipole functional group, wherein the 1,3-dipole functional group is bonded to a (hetero)aryl group;

wherein:
(i) the (hetero)aryl group of the (hetero)aryl 1,3-dipole compound comprises one or more substituents having a positive value for the para-Hammett substituent constant $\sigma_p$ and/or the meta-Hammett substituent constant $\sigma_m$, and/or (ii) the (hetero)aryl group of the (hetero)aryl 1,3-dipole compound is an electron-poor (hetero)aryl group, wherein an electron-poor (hetero)aryl group is:

(ii-a) a (hetero)aryl group wherein the (hetero)aromatic ring system is bearing a positive charge, and/or (ii-b) a (hetero)aryl group wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring;

and wherein the (hetero)cycloalkyne is according to Formula (1):

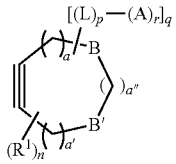

wherein:
a is 0-8;
a' is 0-8;
a" is 0-8;
with the proviso that a+a'+a"=4, 5, 6, 7 or 8;
n is 0-16;
$R^1$ is independently selected from the group consisting of —$OR^2$, —$NO_2$, —CN, —$S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein $R^2$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups; B and B' are independently selected from the group consisting of O, S, C(O), $NR^3$ and $C(R^3)_2$, wherein $R^3$ is independently selected from the group consisting of hydrogen, $R^1$ or $(L)_p$-$(A)_r$;
optionally, when n is 2 or more, two $R^1$ groups may together form a (hetero)cycloalkyl group, the (hetero)cycloalkyl group optionally being substituted with an $(L)_p$-$(A)_r$ substituent;
optionally, when a" is 2 or more and n is 2 or more, two $R^1$ groups present on adjacent a"-C-atoms may together form a (hetero)aryl group, the (hetero)aryl group optionally being substituted with an $(L)_p$-$(A)_r$ substituent;
p is 0 or 1;
r is 1-4;
L is a linker;
A is independently selected from the group consisting of D, E and Q, wherein D, E and Q are as defined below;
q is 0-4;
with the proviso that if q is 0, then B and/or B' is $NR^3$ wherein $R^3$ is $(L)_p$-$(A)_r$, and/or B and/or B' is $C(R^3)_2$ wherein one or more $R^3$ is $(L)_p$-$(A)_r$, and/or n is 2 or more and two $R^1$ groups together form a (hetero)cycloalkyl group wherein the (hetero)cycloalkyl group is substituted with an $(L)_p$-$(A)_r$ substituent, and/or a" is 2 or more and n is 2 or more and two $R^1$ groups present on adjacent a"-C-atoms together form a (hetero)aryl group wherein the (hetero)aryl group is substituted with an $(L)_p$-$(A)_r$ substituent;
D is a molecule of interest;
E is a solid surface; and
Q is a functional group,
to form the cycloaddition product of said (hetero)aryl 1,3-dipole compound and (hetero)cycloalkyne.

In a particularly preferred embodiment of the process according to the invention, the (hetero)aryl 1,3-dipole compound is a (hetero)aryl azide or a (hetero)aryl diazo compound. Most preferably, the (hetero)aryl 1,3-dipole compound is a (hetero)aryl azide.

In another particularly preferred embodiment, the (hetero)cycloalkyne is an aliphatic (hetero)cycloalkyne, wherein an aliphatic (hetero)cycloalkyne is defined as a (hetero)cycloalkyne wherein both $sp^1$ C-atoms of the (hetero)cycloalkyne carbon-carbon triple bond are bonded to an $sp^3$ C-atom.

In another particularly preferred embodiment, the (hetero)cycloalkyne according to Formula (1), as defined above, is a (hetero)cyclooctyne or a (hetero)cyclononyne. Most preferably, the (hetero)cycloalkyne according to Formula (1) is a (hetero)cyclooctyne.

When the (hetero)cycloalkyne according to Formula (1) is a (hetero)cyclooctyne, a is 0, 1, 2, 3 or 4; a' is 0, 1, 2, 3 or 4; a" is 0, 1, 2, 3 or 4; with the proviso that a+a'+a"=4; and n is 0-8. When the (hetero)cycloalkyne according to Formula (1) is an aliphatic (hetero)cyclooctyne, a is 1, 2, 3 or 4; a' is 1, 2, 3 or 4; a" is 1, 2, 3 or 4; with the proviso that a+a'+a"=4; and n is 0-8.

When the (hetero)cycloalkyne according to Formula (1) is an aliphatic (hetero)cyclononyne, a is 1, 2, 3, 4 or 5; a' is 1, 2, 3, 4 or 5; a" is 1, 2, 3, 4 or 5; with the proviso that a+a'+a"=5; and n is 0-10.

In another particularly preferred embodiment, the (hetero)aryl 1,3-dipole compound is a (hetero)aryl azide or a (hetero)aryl diazo compound (preferably a (hetero)aryl azide), and the (hetero)cycloalkyne according to Formula (1) is an aliphatic (hetero)cyclooctyne or an aliphatic (hetero)cyclononyne (preferably a (hetero)cyclooctyne). An aliphatic (hetero)cycloalkyne is herein defined as a (hetero)cycloalkyne wherein both $sp^1$ C-atoms of the (hetero)cycloalkyne carbon-carbon triple bond are bonded to an $sp^3$ C-atom.

The (hetero)aryl 1,3-dipole compound and the (hetero)cycloalkyne, and preferred embodiments thereof, are described in more detail below.

The process for the cycloaddition of a (hetero)aromatic 1,3-dipole compound and a (hetero)cycloalkyne is preferably performed in a suitable solvent, for example dichloromethane, chloroform, THF, Me-THF, ethyl acetate, diethyl ether, DMF, DMA, toluene, benzene, xylene, acetone or hexane. The process may also be performed in water or a mixture of water and a water-miscible solvent (i.e. acetonitrile or THF). Alternatively, the reaction can be performed without any solvent (neat).

The process is preferably performed at a temperature in the range of about −78° C. to about 300° C., more preferably in the range of −40° C. to 200° C., even more preferably in the range of about −20° C. to 100° C., and most preferably in the range of about 0° C. to 60° C.

The process is preferably performed with a stoichiometry of reagents in the range of 10 to 1 (or vice versa), more preferably in the range of 5 to 1, even more preferably in the range of 2 to 1, and most preferably in the range close to 1 to 1. The process is thus preferably performed with a stoichiometry of reagents in the range of 10:1 to 1:10. More preferably the process is performed with a stoichiometry of reagents in the range of 5:1 to 1:5, even more preferably in the range of 2:1 to 1:2. In one embodiment, when one of the reagents is present in excess, it is preferred that the (hetero)aryl 1,3-dipole compound is present in excess, i.e. the process is preferably performed with a ratio of (hetero)aryl 1,3-dipole compound to (hetero)cycloalkyne in the range of 10 to 1, more preferably in the range of 5 to 1, even more preferably in the range of 2 to 1. In another embodiment, when one of the reagents is present in excess, it is preferred that the (hetero)cycloalkyne is present in excess, i.e. the process is preferably performed with a ratio of (hetero) cycloalkyne to (hetero)aryl 1,3-dipole compound in the range of 10 to 1, more preferably in the range of 5 to 1, even more preferably in the range of 2 to 1. Most preferably the process is performed with a stoichiometry of reagents close to 1:1.

(Hetero)Aryl 1,3-Dipole Compound

A (hetero)aryl 1,3-dipole compound is herein defined as a compound comprising a 1,3-dipole functional group, wherein the 1,3-dipole functional group is bonded to a (hetero)aryl group. More precisely, a (hetero)aryl 1,3-dipole compound is a compound comprising a 1,3-dipole functional group, wherein the 1,3-dipole functional group is bonded to an atom that is part of the (hetero)aromatic ring system of said (hetero)aryl group. Preferably the 1,3-dipole functional group is bonded to a C-atom of the (hetero) aromatic ring system.

The (hetero)aryl group of the (hetero)aryl 1,3-dipole compound:
 (i) comprises one or more substituents having a positive value for the para-Hammett substituent constant $\sigma_p$ and/or the meta-Hammett substituent constant $\sigma_m$, and/ or
 (ii) is an electron-poor (hetero)aryl group, wherein an electron-poor (hetero)aryl group is:
   (ii-a) a (hetero)aryl group wherein the (hetero)aromatic ring system is bearing a positive charge, and/or
   (ii-b) a (hetero)aryl group wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring.

When the (hetero)aryl group comprises one or more substituents having a positive value for the para-Hammett substituent constant $\sigma_p$ and/or the meta-Hammett substituent constant $\sigma_m$, these substituents are bonded to an atom that is part of the (hetero)aromatic ring system of said (hetero)aryl group.

The term "(hetero)aryl group" herein refers to aryl groups as well as heteroaryl groups. The term "(hetero)aryl group" herein refers to monocyclic (hetero)aryl groups, and to bicyclic (hetero)aryl groups.

The (hetero)aryl groups are optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, amino groups, oxo and silyl groups, wherein the silyl groups can be represented by the formula $(R^{Si})_3Si-$, wherein $R^{Si}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more heteroatoms selected from the group consisting of O, N and S.

If the (hetero)aryl groups are optionally substituted with one or more substituents, it is preferred that the substituents are independently selected from the group consisting of $C_1$-$C_{12}$ alkyl groups, amino groups, oxo and silyl groups, wherein the silyl groups are as defined above, and wherein the alkyl groups are optionally interrupted by one of more hetero-atoms selected from the group consisting of O, N and S.

These substituents are optional, and may be present in addition to any substituents as defined above under (i), i.e. substituents having a positive value for the para-Hammett substituent constant $\sigma_p$ and/or the meta-Hammett substituent constant $\sigma_m$, that may also be present on the (hetero)aryl group.

In a preferred embodiment of the process according to the invention, the (hetero)aryl group in the (hetero)aryl 1,3-dipole compound is selected from the group consisting of phenyl groups, naphthyl groups, anthracyl groups, pyrrolyl groups, pyrrolium groups, furanyl groups, thiophenyl groups, pyrazolyl groups, imidazolyl groups, isoxazolyl groups, oxazolyl groups, oxazolium groups, isothiazolyl groups, thiazolyl groups, 1,2,3-triazolyl groups, 1,3,4-triazolyl groups, diazolyl groups, 1-oxa-2,3-diazolyl groups, 1-oxa-2,4-diazolyl groups, 1-oxa-2,5-diazolyl groups, 1-oxa-3,4-diazolyl groups, 1-thia-2,3-diazolyl groups, 1-thia-2,4-diazolyl groups, 1-thia-2,5-diazolyl groups, 1-thia-3,4-diazolyl groups, tetrazolyl groups, pyridinyl groups, pyridazinyl groups, pyrimidinyl groups, pyrazinyl groups, pyradizinyl groups, pyridiniumyl groups, pyrimidinium groups, benzofuranyl groups, benzothiophenyl groups, benzimidazolyl groups, indazolyl groups, benzotriazolyl groups, pyrrolo[2,3-b]pyridinyl groups, pyrrolo[2,3-c]pyridinyl groups, pyrrolo[3,2-c]pyridinyl groups, pyrrolo[3,2-b]pyridinyl groups, imidazo[4,5-b]pyridinyl groups, imidazo[4,5-c]pyridinyl groups, pyrazolo[4,3-d]pyridinyl groups, pyrazolo[4,3-c]pyridinyl groups, pyrazolo[3,4-c]pyridinyl groups, pyrazolo[3,4-b]pyridinyl groups, isoindolyl groups, indazolyl groups, purinyl groups, indolininyl groups, imidazo[1,2-a]pyridinyl groups, imidazo[1,5-a] pyridinyl groups, pyrazolo[1,5-a]pyridinyl groups, pyrrolo [1,2-b]pyridazinyl groups, imidazo[1,2-c]pyrimidinyl groups, quinolinyl groups, isoquinolinyl groups, cinnolinyl groups, quinazolinyl groups, quinoxalinyl groups, phthalazinyl groups, 1,6-naphthyridinyl groups, 1,7-naphthyridinyl groups, 1,8-naphthyridinyl groups, 1,5-naphthyridinyl groups, 2,6-naphthyridinyl groups, 2,7-naphthyridinyl groups, pyrido[3,2-d]pyrimidinyl groups, pyrido[4,3-d]pyrimidinyl groups, pyrido[3,4-d]pyrimidinyl groups, pyrido [2,3-d]pyrimidinyl groups, pyrido[2,3-b]pyrazinyl groups, pyrido[3,4-b]pyrazinyl groups, pyrimido[5,4-d]pyrimidinyl groups, pyrazino[2,3-b]pyrazinyl groups and pyrimido[4,5-d]pyrimidinyl groups, all groups optionally substituted with one or more substituents as defined above.

In a further preferred embodiment, the (hetero)aryl group is selected from the group consisting of phenyl groups, pyridinyl groups, pyridiniumyl groups, pyrimidinyl groups, pyrimidinium groups, pyrazinyl groups, pyradizinyl groups, pyrrolyl groups, pyrrolium groups, furanyl groups, thiophenyl groups, diazolyl groups, quinolinyl groups, imidazolyl groups, oxazolyl groups and oxazolium groups, more preferably from the group consisting of phenyl groups, pyridinyl groups, pyridiniumyl groups, pyrimidinyl groups, pyrimidinium groups pyrrolyl groups, furanyl groups and thiophenyl groups, all groups optionally substituted with one or more substituents as defined above.

Most preferably, the (hetero)aryl group is selected from the group consisting of phenyl groups, pyridinyl groups and pyridiniumyl groups, all groups optionally substituted with one or more substituents as defined above.

The term "1,3-dipole functional group" herein refers to a group comprising a three-atom π-electron system containing four electrons delocalized over the three atoms. 1,3-Dipole compounds, i.e. compounds comprising a 1,3-dipole functional group, are well known in the art. In a preferred embodiment of the process according to the invention, the (hetero)aryl 1,3-dipole compound is selected from the group consisting of a (hetero)aryl nitrone, a (hetero)aryl azide, a (hetero)aryl diazo compound, a (hetero)aryl nitrile oxide, a (hetero)aryl nitronate, a (hetero)aryl nitrile imine, a (hetero)aryl sydnone, a (hetero)aryl sulfon hydrazide, a (hetero)aryl pyridine oxide, a (hetero)aryl oxadiazole 1-oxide, a (hetero)aryl dipole resulting from deprotonation of an alkylated pyridinium compound, a (hetero)aryl [1,2,3]triazol-8-ium-1-ide, a (hetero)aryl 1,2,3-oxadiazol-3-ium-5-olate and a (hetero)aryl 5-oxopyrazolidin-2-ium-1-ide.

In a further preferred embodiment of the process according to the invention, the (hetero)aryl 1,3-dipole compound is selected from the group consisting of a (hetero)aryl nitrone, a (hetero)aryl azide, a (hetero)aryl diazo compound, a (hetero)aryl nitrile oxide, a (hetero)aryl nitronate, a (hetero)aryl nitrile imine, a (hetero)aryl sydnone, a (hetero)aryl sulfon hydrazide, a (hetero)aryl pyridine oxide and a (hetero)aryl oxadiazole 1-oxide, more preferably from the group consisting of a (hetero)aryl nitrone, a (hetero)aryl azide, a (hetero)aryl diazo compound and a (hetero)aryl nitrile oxide, and even more preferably from the group consisting of a (hetero)aryl nitrone, a (hetero)aryl azide and a (hetero)aryl nitrile oxide. In another further preferred embodiment of the process according to the invention, the (hetero)aryl 1,3-dipole compound is a (hetero)aryl azide or a (hetero)aryl diazo compound. Most preferably, the (hetero)aryl 1,3-dipole compound is a (hetero)aryl azide.

As described above, in the process according to the invention:
  (i) the (hetero)aryl group of the (hetero)aryl 1,3-dipole compound comprises one or more substituents having a positive value for the para-Hammett substituent constant $\sigma_p$ and/or the meta-Hammett substituent constant $\sigma_m$, and/or
  (ii) the (hetero)aryl group of the (hetero)aryl 1,3-dipole compound is an electron-poor (hetero)aryl group, wherein an electron-poor (hetero)aryl group is:
    (ii-a) a (hetero)aryl group wherein the (hetero)aromatic ring system is bearing a positive charge, and/or
    (ii-b) a (hetero)aryl group wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring.

An electron-poor (hetero)aryl group herein refers to a (hetero)aryl group wherein the (hetero)aromatic ring system is bearing a positive charge, and/or wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring. Said ratio is a measure for the electronic properties of a (hetero)aryl group, as is known to a person skilled in the art, and is described in more detail in e.g. "Organic Chemistry", T. W. Graham Solomons and Craig B. Fryhle, 7th ed., John Wiley & Sons, Inc., NY 1999 (ISBN 0-471-19095-0), incorporated by reference herein. Said ratio is herein also referred to as the $\text{ratio}_{(pi/proton)}$. As known to a person skilled in the art, "pi" may also be referred to as "π", and thus "$\text{ratio}_{(pi/proton)}$" may also be referred to as "$\text{ratio}_{(\pi/proton)}$".

The $\text{ratio}_{(\pi/proton)}$ refers to the total number of π-electrons that is present in the (hetero)aromatic ring system, divided by the total number of protons that is present in the nuclei that form the (hetero)aromatic ring system that the 1,3-dipole functional group is bonded to.

The number of π-electrons present in the (hetero)aromatic ring system herein refers to the total number of π-electrons that is present in the π-electron system of the (hetero)aromatic ring system of the (hetero)aryl 1,3-dipole compound. When the (hetero)aryl group comprises a bicyclic aromatic ring system, the total number of π-electrons that is present in the π-electron system of both rings of the aromatic ring system is to be taken into account.

The number of protons present in the nuclei of the (hetero)aromatic ring system refers to the total number of protons that is present in the nuclei that form the (hetero)aromatic ring system of the (hetero)aryl 1,3-dipole compound. For example, the number of protons in a carbon nucleus is 6, in a nitrogen nucleus 7, in an oxygen nucleus 8 and in a sulfur nucleus 16. When the (hetero)aryl group comprises a bicyclic aromatic ring system, the total number of π-electrons that is present in the nuclei of both rings of the aromatic system is to be taken into account.

The $\text{ratio}_{(\pi/proton)}$ of benzene is taken as a reference value for 6-membered aromatic systems. Benzene has a $\text{ratio}_{(\pi/proton)}$ of 0.167, since there are 6 π-electrons in the benzene π-electron system, and the 6 carbon nuclei of the benzene ring have a total of 36 protons (i.e. 6 protons for each carbon atom). When a (hetero)aryl group has a $\text{ratio}_{(\pi/proton)}$ that is higher than that of benzene, that (hetero)aryl group is considered to be an electron-rich (hetero)aryl group. When a (hetero)aryl group has a $\text{ratio}_{(\pi/proton)}$ that is lower than that of benzene, i.e. lower than 0.167, that (hetero)aryl group is considered to be an electron-poor (hetero)aryl group.

The $\text{ratio}_{(\pi/proton)}$ of cyclopentadienyl anion is taken as a reference value for 5-membered aromatic systems. A cyclopentadienyl anion has a $\text{ratio}_{(\pi/proton)}$ of 0.2, since there are 6 π-electrons in the cyclopentadienyl anion π-electron system, and the 5 carbon nuclei of the cyclopentadienyl ring have a total of 30 protons (i.e. 6 protons for each carbon atom). When a (hetero)aryl group has a $\text{ratio}_{(\pi/proton)}$ that is higher than that of a cyclopentadienyl anion, that (hetero)aryl group is considered to be an electron-rich (hetero)aryl group. When a (hetero)aryl group has a $\text{ratio}_{(\pi/proton)}$ that is lower than that of a cyclopentadienyl anion, i.e. lower than 0.2, that (hetero)aryl group is considered to be an electron-poor (hetero)aryl group.

In Table 1, the π-electrons present in the (hetero)aromatic ring system, the number of protons present in the (hetero)aromatic ring system nuclei, and the ratio thereof is tabulated. As can be seen from Table 1, pyridinyl, pyridinium, pyrimidin and quinolinyl are examples of electron-poor (hetero)aryl groups.

TABLE 1

π-Electrons, number of protons and $\text{ratio}_{(\pi/proton)}$ of several (hetero)aryl groups.

| Entry | (Hetero)aryl group | Number of π-electrons[1] | Number of Protons[2] | $\text{Ratio}_{(\pi/proton)}$[3] |
|---|---|---|---|---|
| 1 | Phenyl (reference) | 6 | 36 (6 × 6) | 0.167 |
| 2 | Pyridinyl | 6 | 37 (5 × 6 + 7) | 0.162 |
| 3 | Pyridinium | 6 | 37 (5 × 6 + 7) | 0.162 |

TABLE 1-continued

π-Electrons, number of protons and ratio$_{(\pi/proton)}$ of several (hetero)aryl groups.

| Entry | (Hetero)aryl group | Number of π-electrons[1] | Number of Protons[2] | Ratio$_{(\pi/proton)}$[3] |
|---|---|---|---|---|
| 4 | Pyrimidine | 6 | 38 (4 × 6 + 2 × 7) | 0.158 |
| 5 | Quinolinyl | 10 | 61 (9 × 6 + 7) | 0.164 |
| 6 | Cyclopentadienyl anion (reference) | 6 | 30 (5 × 6) | 0.200 |
| 7 | Furanyl | 6 | 32 (4 × 6 + 8) | 0.186 |
| 8 | Pyrrolyl | 6 | 31 (4 × 6 + 7) | 0.194 |
| 9 | Benzofuranyl | 10 | 56 (8 × 6 + 8) | 0.178 |

[1] The total number of pi-electrons that is present in the (hetero)aromatic ring system that the 1,3-dipole functional group is bonded to.
[2] The total number of protons that is present in the nuclei that form the (hetero)aromatic ring system of the (hetero)aromatic 1,3-dipole compound.
[3] The total number of pi-electrons that is present in the (hetero)aromatic ring system, divided by the total number of protons that is present in the nuclei that form the (hetero)aromatic ring system that the 1,3-dipole functional group is bonded to.

A (hetero)aryl group that bears a positive charge herein refers to a (hetero)aryl group wherein the (hetero)aromatic ring of the (hetero)aryl group bears a positive charge. Examples of a (hetero)aryl group bearing a positive charge include a pyridiniumyl group, a pyrimidinyl group, a quinoliniumyl group, an imidazoliniumyl group, a pyrazoliniumyl group, an oxazoliniumyl group, an isoxazoliniumyl group, an azathiazolinium group.

It should be noted that, when the (hetero)aryl group of the (hetero)aryl 1,3-dipole compound is an electron-poor (hetero)aryl group as defined above, said (hetero)aryl group may also comprise one or more substituents having a positive value for the para-Hammett substituent constant $\sigma_p$ and/or the meta-Hammett substituent constant $\sigma_m$.

When the (hetero)aromatic ring of the (hetero)aryl 1,3-dipole compound is a 6-membered ring, does not bear a positive charge and has a ratio$_{(\pi/proton)}$ as defined above that is 0.167 or higher, i.e. when the (hetero)aryl group is phenyl or an electron-rich (hetero)aryl group, then the (hetero)aryl group of the (hetero)aryl 1,3-dipole compound comprises, in addition to the 1,3-dipole functional group, one or more substituents having a positive value for the para-Hammett substituent constant $\sigma_p$ and/or the meta-Hammett substituent constant $\sigma_m$. Said one or more substituents are bonded to an atom that is part of the (hetero)aromatic ring.

When the (hetero)aromatic ring of the (hetero)aryl 1,3-dipole compound is a 5-membered ring, does not bear a positive charge and has a ratio$_{(\pi/proton)}$ as defined above that is 0.200 or higher, i.e. when the (hetero)aryl group is cyclopentadienyl or an electron-rich (hetero)aryl group, then the (hetero)aryl group of the (hetero)aryl 1,3-dipole compound comprises, in addition to the 1,3-dipole functional group, one or more substituents having a positive value for the para-Hammett substituent constant $\sigma_p$ and/or the meta-Hammett substituent constant $\sigma_m$. Said one or more substituents are bonded to an atom that is part of the (hetero) aromatic ring.

When the (hetero)aryl group of the (hetero)aryl 1,3-dipole compound is a 6-membered ring, bears a positive charge, and/or has a ratio$_{(\pi/proton)}$ that is lower than 0.167, i.e. when the (hetero)aryl group is an electron-poor (hetero)aryl group, then the (hetero)aryl group of the (hetero)aryl 1,3-dipole compound may optionally comprise, in addition to the 1,3-dipole functional group, one or more substituents having a positive value for the para-Hammett substituent constant $\sigma_p$ and/or the meta-Hammett substituent constant $\sigma_m$. Said one or more substituents are bonded to an atom that is part of the (hetero)aromatic ring.

When the (hetero)aryl group of the (hetero)aryl 1,3-dipole compound is a 5-membered ring, bears a positive charge, and/or has a ratio$_{(\pi/proton)}$ that is lower than 0.200, i.e. when the (hetero)aryl group is an electron-poor (hetero)aryl group, then the (hetero)aryl group of the (hetero)aryl 1,3-dipole compound may optionally comprise, in addition to the 1,3-dipole functional group, one or more substituents having a positive value for the para-Hammett substituent constant $\sigma_p$ and/or the meta-Hammett substituent constant $\sigma_m$. Said one or more substituents are bonded to an atom that is part of the (hetero)aromatic ring.

In a preferred embodiment of the process according to the invention, the (hetero)aryl group of the (hetero)aryl 1,3-dipole compound is an electron-poor (hetero)aryl group, and said (hetero)aryl group does not comprise, in addition to the 1,3-dipole functional group, any substituents having a positive value for $\sigma_p$ and/or $\sigma_m$. In this embodiment it is further preferred that the (hetero)aryl group is selected from the group consisting of pyridinyl groups, pyridiniumyl groups, pyrimidinyl groups and quinolinyl groups.

In another preferred embodiment of the process according to the invention, the (hetero)aryl group of the (hetero)aryl 1,3-dipole compound is an electron-poor (hetero)aryl group, phenyl or an electron-rich (hetero)aryl group, and said (hetero)aryl group comprises, in addition to the 1,3-dipole functional group, one or more substituents having a positive value for $\sigma_p$ and/or $\sigma_m$. In this embodiment, the (hetero)aryl group may be any (hetero)aryl group. (Hetero)aryl groups and preferred (hetero)aryl groups are defined above.

The electron-poor (hetero)aryl groups, phenyl groups and electron-rich (hetero)aryl groups may additionally be substituted with one or more of the substituents that were defined above for (hetero)aryl groups.

Substituents having a having a positive value for the para-Hammett substituent constant $\sigma_p$ and/or the meta-Hammett substituent constant $\sigma_m$, and preferred embodiments thereof, are described in more detail below.

Preferably, both the para-Hammett substituent constant $\sigma_p$ and the meta-Hammett substituent constant am of a substituent have a positive value. However, when a substituent has a meta-Hammett substituent constant am that is positive, but a para-Hammett substituent constant $\sigma_p$ that is 0.0 or less, than it is preferred that said substituent is on the meta-position relative to the position of the 1,3-dipole functional group. This is the case when the substituent is for example —OH ($\sigma_m$ is 0.12 and $\sigma_p$ is –0.37), —OMe ($\sigma_m$ is 0.12 and $\sigma_p$ is –0.27), —O(C$_6$H$_5$) ($\sigma_m$ is 0.25 and $\sigma_p$ is –0.03) or —OSiMe$_3$ ($\sigma_m$ is 0.13 and $\sigma_p$, is –0.27).

A substituent has a positive value for $\sigma_p$ and/or $\sigma_m$ when the value of $\sigma_m$ and/or $\sigma_m$ is larger than 0.00. In a preferred embodiment, the value for $\sigma_p$ and/or $\sigma_m$ is about 0.03 or larger, preferably about 0.05 or larger, more preferably about 0.07 or larger, even more preferably about 0.10 or larger, yet even more preferably about 0.15 or larger and most preferably about 0.20 or larger.

As is well known in the art, the Hammett substituent constant 6 is a measure for the substituent effect of a functional group. Since the magnitude of the substituent effect depends upon the position of the substituent on the aromatic ring, there are different substituent constants σ for para, meta, and ortho substituents: $\sigma_p$, $\sigma_m$ and $\sigma_o$, respectively. When the Hammett substituent constant has a positive value, the functional group is considered an electron-withdrawing substituent, whereas a functional group having a negative value for the Hammett substituent constant is considered an electron-donating substituent. Generally, the ortho Hammett substituent constant is less used, since steric effects of substituents present on the ortho position may interfere with the electronic effects.

Hammett σ constants are based upon the acid dissociation of benzoic acid and meta- and para-substituted benzoic acids in water at 25° C. The Hammett substituent constant σ is determined as follows:

$$\sigma = \log K/K_0$$

wherein $K_0$ is the acid dissociation constant for the ionization of benzoic acid, and K is the acid dissociation constant for the ionization of a substituted benzoic acid with a given substituent at a given position on the aromatic ring. For the determination of $\sigma_p$ for a given substituent, K is the acid dissociation constant for the ionization of a substituted benzoic acid with said substituent at the para position on the aromatic ring, and for the determination of $\sigma_m$ for a given substituent, K is the acid dissociation constant for the ionization of a substituted benzoic acid with said substituent at the meta position on the aromatic ring.

By definition, the Hammett substituent constants are determined relative to hydrogen, and as a consequence, hydrogen has a Hammett substituent constant σ of 0.0.

Groups with a positive value for $\sigma_p$ and/or $\sigma_m$ include for example F, Cl, Br, I, $NO_2$, CN and many others. Para-Hammett substituent constants $\sigma_p$ and meta-Hammett substituent constants $\sigma_m$ are known for a large number of substituents (see for example C. Hansch et al., *Chem. Rev.* 1991, 91, 165-195, incorporated by reference). Table 1 of Hansch et al., *Chem. Rev.* 1991, 91, p. 168-175, disclosing the meta- and para-Hammett substituent constants $\sigma_m$ and $\sigma_p$ for a large number of functional groups, is expressly incorporated by reference herein.

As was described above, the (hetero)aryl group in a (hetero)aryl 1,3-dipole compound is herein considered an electron-poor (hetero)aryl group, when:

(ii-a) the (hetero)aromatic ring system of the (hetero)aryl group is bearing a positive charge, and/or (ii-b) the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring.

As was described above, when the (hetero)aryl group does not fulfil the requirements for an electron-poor (hetero)aromatic ring, i.e. when the (hetero)aryl group is an electron-rich (hetero)aromatic ring, then the (hetero)aryl group comprises one or more substituents having a positive value for $\sigma_p$ and/or $\sigma_m$.

However, when the (hetero)aryl group does fulfil the requirements for an electron-poor (hetero)aromatic ring, then the (hetero)aryl group may optionally comprise one or more substituents having a positive value for $\sigma_p$ and/or $\sigma_m$.

When the (hetero)aryl group of the (hetero)aryl 1,3-dipole compound comprises, in addition to the 1,3-dipole functional group, one or more substituents having a positive value for the para-Hammett substituent constant $\sigma_p$ and/or the meta-Hammett substituent constant $\sigma_m$, in a preferred embodiment the one or more substituents are independently selected from the group consisting of —$XR^{11}$, halogen (—F, —Cl, —Br, —I, more preferably —F, —Cl, —Br), $C_1$-$C_{12}$ haloalkyl (preferably $C_1$-$C_{12}$ chloroalkyl or $C_1$-$C_{12}$ fluoroalkyl, e.g. —$CF_3$, —$C_2F_5$, —$CCl_3$, —$C_2Cl_5$), —CN, —NC, —$NO_2$, —NCO, —OCN, —NCS, —SCN, —$N^+(R^{11})_3$—C(X)N($R^{11})_2$, —C(X)$R^{11}$, —C(X)X$R^{11}$, —S(O)$R^{11}$, —S(O)$_2R^{11}$, —S(O)O$R^{11}$, —S(O)$_2$O$R^{11}$, —S(O)N($R^{11})_2$, —S(O)$_2$N($R^{11})_2$, —OS(O)$_2R^{11}$, —OS(O)O$R^{11}$, —OS(O)$_2$O$R^{11}$, —P(O)($R^{11}$)(O$R^{11}$), —P(O)(O$R^{11})_2$, —OP(O)(O$R^{11})_2$, —XC(X)$R^{11}$, —XC(X)X$R^{11}$, —XC(X)N($R^{11})_2$, wherein X is oxygen or sulphur and wherein $R^{11}$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O and N. In a further preferred embodiment, X is oxygen. In another preferred embodiment, $R^{11}$ is independently selected from the group consisting of hydrogen, halogen, $C_1$-$C_{12}$ alkyl groups, $C_3$-$C_{12}$ cycloalkyl groups, $C_2$-$C_{12}$ (hetero)aryl groups, $C_3$-$C_{12}$ alkyl(hetero)aryl groups and $C_3$-$C_{12}$ (hetero)arylalkyl groups, the $C_1$-$C_6$ alkyl groups, $C_3$-$C_6$ cycloalkyl groups, $C_2$-$C_{12}$ (hetero)aryl groups, $C_3$-$C_{12}$ alkyl(hetero)aryl groups and $C_3$-$C_{12}$ (hetero)arylalkyl groups optionally substituted and optionally interrupted by one or more heteroatoms selected from O, S and N. In a further preferred embodiment, $R^{11}$ is independently selected from the group consisting of hydrogen, halogen and $C_1$-$C_6$ alkyl groups, more preferably from the group consisting of hydrogen, halogen and $C_1$-$C_4$ alkyl groups. Most preferably, $R^{11}$ is independently selected from the group consisting of hydrogen, methyl, ethyl, propyl, i-propyl, butyl and t-butyl.

More preferably, the (hetero)aryl group of the (hetero)aryl 1,3-dipole compound comprises, in addition to the 1,3-dipole functional group, one or more substituents independently selected from the group consisting of —$XR^{11}$, halogen (—F, —Cl, —Br, —I, more preferably —F, —Cl), $C_1$-$C_6$ haloalkyl (preferably $C_1$-$C_6$ chloroalkyl or $C_1$-$C_6$ fluoroalkyl, e.g. —$CF_3$, —$C_2F_5$, —$CCl_3$, —$C_2Cl_5$), —CN, —NC, —$NO_2$, —NCO, —OCN, —NCS, —SCN, —$N^+(R^{11})_3$, —C(X)N($R^{11})_2$, —C(X)$R^{11}$, —C(X)X$R^{11}$, —S(O)$R^{11}$, —S(O)$_2R^{11}$, —S(O)O$R^{11}$, —S(O)$_2$O$R^{11}$, —S(O)N($R^{11})_2$, —S(O)$_2$N($R^{11})_2$, —OS(O)$_2R^{11}$, —OS(O)O$R^{11}$, —OS(O)$_2$O$R^{11}$, —P(O)($R^{11}$)(O$R^{11}$), —P(O)(O$R^{11})_2$, —OP(O)(O$R^{11})_2$, —XC(X)$R^{11}$, —XC(X)X$R^{11}$, —XC(X)N($R^{11})_2$, wherein X and $R^{11}$, and the preferred embodiments of X and $R^{11}$, are as defined above.

More preferably, the (hetero)aryl group of the (hetero)aryl 1,3-dipole compound comprises, in addition to the 1,3-dipole functional group, one or more substituents independently selected from the group consisting of —$OR^{11}$, halogen (—F, —Cl, —Br, —I, more preferably —F, —Cl, —I), $C_1$-$C_6$ haloalkyl (preferably $C_1$-$C_6$ chloroalkyl or $C_1$-$C_6$ fluoroalkyl, e.g. —$CF_3$, —$C_2F_5$, —$CCl_3$, —$C_2Cl_5$), —CN, —NC, —$NO_2$, —NCO, —OCN, —NCS, —SCN, —$N^+(R^{11})_3$, —C(O)N($R^{11})_2$, —C(O)$R^{11}$, —C(O)X$R^{11}$, —S(O)$R^{11}$, —S(O)$_2R_{11}$, —S(O)O$R^{11}$, —S(O)$_2$O$R^{11}$, —S(O)N($R^{11})_2$, —S(O)$_2$N($R^{11})_2$, —OS(O)$_2R^{11}$, —OC(O)$R^{11}$, —OC(O)O$R^{11}$, —OC(O)N($R^{11})_2$, wherein $R^{11}$, and the preferred embodiments of $R^{11}$, are as defined above.

Even more preferably, the (hetero)aryl group of the (hetero)aryl 1,3-dipole compound comprises, in addition to the 1,3-dipole functional group, one or more substituents independently selected from the group consisting of O$R^{11}$, halogen (preferably —F, —Cl), —$NO_2$, —CN, —$N^+(R^{11})_3$, —C(O)$R^{11}$, —C(O)O$R^{11}$, —C(O)N($R^{11})_2$, —S(O)$R^{11}$ and —S(O)$_2R^{11}$, wherein $R^{11}$ and preferred embodiments of $R^{11}$ are as defined above.

Most preferably, the (hetero)aryl group of the (hetero)aryl 1,3-dipole compound comprises, in addition to the 1,3-dipole functional group, one or more substituents independently selected from the group consisting of O$R^{11}$, halogen (preferably —F, —Cl), —$NO_2$, —CN, —N+($R^{11})_3$, —C(O)

$R^{11}$, —C(O)O$R^{11}$, —C(O)N($R^{11}$)$_2$, —S(O)$R^{11}$ and —S(O)$_2R^{11}$, wherein $R^{11}$ is hydrogen or a $C_1$-$C_{12}$ alkyl group.

When the (hetero)aryl group of the (hetero)aryl 1,3-dipole compound is an electron-poor (hetero)aryl group, as defined above, the (hetero)aryl group of the (hetero)aryl 1,3-dipole compound optionally comprises, in addition to the 1,3-dipole functional group, one or more substituents as defined above.

The (hetero)aryl group may further comprise additional substituents. These optional additional substituents are preferably independently selected from the group consisting of (L')$_t$-(A')$_u$ as defined below, $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, amino groups and silyl groups, wherein the silyl groups can be represented by the formula ($R^{Si}$)$_3$Si—, wherein $R^{Si}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more heteroatoms selected from the group consisting of O, N and S.

If the (hetero)aryl groups are optionally substituted with one or more substituents, it is preferred that the substituents are independently selected from the group consisting of $C_1$-$C_{12}$ alkyl groups, amino groups and silyl groups, wherein the silyl groups are as defined above, and wherein the alkyl groups are optionally interrupted by one or more heteroatoms selected from the group consisting of O, N and S.

In another preferred embodiment of the process according to the invention, the (hetero)aryl group of the (hetero)aryl 1,3-dipole compound is an electron-poor (hetero)aryl group, and said (hetero)aryl group comprises, in addition to the 1,3-dipole functional group, one or more substituents having a positive value for the para-Hammett substituent constant $\sigma_p$ and/or the meta-Hammett substituent constant $\sigma_m$. Substituents having a positive value for the para-Hammett substituent constant $\sigma_p$ and/or the meta-Hammett substituent constant $\sigma_m$, and preferred embodiments thereof, are as defined above.

In another preferred embodiment of the process according to the invention, the (hetero)aryl group of the (hetero)aryl 1,3-dipole compound is an electron-poor (hetero)aryl group, and said (hetero)aryl group does not comprise, in addition to the 1,3-dipole functional group, one or more substituents having a positive value for $\sigma_p$ and/or $\sigma_m$.

In a preferred embodiment of the process according to the invention, the (hetero)aryl 1,3-dipole compound is according to Formula (2):

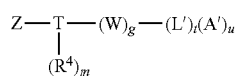

(2)

wherein:
t is 0 or 1;
u is 1-4;
g is 0 or 1;
m is 0-8;

with the proviso that when m is 0, then T is an electron-poor (hetero)aryl group, wherein an electron-poor (hetero)aryl group is as defined above;
Z is a 1,3-dipole functional group;
L' is a linker;
A' is independently selected from the group consisting of D, E and Q, wherein D, E and Q are as defined below;
T is a (hetero)aryl group;
$R^4$ is independently selected from the group consisting of electron-withdrawing substituents having a positive value for the para-Hammett substituent constant $\sigma_p$ and/or the meta-Hammett substituent constant $\sigma_m$; and
W is selected from the group consisting of $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl (hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N.

As described above, when m is 0, then T is an electron-poor (hetero)aryl group, wherein an electron-poor (hetero)aryl group is as defined above. In other words, m may only be 0 when the (hetero)aryl group T is an electron-poor (hetero)aryl group (i.e. a (hetero)aryl group having a ratio$_{(\pi/proton)}$ lower than 0.167 for a 6-membered ring, or lower than 0.200 for a 5-membered ring). When the (hetero)aryl group is phenyl (ratio$_{(\pi/proton)}$ 0.167) or an electron-rich (hetero)aryl group (i.e. a (hetero)aryl group having a ratio$_{(\pi/proton)}$ higher than 0.167 for a 6-membered ring, or higher than 0.200 for a 5-membered ring), then m is 1-7.

In a preferred embodiment of the process according to the invention, the (hetero)aryl group of the (hetero)aryl 1,3-dipole compound is an electron-poor (hetero)aryl group and m is 0, i.e. said (hetero)aryl group does not comprise, in addition to the 1,3-dipole functional group, one or more substituents $R^4$ having a positive value for the para-Hammett substituent constant $\sigma_p$ and/or the meta-Hammett substituent constant $\sigma_m$.

In another preferred embodiment of the process according to the invention, the (hetero)aryl group of the (hetero)aryl 1,3-dipole compound is an electron-poor (hetero)aryl group, and m is 1-7, i.e. said (hetero)aryl group comprises, in addition to the 1,3-dipole functional group, one or more substituents $R^4$ having a having a positive value for the para-Hammett substituent constant $\sigma_p$ and/or the meta-Hammett substituent constant $\sigma_m$.

In another preferred embodiment of the process according to the invention, the (hetero)aryl group of the (hetero)aryl 1,3-dipole compound is phenyl or an electron-rich (hetero)aryl group and m is 1-7, i.e. the (hetero)aryl group comprises, in addition to the 1,3-dipole functional group, one or more substituents having a positive value for the para-Hammett substituent constant $\sigma_p$ and/or the meta-Hammett substituent constant $\sigma_m$.

Substituents having a having a positive value for the para-Hammett substituent constant $\sigma_p$ and/or the meta-Hammett substituent constant $\sigma_m$, and preferred embodiments thereof, are described in more detail above and below.

T is a (hetero)aryl group. (Hetero)aryl groups are described in more detail above. In a preferred embodiment, T is selected from the group consisting of phenyl groups, naphthyl groups, anthracyl groups, pyrrolyl groups, pyrrolium groups, furanyl groups, thiophenyl groups, pyrazolyl groups, imidazolyl groups, isoxazolyl groups, oxazolyl groups, oxazolium groups, isothiazolyl groups, thiazolyl groups, 1,2,3-triazolyl groups, 1,3,4-triazolyl groups, diazolyl groups, 1-oxa-2,3-diazolyl groups, 1-oxa-2,4-diazolyl groups, 1-oxa-2,5-diazolyl groups, 1-oxa-3,4-diazolyl groups, 1-thia-2,3-diazolyl groups, 1-thia-2,4-diazolyl groups, 1-thia-2,5-diazolyl groups, 1-thia-3,4-diazolyl groups, tetrazolyl groups, pyridinyl groups, pyridazinyl groups, pyrimidinyl groups, pyrazinyl groups, pyradizinyl groups, pyridiniumyl groups, pyrimidinium groups, benzofuranyl groups, benzothiophenyl groups, benzimidazolyl groups, indazolyl groups, benzotriazolyl groups, pyrrolo[2,3-b]pyridinyl groups, pyrrolo[2,3-c]pyridinyl groups, pyrrolo[3,2-c]pyridinyl groups, pyrrolo[3,2-b]pyridinyl groups, imidazo[4,5-b]pyridinyl groups, imidazo[4,5-c]pyridinyl groups, pyrazolo[4,3-d]pyridinyl groups, pyrazolo[4,3-c]pyridinyl groups, pyrazolo[3,4-c]pyridinyl groups, pyrazolo[3,4-b]pyridinyl groups, isoindolyl groups, indazolyl groups, purinyl groups, indolininyl groups, imidazo[1,2-a]pyridinyl groups, imidazo[1,5-a]pyridinyl groups, pyrazolo[1,5-a]pyridinyl groups, pyrrolo[1,2-b]pyridazinyl groups, imidazo[1,2-c]pyrimidinyl groups, quinolinyl groups, isoquinolinyl groups, cinnolinyl groups, quinazolinyl groups, quinoxalinyl groups, phthalazinyl groups, 1,6-naphthyridinyl groups, 1,7-naphthyridinyl groups, 1,8-naphthyridinyl groups, 1,5-naphthyridinyl groups, 2,6-naphthyridinyl groups, 2,7-naphthyridinyl groups, pyrido[3,2-d]pyrimidinyl groups, pyrido[4,3-d]pyrimidinyl groups, pyrido[3,4-d]pyrimidinyl groups, pyrido[2,3-d]pyrimidinyl groups, pyrido[2,3-b]pyrazinyl groups, pyrido[3,4-b]pyrazinyl groups, pyrimido[5,4-d]pyrimidinyl groups, pyrazino[2,3-b]pyrazinyl groups and pyrimido[4,5-d]pyrimidinyl groups, said groups optionally substituted with $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, amino groups and silyl groups, wherein the silyl groups can be represented by the formula $(R^{Si})_3Si—$, wherein $R^{Si}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S.

If the (hetero)aryl groups are optionally substituted with one or more substituents, it is preferred that the substituents are independently selected from the group consisting of $C_1$-$C_{12}$ alkyl groups, amino groups and silyl groups, wherein the silyl groups are as defined above, and wherein the alkyl groups are optionally interrupted by one of more hetero-atoms selected from the group consisting of O, N and S.

In a further preferred embodiment, T is selected from the group consisting of phenyl groups, pyridinyl groups, pyridiniumyl groups, pyrimidinyl groups, pyrimidinium groups, pyrazinyl groups, pyradizinyl groups, pyrrolyl groups, pyrrolium groups, furanyl groups, thiophenyl groups, diazolyl groups, quinolinyl groups, imidazolyl groups, oxazolyl groups and oxazolium groups, said groups optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, amino groups and silyl groups, wherein the silyl groups can be represented by the formula $(R^{Si})_3Si—$, wherein $R^{Si}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S.

Z is a 1,3-dipole functional group. In a preferred embodiment of the process according to the invention, Z is selected from the group consisting of a nitrone group, an azide group, a diazo group, a nitrile oxide group, a nitronate group, a nitrile imine group, a sydnone group, a sulfon hydrazide group, a pyridine oxide group, an oxadiazole 1-oxide group, a 1,3-dipole functional group resulting from deprotonation of an alkylated pyridinium compound, a [1,2,3]triazol-8-ium-1-ide group, a 1,2,3-oxadiazol-3-ium-5-olate group and a 5-oxopyrazolidin-2-ium-1-ide group.

More preferably, Z is selected from the group consisting of a nitrone group, an azide group, a diazo group, a nitrile oxide group, a nitronate group, a nitrile imine group, a sydnone group, a sulfon hydrazide group, a pyridine oxide group and a oxadiazole 1-oxide group, more preferably from the group consisting of a nitrone group, an azide group, a diazo group and a nitrile oxide group, and even more preferably from the group consisting of a nitrone group, an azide group and a nitrile oxide group. In another further preferred embodiment of the process according to the invention, Z is an azide group or a diazo group. Most preferably, Z is an azide group.

$R^4$, if present, is independently selected from the group consisting of electron-withdrawing substituents having a positive value for the para-Hammett substituent constant $\sigma_p$ and/or the meta-Hammett substituent constant $\sigma_m$. The Hammett constants $\sigma_p$ and $\sigma_m$ are described in more detail above.

In a preferred embodiment, $R^4$ is independently selected from the group consisting of —$XR^{11}$, halogen (—F, —Cl, —Br, —I, more preferably —F, —Cl, —Br), $C_1$-$C_{12}$ haloalkyl (preferably $C_1$-$C_{12}$ chloroalkyl or $C_1$-$C_{12}$ fluoroalkyl, e.g. —$CF_3$, —$C_2F_5$, —$CCl_3$, —$C_2Cl_5$), —CN, —NC, —$NO_2$, —NCO, —OCN, —NCS, —SCN, —N+$(R^{11})_3$, —C(X)N$(R^{11})_2$, —C(X)$R^{11}$, —C(X)X$R^{11}$, —S(O)$R^{11}$, —S(O)$_2R^{11}$, —S(O)O$R^{11}$, —S(O)$_2$O$R^{11}$, —S(O)N$(R^{11})_2$, —S(O)$_2$N$(R^{11})_2$—OS(O)$_2R^{11}$, —OS(O)O$R^{11}$, —OS(O)$_2$O$R^{11}$, —P(O)$(R^{11})(OR^{11})$, —P(O)$(OR^{11})_2$, —OP(O)$(OR^{11})_2$, —XC(X)$R^{11}$, —XC(X)X$R^{11}$, —XC(X)N$(R^{11})_2$, wherein X is is oxygen or sulphur and wherein $R^1$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O and N. In a further preferred embodiment, X is oxygen. In another preferred embodiment, $R^{11}$ is independently selected from the group consisting of hydrogen, halogen, $C_1$-$C_{12}$ alkyl groups, $C_3$-$C_{12}$ cycloalkyl groups, $C_2$-$C_{12}$ (hetero)aryl groups, $C_3$-$C_{12}$ alkyl(hetero)aryl groups and $C_3$-$C_{12}$ (hetero) arylalkyl groups, the $C_1$-$C_6$ alkyl groups, $C_3$-$C_6$ cycloalkyl groups, $C_2$-$C_{12}$ (hetero)aryl groups, $C_3$-$C_{12}$ alkyl(hetero)aryl groups and $C_3$-$C_{12}$ (hetero)arylalkyl groups optionally substituted and optionally interrupted by one or more heteroatoms selected from O and N. In a further preferred embodiment, $R^{11}$ is independently selected from the group consisting of hydrogen, halogen and $C_1$-$C_6$ alkyl groups, more preferably from the group consisting of hydrogen, halogen and $C_1$-$C_4$ alkyl groups. Most preferably, $R^{11}$ is independently selected from the group consisting of hydrogen, methyl, ethyl, propyl, i-propyl, butyl and t-butyl.

More preferably, $R^4$ is independently selected from the group consisting of —$XR^{11}$, halogen (—F, —Cl, —Br, —I, more preferably —F, —Cl, —I), $C_1$-$C_6$ haloalkyl (preferably $C_1$-$C_6$ chloroalkyl or $C_1$-$C_6$ fluoroalkyl, e.g. —$CF_3$, —$C_2F_5$, —$CCl_3$, —$C_2Cl_5$), —CN, —NC, —$NO_2$, —NCO, —OCN, —NCS, —SCN, —$N^+(R^{11})_3$, —$C(X)N(R^{11})_2$, —$C(X)R^{11}$, —$C(X)XR^{11}$, —$S(O)R^{11}$, —$S(O)_2R^{11}$, —$S(O)OR^{11}$, —$S(O)_2OR^{11}$, —$S(O)N(R^{11})_2$, —$S(O)_2N(R^{11})_2$, —$OS(O)_2R^{11}$, —$OS(O)OR^{11}$, —$OS(O)_2OR^{11}$, —$P(O)(R^{11})(OR^{11})$, —$P(O)(OR^{11})_2$, —$OP(O)(OR^{11})_2$, —$XC(X)R^{11}$, —$XC(X)XR^{11}$, —$XC(X)N(R^{11})_2$, wherein X and $R^{11}$, and the preferred embodiments of X and $R^{11}$, are as defined above. Even more preferably, $R^4$ is independently selected from the group consisting of —$OR^{11}$ (preferably —OMe), halogen (preferably —F, —Cl), —$NO_2$, —CN, —$N+(R^{11})_3$, —$C(O)R^{11}$, —$C(O)OR^{11}$, —$S(O)R^{11}$ and —$S(O)_2R^{11}$, wherein $R^{11}$ and preferred embodiments of $R^{11}$ are as defined above.

The (hetero)aryl group T may comprise up to 8 substituents $R^4$ (m is 0-8).

It should be noted, as described above, that m may only be 0 when T is an electron-poor (hetero)aryl group, wherein an electron-poor (hetero)aryl group is as defined above.

When T is phenyl or when T is an electron-rich (hetero) aryl group, wherein an electron-rich (hetero)aryl group as defined above, then m is 1, 2, 3, 4, 5, 6, 7 or 8, preferably, m is 1, 2, 3, 4, 5 or 6, more preferably m is 1, 2, 3 or 4, and most preferably m is 1 or 2.

When T is an electron-poor (hetero)aryl group, T may optionally further comprise one or more substituents $R^4$, i.e. in this case m is 0, 1, 2, 3, 4, 5, 6, 7 or 8. Preferably, m is 0, 1, 2, 3, 4, 5 or 6, more preferably m is 0, 1, 2, 3 or 4, and most preferably m is 0, 1 or 2.

W, if present, is preferably selected from the group consisting of $C_1$-$C_{12}$ alkylene groups, $C_2$-$C_{12}$ alkenylene groups, $C_3$-$C_{12}$ cycloalkylene groups, $C_2$-$C_{12}$ (hetero) arylene groups, $C_3$-$C_{12}$ alkyl(hetero)arylene groups and $C_3$-$C_{12}$ (hetero)arylalkylene groups, wherein the alkylene groups, alkenylene groups, cycloalkylene groups, (hetero) arylene groups, alkyl(hetero)arylene groups and (hetero) arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N. More preferably, W, if present, is selected from the group consisting of $C_1$-$C_{12}$ alkylene groups, $C_2$-$C_{12}$ (hetero)arylene groups and $C_3$-$C_{12}$ alkyl (hetero)arylene groups, wherein alkylene groups, (hetero) arylene groups and alkyl(hetero)arylene groups are optionally substituted, and wherein the alkylene groups, (hetero) arylene groups and alkyl(hetero)arylene groups are optionally are optionally interrupted by one or more heteroatoms selected from the group consisting of O, S and N. Even more preferably W, if present, is a $C_1$-$C_6$ alkylene group, optionally substituted and optionally interrupted by one or more heteroatoms selected from the group consisting of O, S and N. Most preferably W, if present, is a methylene group, an ethylene group, a propylene group or a butylene group.

A' is independently selected from the group consisting of D, E and Q, wherein D is a molecule of interest, E is a solid surface and Q is a functional group. Molecules of interest D, solid surfaces E and functional groups Q are described in more detail below.

In the process according to the invention, A' is selected independently from A that is present in the (hetero)cycloalkyne. In the (hetero)cycloalkyne, A is also defined as a molecule of interest D, a solid surface E or a functional group E. However, since A and A' are selected independently, A' in the (hetero)aryl 1,3-dipole compound according to Formula (2), and preferred embodiments thereof, may be different from A in the (hetero)cycloalkyne according to Formula (2), and preferred embodiments thereof.

A molecule of interest D may for example be a reporter molecule, a diagnostic compound, an active substance, an enzyme, an amino acid (including an unnatural amino acid), a (non-catalytic) protein, a peptide, a polypeptide, an oligonucleotide, a monosaccharide, an oligosaccharide, a polysaccharide, a glycan, a (poly)ethylene glycol diamine (e.g. 1,8-diamino-3,6-dioxaoctane or equivalents comprising longer ethylene glycol chains), a polyethylene glycol chain, a polyethylene oxide chain, a polypropylene glycol chain, a polypropylene oxide chain or a 1,x-diaminoalkane (wherein x is the number of carbon atoms in the alkane).

An active substance is a pharmacological and/or biological substance, i.e. a substance that is biologically and/or pharmaceutically active, for example a drug or a prodrug, a diagnostic agent, an amino acid, a protein, a peptide, a polypeptide, a glycan, a lipid, a vitamin, a steroid, a nucleotide, a nucleoside, a polynucleotide, RNA or DNA. Examples of suitable peptide tags include a cell-penetrating peptide like human lactoferrin or polyarginine. An example of a suitable glycan is oligomannose. Preferably, the active substance is selected from the group consisting of drugs and prodrugs. More preferably, the active substance is selected from the group consisting of pharmaceutically active compounds, in particular low to medium molecular weight compounds (e.g. about 200 to about 1500 Da, preferably about 300 to about 1000 Da), such as for example cytotoxins, antiviral agents, antibacterials agents, peptides and oligonucleotides. Examples of cytotoxins include camptothecins, doxorubicin, daunorubicin, taxanes, calicheamycins, duocarmycins, maytansines, auristatins or pyrrolobenzodiazepines (PBDs). Additional examples of cytotoxins include colchicine, *vinca* alkaloids, tubulysins, irinotecans, an inhibitory peptide, amanitin, deBouganin. In a preferred embodiment, the cytotoxin is selected from the group consisting of camptothecins, doxorubicin, daunorubicin, taxanes, calicheamycins, duocarmycins, maytansines, auristatins and pyrrolobenzodiazepines (PBDs). In another preferred embodiment, the cytotoxin is selected from the group consisting of colchicine, *vinca* alkaloids, tubulysins, irinotecans, an inhibitory peptide, amanitin and deBouganin.

A reporter molecule is a molecule whose presence is readily detected, for example a diagnostic agent, a dye, a fluorophore, a radioactive isotope label, a contrast agent, a magnetic resonance imaging agent or a mass label. Examples of a fluorophore include all kinds of Alexa Fluor (e.g. Alexa Fluor 555), cyanine dyes (e.g. Cy3 or Cy5), coumarin derivatives, fluorescein, rhodamine, allophycocyanin and chromomycin.

Examples of radioactive isotope label include $^{99m}$Tc, $^{111}$In, $^{18}$F, $^{14}$C, $^{64}$Cu, $^{131}$I or $^{123}$I, which may or may not be connected via a chelating moiety such as DTPA, DOTA, NOTA or HYNIC.

A solid surface E is for example a functional surface (e.g. nanomaterials, carbon nanotubes, fullerenes, virus capsids), metal surface (e.g. gold, silver, copper, nickel, tin, rhodium, zinc) or a metal alloy surface (from aluminium, bismuth, chromium, cobalt, copper, gallium, gold, indium, iron, lead, magnesium, mercury, nickel, potassium, plutonium, rhodium, scandium, silver, sodium, titanium, tin, uranium, zinc, zirconium), a polymer surface (e.g. polystyrene, polyvinylchloride, polyethylene, polypropylene, poly(dimethylsiloxane), polymethylmethacrylate), where E is preferably independently selected from the group consisting of a functional surface or a polymer surface.

A functional group Q is preferably independently selected from the group consisting of hydrogen, halogen, $R^{11}$, —CH=C($R^{11}$)$_2$, —C≡C$R^{11}$, —[C($R^{11}$)$_2$C($R^{11}$)$_2$O]$_q$—$R^{11}$ wherein q is in the range of 1 to 200, —CN, —N$_3$, —NCX, —XCN, —X$R^{11}$, —N($R^{11}$)$_2$, —$^+$N($R^{11}$)$_3$, —C(X)N($R^{11}$)$_2$, —C($R^{11}$)$_2$X$R^{11}$, —C(X)$R^{11}$, —C(X)X$R^{11}$, —S(O)$R^{11}$, —S(O)$_2$$R^{11}$, —S(O)O$R^{11}$, —S(O)$_2$O$R^{11}$, —S(O)N($R^1$)$_2$, —S(O)$_2$N($R^{11}$)$_2$—OS(O)$R^{11}$, —OS(O)$_2$$R^{11}$, —OS(O)O$R^{11}$, —OS(O)$_2$O$R^{11}$, —P(O)($R^{11}$)(O$R^{11}$), —P(O)(O$R^{11}$)$_2$, —OP(O)(O$R^{11}$)$_2$, —Si($R^{11}$)$_3$, —XC(X)$R^{11}$, —XC(X)X$R^{11}$, —XC(X)N($R^{11}$)$_2$, —N($R^{11}$)C(X)$R^{11}$, —N($R^{11}$)C(X)X$R^{11}$ and —N($R^{11}$)C(X)N($R^{11}$)$_2$, wherein X is oxygen or sulphur and wherein $R^{11}$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O and N.

Preferably $R^{11}$ is independently selected from the group consisting of hydrogen, halogen and $C_1$-$C_6$ alkyl groups, more preferably from the group consisting of hydrogen, halogen and $C_1$-$C_4$ alkyl groups. Most preferably, $R^{11}$ is independently selected from the group consisting of hydrogen, methyl, ethyl, propyl, i-propyl, butyl and t-butyl. X is preferably oxygen.

Optionally, functional group Q is masked or protected. More preferably, Q is independently selected from the group consisting of —CN, —NCX, —XCN, —X$R^{11}$, —N($R^{11}$)$_2$, —$^+$N($R^{11}$)$_3$, —C(X)N($R^{11}$)$_2$, —C($R^{11}$)$_2$X$R^{11}$, —C(X)$R^{11}$, —C(X)X$R^{11}$, —XC(X)$R^{11}$, —XC(X)X$R^{11}$, —XC(X)N($R^{11}$)$_2$, —N($R^{11}$)C(X)$R^{11}$, —N($R^{11}$)C(X)X$R^{11}$ and —N($R^{11}$)C(X)N($R^{11}$)$_2$, wherein X and $R^{11}$, and preferred embodiments of X and $R^{11}$, are as defined above. Most preferably, Q is selected from the group consisting of —O$R^{11}$, —S$R^{11}$, —N($R^{11}$)$_2$, —$^+$N($R^{11}$)$_3$, —C(O)N($R^{11}$)$_2$, —C(O)O$R^{11}$, —OC(O)$R^{11}$, —OC(O)O$R^{11}$, —OC(O)N($R^{11}$)$_2$, —N($R^{11}$)C(O)$R^{11}$, —N($R^{11}$)C(O)O$R^{11}$ and —N($R^{11}$)C(O)N($R^{11}$)$_2$, wherein X and $R^{11}$, and preferred embodiments of X and $R^{11}$, are as defined above.

In a preferred embodiment of the process according to the invention, A' is a molecule of interest D. More preferably, A' is independently selected from the group consisting of a reporter molecule, an active substance, an enzyme, a protein, a glycoprotein, an antibody, a peptide, a polypeptide, an oligonucleotide, a monosaccharide, an oligosaccharide, a polysaccharide, a glycan, a diagnostic compound, an amino acid, a (poly)ethylene glycol diamine, a polyethylene glycol chain, a polyethylene oxide chain, a polypropylene glycol chain, a polypropylene oxide chain and a 1,x-diaminoalkane (wherein x is the number of carbon atoms in the alkane). Reporter molecules and active substances are described in more detail above.

In a particularly preferred embodiment, A' is a glycoprotein, preferably an antibody. When A' is a glycoprotein, it is preferred that the (hetero)aryl group of the (hetero)aryl 1,3-dipole compound is bonded to the glycoprotein via a saccharide moiety of the glycoprotein glycan.

In another particularly preferred embodiment, A' is a saccharide moiety. The saccharide moiety may be a monosaccharide moiety, an oligosaccharide moiety or a polysaccharide moiety. The monosaccharide moiety, oligosaccharide moiety or polysaccharide moiety is optionally substituted, for example with a nucleotide. The nucleotide is preferably selected from the group consisting of a nucleoside monophosphate and a nucleoside diphosphate, more preferably from the group consisting of uridine diphosphate (UDP), guanosine diphosphate (GDP), thymidine diphosphate (TDP), cytidine diphosphate (CDP) and cytidine monophosphate (CMP), more preferably from the group consisting of uridine diphosphate (UDP), guanosine diphosphate (GDP), cytidine diphosphate and (CDP). Most preferably, the nucleotide is UDP.

Throughout this description, the claims and the drawings, when the nucleotide is UDP, i.e. when -Nuc is -UDP, the nucleotide has the structure shown below.

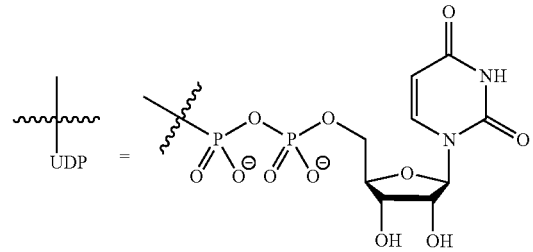

Preferably, the saccharide moiety is a monosaccharide moiety, more preferably a saccharide moiety selected from the group consisting of galactose (Gal), mannose (Man), N-acetylglucosamine (GlcNAc), glucose (Glc), N-acetylgalactosamine (GalNAc), fucose (Fuc) and N-acetylneuraminic acid (sialic acid Sia or NeuNAc), even more preferably from the group consisting of GlcNAc, Glc, Gal and GalNAc, yet even more preferably from Gal or GalNAc. Most preferably, the monosaccharide moiety is GalNAc. The nucleotide is preferably bonded to C1 of the monosaccharide moiety, and the (hetero)aryl group is preferably bonded via the N-acetyl group of the GalNAc moiety.

Preferred embodiments of the (hetero)aryl 1,3-dipole compound wherein A' is a glycoprotein, e.g. an antibody, and wherein A' is a saccharide moiety are described in more detail below.

When t is 1, the (hetero)aryl group of the (hetero)aryl 1,3-dipole compound is bonded to A' via L'. L' is a linker, herein also referred to as linking unit. Said (hetero)aryl group may be bonded to one or to more A' via linker L' (u is 1, 2, 3 or 4). When more than one A' is present (u is 2, 3 or 4), each A' is independently selected, in other words each A' may be different from the others. Preferably, u is 1 or 2 and most preferably u is 1.

Linker L' is selected independently from linker L that is present in the (hetero)cycloalkyne. In other words, linker L' in the (hetero)aryl 1,3-dipole compound according to Formula (2), and preferred embodiments thereof, may be different from linker L in the (hetero)cycloalkyne according to Formula (1), and preferred embodiments thereof.

Linkers are well known in the art. L' and L' may for example be independently selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups, $C_9$-$C_{200}$ arylalkynylene groups. Optionally the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are substituted, and optionally said groups are interrupted by one or more heteroatoms, preferably 1 to 100 heteroatoms, said heteroatoms preferably being selected from the group consisting of O, S and N.

In a preferred embodiment of the process according to the invention, the (hetero)aryl 1,3-dipole compound is according to Formula (3a), (3b), (3c), (3d), (3e) or (3f):

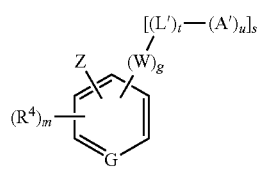
3a

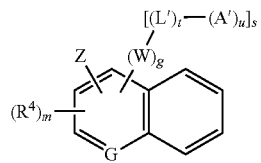
3b

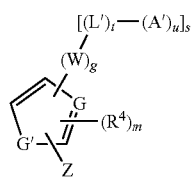
3c

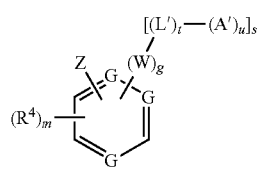
3d

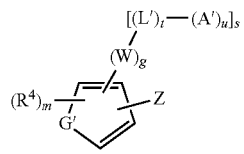
3e

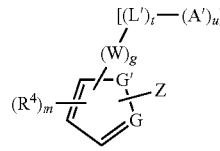
3f wherein:
Z, L', A', $R^4$, W, g, m, t and u, and preferred embodiments thereof, are as defined above;
s is 0 or 1;
G is independently selected from the group consisting of N, CH, $CR^4$, $CR^5$, C—$(W)_g$-$[(L')_t$-$(A')_u]$, $N^+R^5$ and $N^+$—$(W)_g$-$[(L')_t$-$(A')_u]$, wherein $R^5$ is selected from the group consisting of $C_1$-$C_{24}$ alkyl groups;
G' is independently selected from the group consisting of O, S, $NR^{12}$, and $N^+(R^{12})_2$ wherein $R^{12}$ is independently selected from the group consisting of hydrogen, $R^4$, $R^5$ and $(W)_g$-$[(L')_t$-$(A')_u]$; and
with the proviso that when s is 0, G is C—$(W)_g$-$[(L')_t$-$(A')_u]$ or $N^+$—$(W)_g$-$[(L')_t$-$(A')_u]$, and G' is N—$(W)_g$-$[(L')_t$-$(A')_u]$ or $N^+(R^{12})$ {—$(W)_g$-$[(L')_t$-$(A')_u]$}.

In (3a), (hetero)aryl group T may e.g. be phenyl, pyridinyl or pyridiniumyl. In (3b), (hetero)aryl group T may e.g. be pyrazinyl, pyradizinyl, pyrimidinyl, pyrimidiniumyl, or triazinyl. In (3c), (hetero)aryl group T may e.g. be quinolinyl. In (3d), (hetero)aryl group T may for example be pyrrolyl, pyrrolium, pyrrolidiniumyl, furanyl or thiophenyl (i.e. thiofuranyl). In (3e), (hetero)aryl group T may for example be diazolyl, oxazolyl, imidazolyl or thiazolyl. In (3f), (hetero)aryl group T may for example be pyrazolyl, an isoxathiazole, or isoxazolyl.

$R^5$ is preferably selected from the group consisting of $C_1$-$C_{12}$ alkyl groups, more preferably from the group consisting of $C_1$-$C_6$ alkyl groups and most preferably from the group consisting of methyl, ethyl propyl, i-propyl, butyl and t-butyl.

Preferred embodiments of Z, L', A', $R^4$, W, g, m, t and u are described in more detail above. These preferred embodiments also apply to (hetero)aryl 1,3-dipole compounds according to Formula (3a), (3b), (3c), (3d), (3e) and (3f).

In a particularly preferred embodiment, the (hetero)aryl 1,3-dipole compound is according to Formula (3t), (3u), (3v), (3w), (3x), (3y) or (3z):

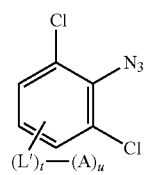
3t

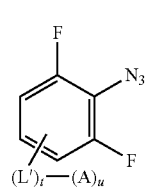
3u

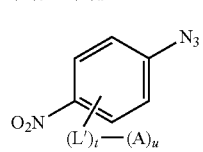
3v

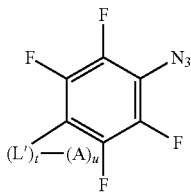
3w

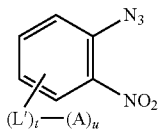
3x

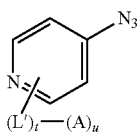
3y

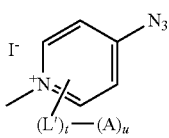
3z

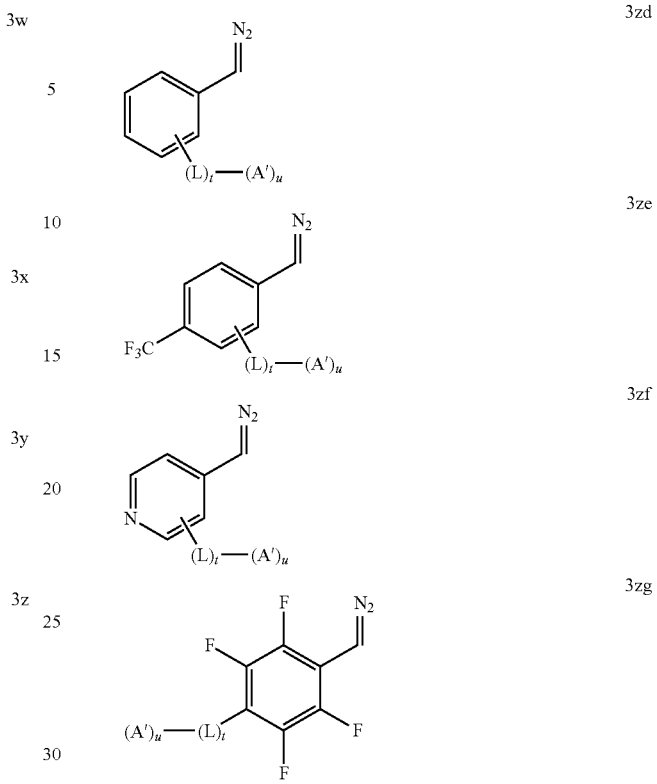

3zd

3ze

3zf

3zg wherein $(L')_t$-$(A)_u$ is as defined above.

In a further preferred embodiment, linker L', if present is an alkylamide, e.g. propylamide.

In another particularly preferred embodiment, the (hetero) aryl 1,3-dipole compound is according to Formula (3za), (3zb) or (3zc):

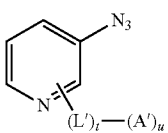
3za

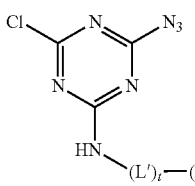
3zb

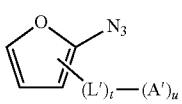
3zc wherein $(L')_t$-$(A')_u$ is as defined above.

In a further preferred embodiment, linker L', if present is an alkylamide, e.g. propylamide.

In another particularly preferred embodiment, the (hetero) aryl 1,3-dipole compound is according to Formula (3zd), (3ze), (3zf) or (3zg):

wherein $(L')_t$-$(A)_u$ is as defined above.

As described above, in a preferred embodiment of the (hetero)aryl 1,3-dipole compound A' is a glycoprotein, preferably an antibody, and in another preferred embodiment A' is an, optionally substituted, saccharide moiety. Also when the (hetero)aryl 1,3-dipole compound is according to Formula (3a), (3b), (3c), (3d), (3e) or (3f), or according to Formula (3t), (3u), (3v), (3w), (3x), (3y) or (3z), or according to Formula (3za), (3zb) or (3zc), or according to Formula (3zd), (3ze), (3zf) or (3zg), it is preferred that A' is a glycoprotein, preferably an antibody, or that A' is an optionally substituted, saccharide moiety.

When A' is an optionally substituted saccharide moiety, in a preferred embodiment of the process according to the invention, the (hetero)aryl 1,3-dipole compound is according to Formula (2b), and when A' is a glycoprotein, in a preferred embodiment the (hetero)aryl 1,3-dipole compound is according to Formula (2c):

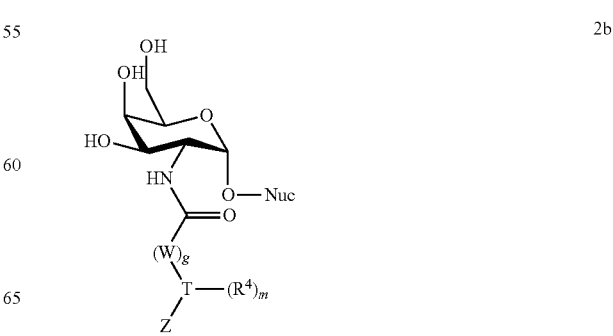
2b

-continued

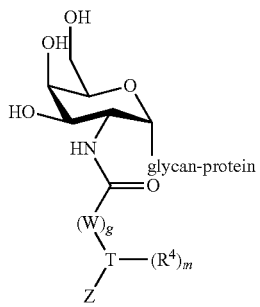
2c wherein:

Nuc, T, W, r, m and R⁴, and preferred embodiments thereof, are as defined above for (2); and Z is an azide group or a diazo group.

In (2b), preferably, Nuc is UDP. In (2b) and (2c), W may be present (g is 1) or absent (g is 0). In a preferred embodiment of (2b) and (2c), g is 0. In another further preferred embodiment of (2b) and (2c), g is 1 and W is selected from the group consisting of methylene, ethylene, propylene (preferably n-propylene), butylene (preferably n-butylene), pentylene (preferably n-pentylene) and hexylene (preferably n-hexylene), more preferably g is 1 and W is selected from the group consisting of methylene, ethylene, propylene (preferably n-propylene) and butylene (preferably n-butylene), even more preferably g is 1 and W is selected from the group consisting of methylene, ethylene and propylene (preferably n-propylene), yet even more preferably g is 1 and W is methylene or ethylene. Most preferably, when g is 1, W is methylene.

When the (hetero)aryl 1,3-dipole compound is according to Formula (2b) or (2c), it is particularly preferred that the (hetero)aryl moiety -T(Z)(R⁴)$_m$ corresponds to the (hetero)aryl moiety as depicted above for (3t), (3u), (3v), (3w), (3x), (3y) or (3z), or as depicted above for (3za), (3zb) or (3zc), or as depicted above for (3zd), (3ze), (3zf) or (3zg). In a further preferred embodiment, g is 0. In another further preferred embodiment, g is 1 and preferred embodiments of W are as described above for (2b) and (2c).

In a particularly preferred embodiment of the process according to the invention, the (hetero)aryl 1,3-dipole compound is according to Formula (2d), (2e), (2f) or (2g):

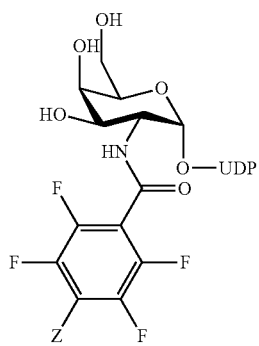
2e

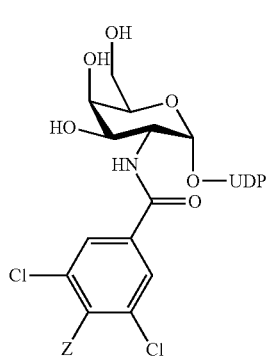
2f

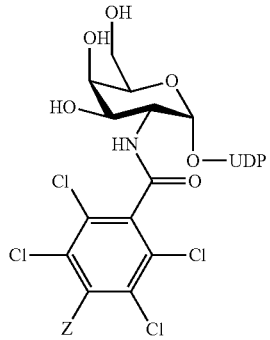
2g wherein Z is an azide group or a diazo group.

In a further preferred embodiment of (2d), (2e), (2f) and (2g), Z is an azide group.

In another particularly preferred embodiment of the process according to the invention, the (hetero)aryl 1,3-dipole compound is according to Formula (2h), (2i), (2j) or (2k):

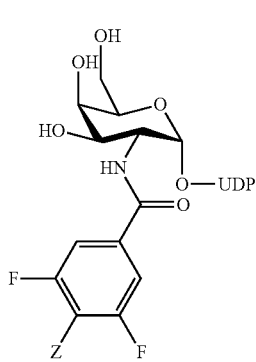
2d

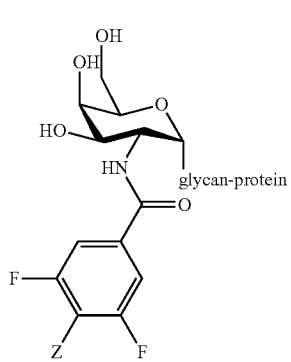
2h

-continued

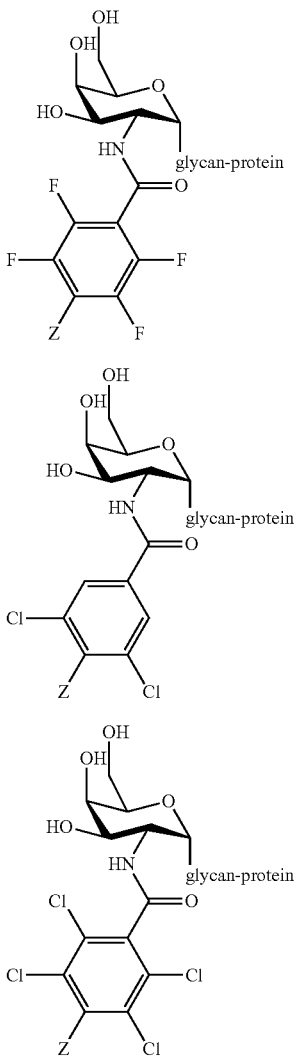

wherein Z is an azide group or a diazo group.

In a further preferred embodiment of (2h), (2i), (2j) and (2k), Z is an azide group.

(Hetero)cycloalkyne

The term "(hetero)cycloalkyne" herein refers to cycloalkynes as well as to heterocycloalkynes.

In the process according to the invention, the (hetero) cycloalkyne is according to Formula (1), wherein a, a', a", n, p, q, r, B, B', L, A and $R^1$ are as defined above.

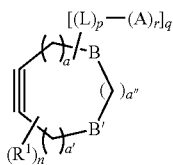

As was described above, a is 0 to 8, a' is 0 to 8 and a" is 0 to 8, with the proviso that a+a'+a" is 4, 5, 6, 7 or 8. As a consequence, the (hetero)cycloalkyne according to Formula (1) is a (hetero)cyclooctyne (a+a'+a" is 4), a (hetero)cyclononyne (a+a'+a" is 5), a (hetero)cyclodecyne (a+a'+a" is 6), a (hetero)cycloundecyne (a+a'+a" is 7) or a (hetero)cyclododecyne (a+a'+a" is 8).

It is particularly preferred that a+a'+a" is 4 or that a+a'+a" is 5, i.e. it is particularly preferred that the (hetero)cycloalkyne is a (hetero)cyclooctyne or a (hetero)cyclononyne, preferably a (hetero)cyclooctyne. Consequently, when the (hetero)cycloalkyne is a (hetero)cyclooctyne, a, a' and a" are independently 0, 1, 2, 3 or 4, with the proviso that a+a'+a" is 4; and when the (hetero)cycloalkyne is a (hetero)cyclononyne, a, a' and a" are independently 0, 1, 2, 3, 4 or 5, with the proviso that a+a'+a" is 5. When the (hetero)cycloalkyne is a (hetero)cyclooctyne, n is 0, 1, 2, 3, 4, 5, 6, 7 or 8 and when the (hetero)cycloalkyne is a (hetero)cyclononyne, n is 0, 1, 2, 3, 4, 5, 6, 7, 8, 9 or 10. Preferably, n is 0, 1, 2, 3, 4, 5 or 6, even more preferably n is 0, 1, 2, 3 or 4 and most preferably n is 0, 1 or 2.

In another particularly preferred embodiment, the (hetero)cycloalkyne is an aliphatic (hetero)cycloalkyne, wherein an aliphatic (hetero)cycloalkyne is defined as a (hetero)cycloalkyne wherein both $sp^1$ C-atoms of the (hetero)cycloalkyne carbon-carbon triple bond are bonded to an $sp^3$ C-atom.

In another particularly preferred embodiment, the aliphatic (hetero)cycloalkyne according to Formula (1) is an aliphatic (hetero)cyclooctyne or an aliphatic (hetero)cyclononyne. When the (hetero)cycloalkyne according to Formula (1) is an aliphatic (hetero)cyclooctyne, a is 1, 2, 3 or 4; a' is 1, 2, 3 or 4; a" is 1, 2, 3 or 4; with the proviso that a+a'+a"=4; and n is 0-8. When the (hetero)cycloalkyne according to Formula (1) is an aliphatic (hetero)cyclononyne, a is 1, 2, 3, 4 or 5; a' is 1, 2, 3, 4 or 5; a" is 1, 2, 3, 4 or 5; with the proviso that a+a'+a"=5; and n is 0-10.

When a is one or more, the one or more C-atoms present between the C≡C triple bond and B are herein also referred to as a-C-atoms. In analogy, when a' is one or more, the one or more C-atoms present between the C≡C triple bond and B' are herein also referred to as a'-C-atoms, and if a" is one or more, the one or more C-atoms present between B and B' are herein also referred to as a"-C-atoms.

In a preferred embodiment, $R^1$ is independently selected from the group consisting of $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N.

When the (hetero)cycloalkyne according to Formula (1) is a (hetero)cyclooctyne n is 0-8, when the (hetero)cycloalkyne is a (hetero)cyclononyne n is 0-10, when the (hetero)cycloalkyne is a (hetero)cyclodecyn n is 0-12, when the (hetero)cycloalkyne is a (hetero)cycloundecyn n is 0-14 and when the (hetero)cycloalkyne is a (hetero)cyclododecyn n is 0-16. Preferably, n is 0, 1, 2, 3, 4, 5, 6, 7 or 8, more preferably n is 0, 1, 2, 3, 4, 5 or 6, even more preferably n is 0, 1, 2, 3 or 4 and most preferably n is 0, 1 or 2.

As described above, if q in (hetero)cycloalkyne (1) is 0, then:

(i) B and/or B' is $NR^3$ wherein $R^3$ is $(L)_p$-$(A)_r$;
(ii) B and/or B' is $C(R^3)_2$ wherein one or more $R^3$ is $(L)_p$-$(A)_r$;

(iii) n is 2 or more and two $R^1$ groups together form a (hetero)cycloalkyl group wherein the (hetero)cycloalkyl group is substituted with an $(L)_p$-$(A)_r$ substituent; and/or (iv) a" is 2 or more and n is 2 or more and two $R^1$ groups present on adjacent a"-C-atoms together form a (hetero)aryl group wherein the (hetero)aryl group is substituted with an $(L)_p$-$(A)_r$ substituent.

When a" is 2 or more, there are 2 or more a"-C-atoms present between B and B'. Optionally, when a" is 2 or more and n is 2 or more, and 2 adjacent a"-C-atoms are substituted with $R^1$, these two $R^1$ groups may together form a (hetero)aryl group, the (hetero)aryl group optionally being substituted with an $(L)_p$-$(A)_r$ substituent. Said (hetero)aryl ring is fused to the (hetero)cycloalkyne ring. In this embodiment, it is preferred that the (hetero)cycloalkyne is according to Formula (1b):

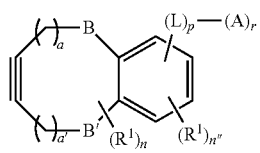

wherein B, B', $R^1$, L, A, a, a', p, r and q are as defined above; with the proviso that a+a' is 2, 3, 4, 5 or 6;
wherein n is 0, 1, 2, 3 or 4; and
n" is 0, 1, 2 or 3.

In this embodiment it is preferred that a+a' is 2 or 3, i.e. it is preferred that the (hetero)cycloalkyne is a (hetero)cyclooctyne or a (hetero)cyclononoctyne. More preferably a+a' is 2, i.e. more preferably the (hetero)cycloalkyne is a (hetero)cyclooctyne.

Optionally, when n is 2 or more, two $R^1$ groups, preferably on adjacent C-atoms, may together form a (hetero)cycloalkyl group, the (hetero)cycloalkyl group optionally being substituted with an $(L)_p$-$(A)_r$ substituent. Preferably, the two $R^1$-groups, preferably on adjacent C-atoms, together form a (hetero)cyclopropyl group, a (hetero)cyclobutyl group, a (hetero)cyclopentyl group or a (hetero)cyclohexyl group, more preferably a (hetero)cyclopropyl group, a (hetero)cyclobutyl group or a (hetero)cyclopentyl group and most preferably a cyclopropyl group, all optionally being substituted with an $(L)_p$-$(A)_r$ substituent. Preferably, the (hetero)cycloalkyl group that is formed by the two $R^1$ groups is fused to the (hetero)cycloalkyne. Therefore it is preferred in this embodiment that a is 2 or more, and/or a' is 2 or more, and/or a" is 2 or more. Alternatively, it is preferred in this embodiment that a is 1 and B is $NR^1$ or $C(R^3)_2$ wherein at least one of $R^3$ is $R^1$, and/or a' is 1 and B' is $NR^1$ or $C(R^3)_2$ wherein at least one of $R^3$ is $R^1$.

In this embodiment, it is preferred that the (hetero)cycloalkyne is according to Formula (1c):

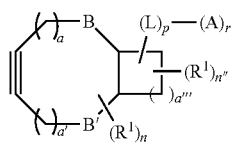

wherein B, B', $R^1$, L, A, a, a', p, r and q are as defined above; with the proviso that a+a' is 2, 3, 4, 5 or 6;

wherein n is 0-6 (preferably 0, 1, 2, 3 or 4);
n" is 0, 1, 2, 3 or 4; and
a'" is 0, 1, 2 or 3.

In this embodiment it is further preferred that a+a' is 2 or 3, i.e. it is preferred that the (hetero)cycloalkyne is a (hetero)cyclooctyne or a (hetero)cyclononyne. More preferably, a+a' is 2, i.e. more preferably the (hetero)cycloalkyne is a (hetero)cyclooctyne. Preferably, a'" is 0 or 1, in other words, the annellated (hetero)cycloalkyl group is an annulated cyclopropyl or an annulated cyclobutyl group, preferably an annulated cyclopropyl group.

When p is 1, then A is bonded to the (hetero)cycloalkyne via L. L is a linker, herein also referred to as linking unit. The (hetero)cycloalkyne may be bonded to one or more A via linker L (r is 1, 2, 3 or 4). When more than one A is present (r is 2, 3 or 4), each A is independently selected, in other words each A may be different from the other(s). Preferably, r is 1 or 2 and most preferably r is 1.

The description of A and preferred embodiments of A corresponds to the description of A' (and A" and A'", if present) and preferred embodiments of A' (and A" and A'", if present). Both A in the (hetero)cycloalkyne and A' (and A" and A'", if present) in the (hetero)aryl 1,3-dipole compound are defined as a molecule of interest D, a solid surface E or a functional group E. Molecules of interest D, solid surfaces E and functional groups Q are described in more detail above. However, since A and A' (and A" and A'", if present) are selected independently, A' (and optionally A" and A'") in the (hetero)aryl 1,3-dipole compound according to Formula (2), and in preferred embodiments thereof, A' (and A" and A'", if present) may be different from A in the (hetero)cycloalkyne according to Formula (1), (1b) or (1c), and preferred embodiments thereof.

In a preferred embodiment of the process according to the invention, A is a molecule of interest D. More preferably, A is independently selected from the group consisting of a reporter molecule, an active substance, an enzyme, a protein, a glycoprotein, an antibody, a peptide, a polypeptide, an oligonucleotide, a glycan, a diagnostic compound, an amino acid, a (poly)ethylene glycol diamine, a polyethylene glycol chain, a polyethylene oxide chain, a polypropylene glycol chain, a polypropylene oxide chain and a 1,x-diaminoalkane (wherein x is the number of carbon atoms in the alkane). Reporter molecules and active substances are described in more detail above.

In another preferred embodiment, A is a molecule of interest D, and D is an active substance. More preferably, the active substance is selected from the group consisting of pharmaceutically active compounds, in particular low to medium molecular weight compounds (e.g. about 200 to about 1500 Da, preferably about 300 to about 1000 Da), such as for example cytotoxins, antiviral agents, antibacterials agents, peptides and oligonucleotides. Examples of cytotoxins include camptothecins, doxorubicin, daunorubicin, taxanes, calicheamycins, duocarmycins, maytansines, auristatins or pyrrolobenzodiazepines (PBDs). Additional examples of cytotoxins include colchicine, vinca alkaloids, tubulysins, irinotecans, an inhibitory peptide, amanitin, deBouganin. In a preferred embodiment, the cytotoxin is selected from the group consisting of camptothecins, doxorubicin, daunorubicin, taxanes, calicheamycins, duocarmycins, maytansines, auristatins and pyrrolobenzodiazepines (PBDs). In another preferred embodiment, the cytotoxin is selected from the group consisting of colchicine, vinca alkaloids, tubulysins, irinotecans, an inhibitory peptide, amanitin and deBouganin.

In another preferred embodiment, when A is a molecule of interest D, D is reporter molecule, for example a diagnostic agent, a dye, a fluorophore, a radioactive isotope label, a contrast agent, a magnetic resonance imaging agent or a mass label. Examples of a fluorophore include all kinds of Alexa Fluor (e.g. Alexa Fluor 555), cyanine dyes (e.g. Cy3 or Cy5), coumarin derivatives, fluorescein, rhodamine, allophycocyanin and chromomycin. Examples of radioactive isotope label include $^{99m}Tc$, $^{111}In$, $^{18}F$, $^{14}C$, $^{64}Cu$, $^{131}I$ Or $^{123}$, which may or may not be connected via a chelating moiety such as DTPA, DOTA, NOTA or HYNIC.

Linker L is selected independently from linker L' (and from L" and L''', if present) that is present in the (hetero)aryl 1,3-dipole compound. In other words, linker L in the (hetero)cycloalkyne according to Formula (1), (1b) or (1c), and preferred embodiments thereof, may be different from linker L in the (hetero)aryl 1,3-dipole compound according to Formula (2), and preferred embodiments thereof.

Linking units are described in more detail above. The description of L and preferred embodiments of L correspond to the description of L' (and L" and L''', if present) and preferred embodiments of L'. However, as described above, L and L' (and L" and L''', if present) are selected independently from one another, and consequently L may differ from L' (and L" and L''', if present) in the process according to the invention.

In a preferred embodiment of the process according to the invention, the (hetero)cycloalkyne is an aliphatic (hetero)cycloalkyne. An aliphatic (hetero)cycloalkyne is herein defined as a (hetero)cycloalkyne wherein both $sp^1$ C-atoms of the (hetero)cycloalkyne carbon-carbon triple bond are bonded to an $sp^3$ C-atom. In other words, an aliphatic (hetero)cycloalkyne herein refers to a (hetero)cycloalkyne wherein the two C-atoms on each side of the carbon-carbon triple bond C≡C are $sp^3$ C-atoms.

In this embodiment, the (hetero)cycloalkyne is thus according to Formula (1), wherein a' and a are independently 1-8. Preferably, a is 1, 2, 3 or 4, more preferably 1 or 2, and/or a' is 1, 2, 3 or 4, more preferably 1 or 2. It is further preferred that a" is 0, 1, 2, 3 or 4, more preferably 1 or 2. It is further preferred that a+a'+a" is 4, i.e. it is preferred that the (hetero)cycloalkyne is a (hetero)cyclooctyne. Even more preferably, a is 1, a' is 1 and a" is 2. In this embodiment, it is further preferred that B is O and B' is O. In a further preferred embodiment, a is 1, a' is 1 and a" is 2, B is O and B' is O, and [(L)$_p$-(A)$_r$] is present on one of the a"-C-atoms. In another further preferred embodiment, a is 1, a' is 1 and a" is 2, B is C(R$^3$)$_2$ and B' is C(R$^3$)$_2$, and [(L)$_p$-(A)$_r$] is present on one of the a"-C-atoms.

In another preferred embodiment, a is 2, a' is 2 and a" is 0, or a is 2, a' is 1 and a" is 1. In this embodiment it is further preferred that B is C(R$^3$)[(L)$_p$-(A)$_r$] and B' is C(R$^3$)$_2$, or that B is N[(L)$_p$-(A)$_r$] and B' is C(R$^3$)$_2$.

In a further preferred embodiment, the (hetero)cycloalkyne is an aliphatic (hetero)cycloalkyne according to Formula (4):

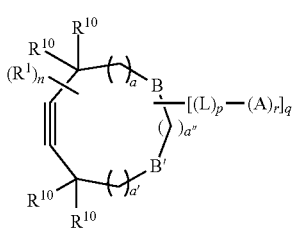

wherein:
a is 0, 1, 2, 3, 4, 5 or 6;
a' is 0, 1, 2, 3, 4, 5 or 6;
a" is 0, 1, 2, 3, 4, 5 or 6;
with the proviso that a+a'+a"=2, 3, 4, 5 or 6;
n is 0-12;
R$^1$ is independently selected from the group consisting of —OR$^2$, —NO$_2$, —CN, —S(O)$_2$R$^2$, C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups, wherein the alkyl groups, cycloalkyl groups, (hetero)aryl groups, alkyl(hetero)aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein R$^2$ is independently selected from the group consisting of hydrogen, halogen, C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups; optionally, when n is 2 or more, two R$^1$ groups may together form a (hetero)cycloalkyl group, the (hetero)cycloalkyl group optionally being substituted with an (L)$_p$-(A)$_r$ substituent;
optionally, when a" is 2 or more and n is 2 or more, two R$^1$ groups present on adjacent a"-C-atoms may together form a (hetero)aryl group, the (hetero)aryl group optionally being substituted with an (L)$_p$-(A)$_r$ substituent;
R$^{10}$ is independently selected from the group consisting of (L)$_p$-(A)$_r$ wherein L, A, p and r are as defined below, hydrogen, C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups, wherein the alkyl groups, cycloalkyl groups, (hetero)aryl groups, alkyl(hetero)aryl groups and (hetero)arylalkyl groups are optionally substituted and wherein the alkyl groups, cycloalkyl groups, alkyl(hetero)aryl groups and (hetero)arylalkyl groups are optionally interrupted by one or more heteroatoms selected from the group consisting of O, S and N;
B and B' are independently selected from the group consisting of O, S, C(O), NR$^3$ and C(R$^3$)$_2$, wherein R$^3$ is independently selected from the group consisting of hydrogen, R$^1$ or (L)$_p$-(A)$_r$;
p is 0 or 1;
r is 1-4;
L is a linker;
A is independently selected from the group consisting of D, E and Q, wherein D, E and Q are as defined below;
q is 0-4;
with the proviso that if q is 0, then B and/or B' is NR$^3$ wherein R$^3$ is (L)$_p$-(A)$_r$, and/or B and/or B' is C(R$^3$)$_2$ wherein one or more R$^3$ is (L)$_p$-(A)$_r$, and/or n is 2 or more and two R$^1$ groups together form a (hetero)cycloalkyl group wherein the (hetero)cycloalkyl group is substituted with an (L)$_p$-(A)$_r$ substituent, and/or a" is 2 or more and n is 2 or more and two R$^1$ groups present on adjacent a"-C-atoms together form a (hetero)aryl group wherein the (hetero)aryl group is substituted with an (L)$_p$-(A)$_r$ substituent, and/or one or more of R$^{10}$ is (L)$_p$-(A)$_r$;
D is a molecule of interest;
E is a solid surface; and
Q is a functional group.

The preferred embodiments for R$^1$, L' and A' as described above for a (hetero)cycloalkyne according to Formula (1) also apply to the preferred embodiments of R$^1$, L and A (hetero)cycloalkyne according to Formula (4). It is further preferred that r is 1 or 2. In the aliphatic (hetero)cycloalkyne according to Formula (4), a+a'+a" is 2, 3, 4, 5 or 5. In a preferred embodiment, a+a'+a" is 2, i.e. the aliphatic (hetero)cycloalkyne is a (hetero)cyclooctyne. In another preferred embodiment, a+a'+a" is 3, i.e. the aliphatic (hetero)cyclononyne.

In one embodiment, it is further preferred that a is 0, a' is 0 and a" is 2. In this embodiment, it is further preferred that B is O and B' is O. In a further preferred embodiment, a is 0, a' is 0 and a" is 2, B is O and B' is O, and even more preferably $[(L)_p-(A)_r]$ is present on one of the a"-C-atoms.

In another further preferred embodiment, a is 0, a' is 0 and a" is 2, B is $C(R^3)_2$ and B' is $C(R^3)_2$, and $[(L)_p-(A)_r]$ is present on one of the a"-C-atoms.

In another preferred embodiment, a is 1, a' is 1 and a" is 0. In this embodiment it is further preferred that B is $C(R^3)[(L)_p-(A)_r]$ and B' is $C(R^3)_2$, or that B is $N[(L)_p-(A)_r]$ and B' is $C(R^3)_2$.

When the (hetero)cycloalkyne according to Formula (4) is a (hetero)cyclooctyne n is 0-4, when the (hetero)cycloalkyne is a (hetero)cyclononyne n is 0-6, when the (hetero)cycloalkyne is a (hetero)cyclodecyn n is 0-8, when the (hetero)cycloalkyne is a (hetero)cycloundecyn n is 0-10 and when the (hetero)cycloalkyne is a (hetero)cyclododecyn n is 0-12. Preferably, n is 0, 1, 2, 3, 4, 5, 6, 7 or 8, more preferably n is 0, 1, 2, 3, 4, 5 or 6, even more preferably n is 0, 1, 2, 3 or 4 and most preferably n is 0, 1 or 2.

As described above, if q in aliphatic (hetero)cycloalkyne (4) is 0, then:

(i) B and/or B' is $NR^3$ wherein $R^3$ is $(L)_p-(A)_r$;
(ii) B and/or B' is $C(R^3)_2$ wherein one or more of $R^3$ is $(L)_p-(A)_r$;
(iii) n is 2 or more and two $R^1$ groups together form a (hetero)cycloalkyl group wherein the (hetero)cycloalkyl group is substituted with an $(L)_p-(A)_r$ substituent;
(iv) a" is 2 or more and n is 2 or more and two $R^1$ groups present on adjacent a"-C-atoms together form a (hetero)aryl group wherein the (hetero)aryl group is substituted with an $(L)_p-(A)_r$ substituent; and/or
(v) one or more of $R^{10}$ is $(L)_p-(A)_r$.

When two $R^1$ groups on adjacent a"-C-atoms optionally form a fused (hetero)aryl group it is preferred that the (hetero)cycloalkyne is according to Formula (4b), and when two $R^1$ groups optionally form a (hetero)cycloalkyl group, it is preferred that the (hetero)cycloalkyne is according to Formula (4c):

wherein B, B', $R^1$, $R^{10}$, L, A, a, a', p, r and q are as defined above for (4); with the proviso that a+a' is 0, 1, 2, 3 or 4; n' is 0, 1, 2, 3 or 4; n" is 0, 1, 2, 3 or 4; and a''' is 0, 1, 2 or 3.

In a preferred embodiment, a+a' is 0, i.e. the (hetero)cycloalkyne is a (hetero)cyclooctyne. In other words, preferably a is 0 and a' is 0. In another preferred embodiment, a+a' is 1, i.e. the (hetero)cycloalkyne is a (hetero)cyclononyne. In (4c), it is further preferred that a''' is 0, 1 or 2, more preferably 0 or 1, most preferably 0. In this embodiment it is thus preferred that a cycloalkyl ring is annulated to the (hetero)cycloalkyne, most preferably a cyclopropyl ring.

The preferred embodiments for $R^1$, L and A as described above for a (hetero)cycloalkyne according to Formula (1) also apply to the preferred embodiments of a, a', a", $R^1$, L and A for a (hetero)cycloalkyne according to Formula (4b) and (4c). It is further preferred that r is 1 or 2.

In a preferred embodiment, the (hetero)cycloalkyne in the process according to the invention is a (hetero)cyclooctyne, i.e. preferably a+a'+a" is 4 in the (hetero)cycloalkyne according to Formula (1), (1b) or (1c). More preferably, a is 1, a' is 1 and a" is 2.

In a further preferred embodiment, the (hetero)cyclooctyne is an aliphatic (hetero)cyclooctyne as defined above. More preferably the aliphatic (hetero)cyclooctyne is an aliphatic (hetero)cyclooctyne according to Formula (4), (4b) or (4c), i.e. more preferably a+a'+a" is 2 in the (hetero)cycloalkyne according to Formula (4), and a+a' is 0 in the (hetero)cycloalkyne according to Formula (4b) or (4c).

In another preferred embodiment, the (hetero)cycloalkyne in the process according to the invention is a (hetero)cyclononyne, i.e. preferably a+a'+a" is 5 in the (hetero)cycloalkyne according to Formula (1), (1b) or (1c).

In a further preferred embodiment, the (hetero)cyclononyne is an aliphatic (hetero)cyclononyne as defined above. More preferably the aliphatic (hetero)cyclononyne is an aliphatic (hetero)cyclononyne according to Formula (4), (4b) or (4c), i.e. more preferably a+a' is 3 in the (hetero)cycloalkyne according to Formula (4), and a+a' is 1 in the (hetero)cycloalkyne according to Formula (4b) or (4c).

In a preferred embodiment of the process according to the invention, the (hetero)cycloalkyne is according to Formula (5):

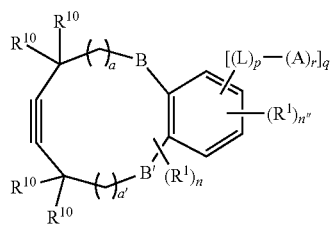

4b

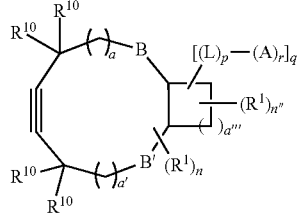

4c

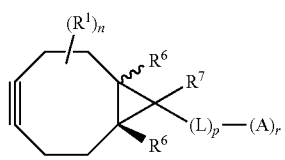

5 wherein:
$R^1$, L, p, r and A and preferred embodiments thereof are as defined above;
n is 0-8;
$R^6$ is independently selected from the group consisting of hydrogen, halogen, $C_1-C_{24}$ alkyl groups, $C_2-C_{24}$ (hetero)aryl groups, $C_3-C_{24}$ alkyl(hetero)aryl groups and $C_3-C_{24}$ (hetero)arylalkyl groups, wherein the alkyl groups, alkyl(hetero)aryl groups and (hetero)arylalkyl groups optionally are independently optionally interrupted by one of more hetero-atoms selected from the group consisting of O, N and S, and wherein the alkyl groups, (hetero)aryl groups, alkyl(hetero)aryl groups and (hetero)arylalkyl groups are independently optionally substituted; and $R^7$ is selected from the group consisting of hydrogen, $(L)_p$-$(A)_r$, halogen, $C_1$-$C_{24}$ alkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkyl(hetero)aryl groups and (hetero)arylalkyl groups optionally are independently optionally interrupted by one of more hetero-atoms selected from the group consisting of O, N and S, and wherein the alkyl groups, (hetero)aryl groups, alkyl(hetero)aryl groups and (hetero)arylalkyl groups are independently optionally substituted.

In a preferred embodiment, n is 0. In another preferred embodiment, $R^6$ is H. In another preferred embodiment, $R^7$ is H. In a further preferred embodiment, n is 0, $R^6$ is H and $R^7$ is H. In another further preferred embodiment, the (hetero)cycloalkyne is according to Formula (6), wherein L, A, p and r are as defined above:

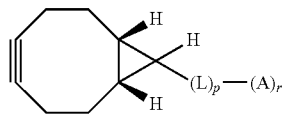

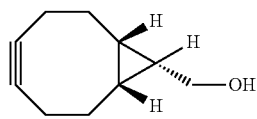

In another preferred embodiment, n is 0, $R^6$ is H, $R^7$ is H and p is 1. More preferably, r is 1 or 2, most preferably r is 1. An example of a (hetero)cycloalkyne according to Formula (6) is (hetero)cycloalkyne (6b), wherein p is 1, L is $CH_2$, r is 1 and A is a functional group Q, namely —OH.

In another preferred embodiment of the process according to the invention, the (hetero)cyclooctyne is according to Formula (7), (8), (9), (10) or (11):

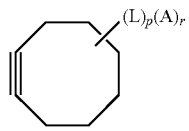

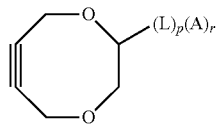

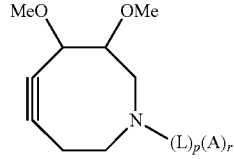

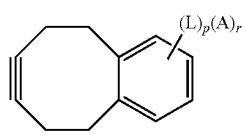

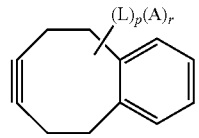

wherein L, p, r and A, as well as preferred embodiments thereof, are as described above.

When the (hetero)cycloalkyne is according to Formula (7), it is preferred that -$(L)_p(A)_r$ is present on C5 of the cyclooctyne.

In another preferred embodiment of the process according to the invention, the (hetero)cycloalkyne is a (hetero)cyclononyne according to Formula (35a) or (35b):

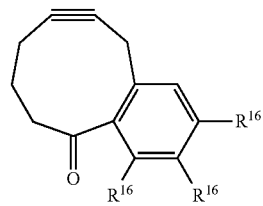

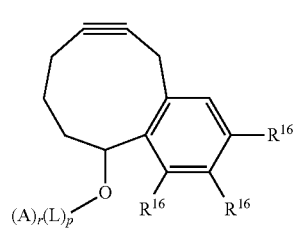

wherein:
L, p, r and A, as well as preferred embodiments thereof, are as described above; and
$R^{16}$ is independently -$(L)_p(A)_r$, H or —OMe.

Cyclononynes (11b) and (11c) are described in *J Org. Chem.*, 2012, 77, 2093, incorporated by reference herein.

Also in a (hetero)cycloalkyne according to Formula (5), (6), (7), (8), (9), (10) and (11), or in a (hetero)cyclononyne according to Formula (35a) or (35b), r is preferably 1 or 2, more preferably 1, and A is preferably selected from the group consisting of a reporter molecule, an active substance, an enzyme, a protein, a glycoprotein, an antibody, a peptide, a polypeptide, an oligonucleotide, a glycan, a diagnostic compound, an amino acid, a (poly)ethylene glycol diamine, a polyethylene glycol chain, a polyethylene oxide chain, a polypropylene glycol chain, a polypropylene oxide chain and a 1,x-diaminoalkane (wherein x is the number of carbon atoms in the alkane). Reporter molecules and active substances are described in more detail above. Further preferred embodiments of A are as described above.

As described above, the invention relates to a process for the cycloaddition of a (hetero)cycloalkyne according to Formula (1) with a (hetero)aryl 1,3-dipole compound with a (hetero)cycloalkyne, wherein (i) the (hetero)aryl group of the (hetero)aryl 1,3-dipole compound is an electron-poor (hetero)aryl group, wherein an electron-poor (hetero)aryl group is as defined above, and/or (ii) the (hetero)aryl group of the (hetero)aryl 1,3-dipole compound comprises one or more substituents having a positive value for the para-Hammett substituent constant $\sigma_p$ and/or the meta-Hammett substituent constant $\sigma_m$.

In a preferred embodiment of the process according to the invention, a (hetero)cycloalkyne according to Formula (1) reacts with a (hetero)aryl 1,3-dipole compound according to Formula (2), or preferred embodiments thereof as described herein.

In another preferred embodiment of the process according to the invention, a (hetero)cycloalkyne according to Formula (1) reacts with a (hetero)aryl 1,3-dipole compound according to Formula (3), or preferred embodiments thereof as described herein.

In a further preferred embodiment of the process according to the invention, an aliphatic (hetero)cycloalkyne, wherein an aliphatic (hetero)cycloalkyne is defined as a (hetero)cycloalkyne wherein both $sp^1$ C-atoms of the (hetero)cycloalkyne carbon-carbon triple bond are bonded to an $sp^3$ C-atom, as described above, reacts with a (hetero)aryl 1,3-dipole compound wherein (i) the (hetero)aryl group of the (hetero)aryl 1,3-dipole compound is an electron-poor (hetero)aryl group, wherein an electron-poor (hetero)aryl group is as defined above, and/or (ii) the (hetero)aryl group of the (hetero)aryl 1,3-dipole compound comprises one or more substituents having a positive value for the para-Hammett substituent constant $\sigma_p$ and/or the meta-Hammett substituent constant $\sigma_m$. In a further preferred embodiment, the aliphatic ((hetero)cycloalkyne is according to Formula (4).

In another preferred embodiment, a (hetero)aryl 1,3-dipole compound according to Formula (2), or preferred embodiments thereof as described herein, reacts with an aliphatic (hetero)cycloalkyne as defined above, more preferably with an aliphatic (hetero)cycloalkyne according to Formula (4), or preferred embodiments thereof as described herein.

In another preferred embodiment, a (hetero)aryl 1,3-dipole compound according to Formula (3), or preferred embodiments thereof as described herein, reacts with an aliphatic (hetero)cycloalkyne as defined above, more preferably with an aliphatic (hetero)cycloalkyne according to Formula (4), or preferred embodiments thereof as described herein.

In another preferred embodiment, a (hetero)cycloalkyne according to Formula (5), (6), (7), (8), (9), (10) or (11), or according to Formula (35a) or (35b), reacts with a (hetero)aryl 1,3-dipole compound wherein (i) the (hetero)aryl group of the (hetero)aryl 1,3-dipole compound is an electron-poor (hetero)aryl group, wherein an electron-poor (hetero)aryl group is as defined above, and/or (ii) the (hetero)aryl group of the (hetero)aryl 1,3-dipole compound comprises one or more substituents having a positive value for the para-Hammett substituent constant $\sigma_p$ and/or the meta-Hammett substituent constant $\sigma_m$.

In another preferred embodiment, a (hetero)cycloalkyne according to Formula (5), (6), (7), (8), (9), (10) or (11), or according to Formula (35a) or (35b), reacts with a (hetero)aryl 1,3-dipole compound according to Formula (2), or preferred embodiments thereof as described herein.

In another preferred embodiment, a (hetero)cycloalkyne according to Formula (5), (6), (7), (8), (9), (10) or (11), or according to Formula (35a) or (35b), reacts with a (hetero)aryl 1,3-dipole compound according to Formula (3), or preferred embodiments thereof as described herein.

In a particularly preferred embodiment of the process according to the invention, in the (hetero)aryl 1,3-dipole compound A' is a glycoprotein, preferably an antibody (as described in more detail above). In an even more preferred embodiment of the process, A' is a glycoprotein, preferably an antibody, and A is a molecule of interest D, preferably a biologically active compound, more preferably A is selected from the group consisting of drugs and prodrugs. Even more preferably, A is selected from the group consisting of pharmaceutically active compounds, in particular low to medium molecular weight compounds (e.g. about 200 to about 1500 Da, preferably about 300 to about 1000 Da), such as for example cytotoxins, antiviral agents, antibacterials agents, peptides and oligonucleotides. Examples of cytotoxins include camptothecins, doxorubicin, daunorubicin, taxanes, calicheamycins, duocarmycins, maytansines, auristatins or pyrrolobenzodiazepines (PBDs). In this embodiment of the process according to the invention, it is particularly preferred that A is a toxin, preferably a toxin selected from the group consisting of camptothecins, doxorubicin, daunorubicin, taxanes, calicheamycins, duocarmycins, maytansines, auristatins and pyrrolobenzodiazepines (PBDs), or a toxin selected from the group consisting of colchicine, *vinca* alkaloids, tubulysins, irinotecans, an inhibitory peptide, amanitin and deBouganin.

Rate Constants $k_{rel}$

One of the advantages of the cycloaddition process according to the invention is that the reaction rate of the reaction of a (heter)aryl 1,3-dipole compound with a (hetero)cycloalkyne may be tailored by the properties of the (hetero)aryl group of the (hetero)aryl 1,3-dipole compound. Said (hetero)aryl group (i) is an electron-poor (hetero)aryl group, and/or (ii) comprises one or more substituents having a positive value for $\sigma_p$ and/or $\sigma_m$ (i.e. comprises one or more electron-withdrawing substituents on the (hetero)aryl group), and this results in (a) a significant reaction rate enhancement of the process according to the invention and (b) a highly selective reaction of the (hetero)aryl 1,3-dipole compound with the (hetero)cycloalkyne according to Formula (1) as compared to aromatic cycloalkynes, e.g. dibenzoannulated cyclooctynes.

These effects are particularly noteworthy when the (hetero)cycloalkyne is an aliphatic (hetero)cycloalkyne, preferably an aliphatic (hetero)cycloalkyne according to Formula (4) and preferred embodiments thereof. (Hetero)cycloalkynes according to Formula (1) and preferred embodiments thereof (e.g. (hetero)cycloalkynes according to Formula (4) and preferred embodiments thereof) are described in more detail above.

In a preferred embodiment of the process according to the invention, the process has a relative rate constant $k_{rel}$ of 1 or more, wherein the relative rate constant $k_{rel}$ is defined as the rate constant of the process according to the invention, i.e. the cycloaddition of a (hetero)cycloalkyne according to Formula (1) with a (hetero)aryl 1,3-dipole compound comprising an electron-poor (hetero)aryl group, and/or comprising one or more substituents having a positive value for $\sigma_p$ and/or $\sigma_m$, divided by the rate constant of the cycloaddition of the same (hetero)cycloalkyne according to Formula (1) with the reference (hetero)aryl 1,3-dipole compound for the process, phenyl azide.

Preferably, the relative rate constant $k_{rel}$ as defined above is 1 or more. In other words, the rate constant of the cycloaddition of a specific (hetero)cycloalkyne with a specific (hetero)aryl 1,3-dipole compound wherein (i) the (hetero)aryl group is an electron-poor (hetero)aryl group, and/or (ii) the (hetero)aryl group of the (hetero)aryl 1,3-dipole compound comprises one or more substituents having a positive value for $\sigma_p$ and/or $\sigma_m$, preferably is equal to or larger than the rate constant of the cycloaddition of the same (hetero)cycloalkyne with the reference (hetero)aryl 1,3-dipole compound for that specific (hetero)aryl 1,3-dipole compound.

In a further preferred embodiment, $k_{rel}$ is more than 1. Preferably, $k_{rel}$ is 1.3 or more, more preferably 1.4 or more, even more preferably 1.5 or more, even more preferably 1.7 or more, even more preferably 2.0 or more, yet even more preferably 2.2 or more and most preferably 2.5 or more.

In Table 2 (Column 3-4) the rate constants k and relative rate constants $k_{rel}$ of several examples of the process according to the invention, wherein the (hetero)cycloalkyne is according to Formula (6b) and the (hetero)aryl 1,3-dipole compound is according to Formula (3k)-(3r) or (3zh), (3zi), (3zj) or (3zk), are shown. The reference (hetero)aryl 1,3-dipole compound for (3k)-(3r) in order to determine the relative rate constant $k_{rel}$ is phenyl azide. The relative rate constant $k_{rel}$ is determined by dividing the rate constant k for the cycloaddition according to the invention, i.e. the cycloaddition of (6b) with (hetero)aryl 1,3-dipole compounds (3k)-(3r), by the rate constant for the cycloaddition of (6b) with the reference compound phenyl azide. As a comparison, the rate constants k and relative rate constants $k_{rel}$ of several comparative examples, wherein the β-alanine derivative of DIBAC was used as (hetero)cycloalkyne, are also shown.

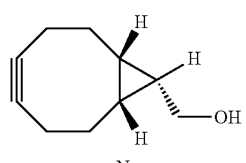

6b

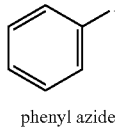

phenyl azide

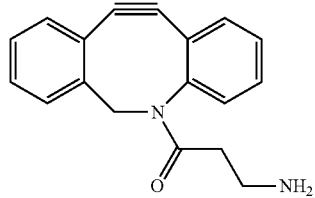

DIBAC derivative

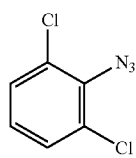

3k

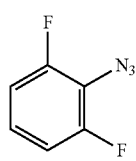

3l

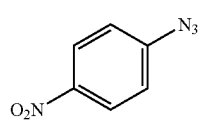

3m

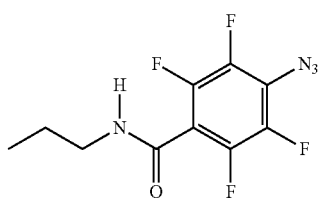

3n

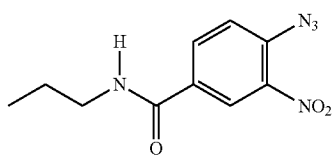

3o

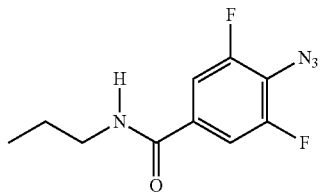

3p

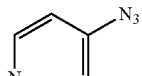

3q

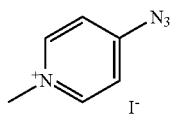

3r

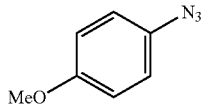

3s

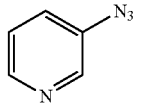

3zh

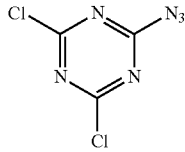

3zi

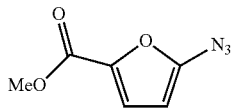

3zj

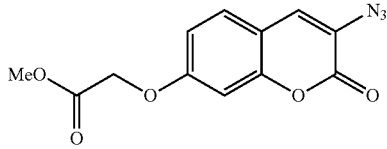

3zk

As a comparative example, the reaction rate k and relative reaction rate $k_{rel}$ for the cycloaddition of the (hetero)cycloalkyne according to Formula (6b) with an aliphatic 1,3-dipole compound, benzyl azide, is also shown in Table 2 (entry 1).

As a comparative example, the reaction rate k and relative reaction rate $k_{rel}$ for the cycloaddition of the (hetero)cycloalkyne according to Formula (6b) with 3s is included in Table 2 (entry 11). A methoxy substituent has a meta-Hammett constant am of 0.12 and a para-Hammett constant $\sigma_p$ of −0.27 (Hansch et al., Chem. Rev. 1991, 91, 165-195, incorporated by reference). As was described above, in an embodiment according to the invention, since am is positive, a methoxy substituent may be present on the meta position with respect to the azide group. However, since $\sigma_p$ is negative, a methoxy substituent may not be present on the para position with respect to the azide group. In 3s the methoxy substituent is present on the para position, and example 3s is therefore a comparative example.

TABLE 2

Rate constants k and relative rate constants $k_{rel}$ of the cycloaddition of (hetero)aryl 1,3-dipole compounds (3k)-(3s), phenyl azide and benzyl azide with (hetero)cycloalkyne (6b) and with DIBAC derivative. All experiments performed in THF/H$_2$O = 9/1.

| | | Column 3-4 Cycloalkyne (6b) | | Column 4-5 DIBAC derivative 26a | |
|---|---|---|---|---|---|
| Entry | azide | k (M$^{-1}$ s$^{-1}$) | $k_{rel}$ | k (M$^{-1}$ s$^{-1}$) | $k_{rel}$ |
| 1 | Benzyl azide (comparative) | 0.070 | 0.35 | 0.24 | 7.3 |
| 2 | Phenyl azide (reference compound) | 0.20 | 1.0 (by definition) | 0.033 | 1.0 (by definition) |
| 3 | 3k | 0.41 | 2.1 | 0.28 | 8.5 |
| 4 | 3l | 0.63 | 3.2 | 0.14 | 4.2 |
| 5 | 3m | 0.53 | 2.7 | 0.02 | 0.6 |
| 6 | 3n | 1.23 | 6.2 | 0.16 | 4.8 |
| 7 | 3o | 0.38 | 1.9 | 0.018 | 0.5 |
| 8 | 3p | 0.73 | 3.7 | 0.11 | 3.3 |
| 9 | 3q | 0.68 | 2.0 | 0.05 | 1.5 |
| 10 | 3r | 2.0 | 10 | 0.05 | 1.5 |
| 11 | 3s (comparative) | 0.18 | 0.9 | 0.058 | 1.8 |

Entries 3-8, relating to the cycloaddition process according to the invention, clearly show that $k_{rel}$ is larger than 1 for the process according to the invention, i.e. for the cycloaddition of a (hetero)cycloalkyne with a (hetero)aryl 1,3-dipole compound comprising one or more substituents having a positive value for $\sigma_p$ and/or $\sigma_m$. Entries 9 and 10, also clearly show that $k_{rel}$ is larger than 1 for the process according to the invention, i.e. for the cycloaddition of a (hetero)cycloalkyne with a (hetero)aryl 1,3-dipole compound wherein the (hetero)aryl group is an electron-poor (hetero)aryl group.

This is in contrast to the general opinion that 1,3-cycloaddition reactions of a (hetero)cycloalkyne and a 1,3-dipole proceed most efficiently with an electron-rich azide and an electron-deficient alkynes.

Entries 1 and 11, relating to the comparative examples as described above, do not show an increase in $k_{rel}$.

In addition, comparison of entries 1 and 2 of Table 2 shows that the cycloaddition of a (hetero)cycloalkyne according to Formula (1) with a (hetero)aromatic 1,3-dipole compound (phenyl azide, entry 2), has a higher reaction rate than the cycloaddition of a (hetero)cycloalkyne according to Formula (1) with an aliphatic 1,3-dipole compound (benzyl azide, entry 1).

This result is in contrast to results obtained in the prior art with dibenzoannulated cyclooctynes (e.g. DIBAC), where the reaction rate for the cycloaddition with an aliphatic 1,3-dipole is higher than the reaction rate for cycloaddition with an aromatic 1,3-dipole.

Figure 2:
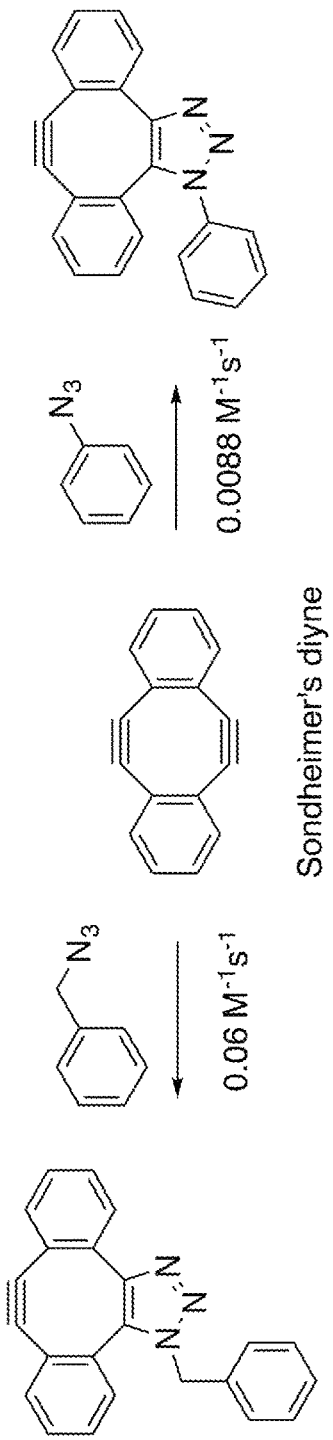
FIG. 2 shows the cycloaddition reaction and reaction rate constants of benzyl azide or phenyl azide with Sondheimer's diyne in MeOH.

For example, the vast majority of model cycloadditions of SPAAC applications involve the reaction with an aliphatic azide, e.g. benzyl azide or azidoacetic acid, due to the higher reactivity of aliphatic azides as compared to aromatic azides. For example, Hosoya et al., *Scientific Reports* 2011, 1, article number 82 (doi: 10.1038/srep00082), incorporated by reference herein, have reported that cycloadditions of benzyl azide or phenyl azide with Sondheimer's diyne (a dibenzoannulated cyclooctyne) in MeOH proceed with a reaction rate constant of 0.06 or 0.0088 M$^{-1}$s$^{-1}$, respectively, hence a factor 6.8 faster for benzyl azide. The cycloaddition reactions of benzyl azide or phenyl azide with Sondheimer's diyne (a dibenzoannulated cyclooctyne) in MeOH is shown in FIG. 2.

Comparison of azides in reaction with DIBAC shows a similar 7.3× higher reaction rate for benzyl azide versus phenyl azide (see entries 1 and 2 in Table 2). Interestingly, Hosoya et al. also recently reported that the reaction rate of Sondheimer's diyne with an aromatic azide can be increased by double ortho substitution of the aryl moiety of phenyl azide with alkyl groups, leading to a $k_{rel}$ of 36, 43 or even 76 for o,o-dimethyl, o,o-diethyl or o,o-diisopropyl substituents, respectively. A modest positive effect on reaction rate (×3.8) was also noted for introduction of an electron-donating para-substituent (MeO), while an electron-withdrawing group (p-CF$_3$) led to an opposite effect (reaction rate×0.9). According to these results it appears that the most efficient cycloadditions of azides and cyclic alkynes involve electron-rich azides with electron-deficient alkynes.

Figure 5:
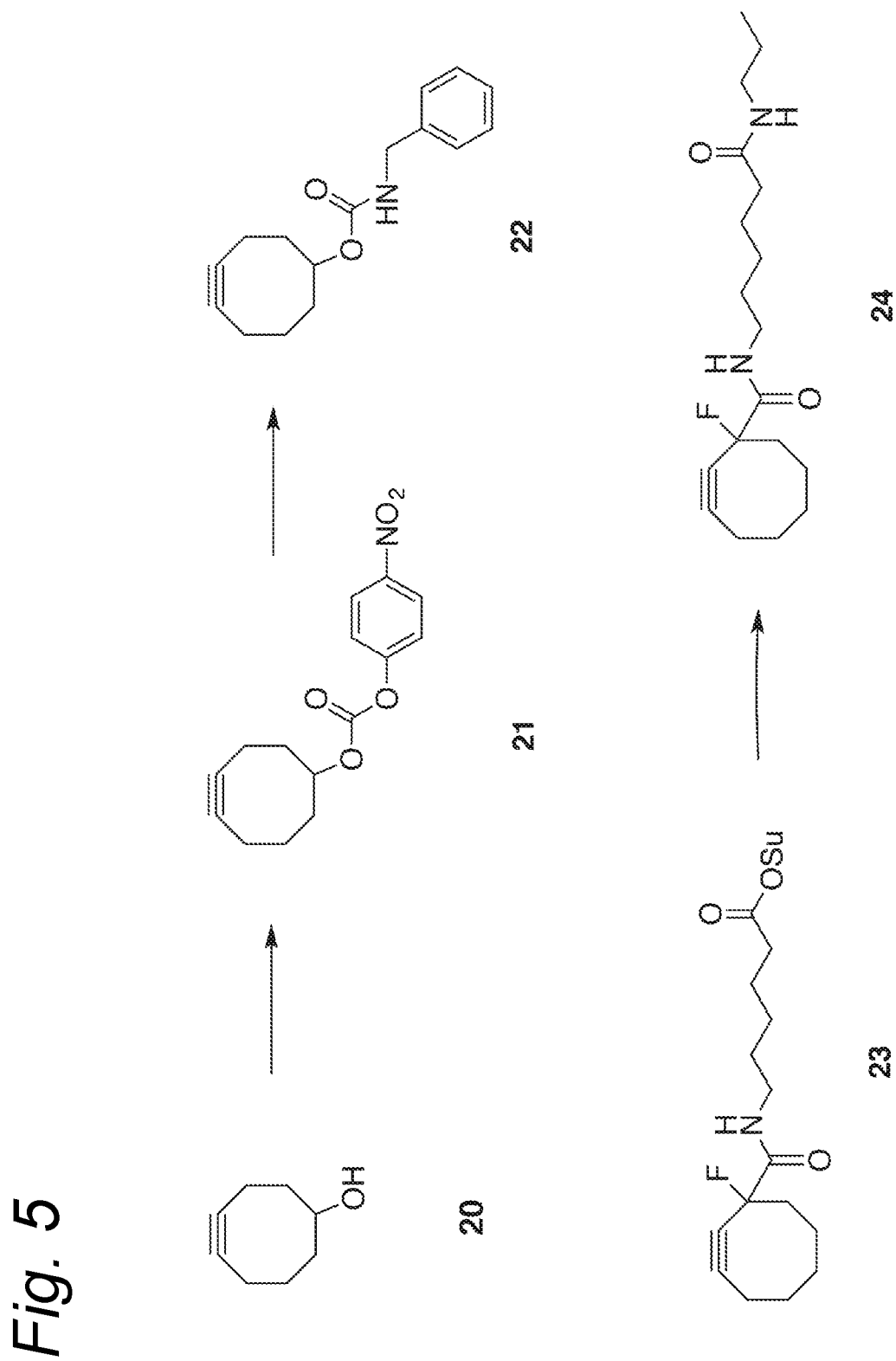
FIG. 5 shows the synthetic schemes for the preparation of the benzyl carbamate derivative of 4-hydroxycyclooctynol (22) and the propyl amide derivative of MOFO (24).
Figure 6:
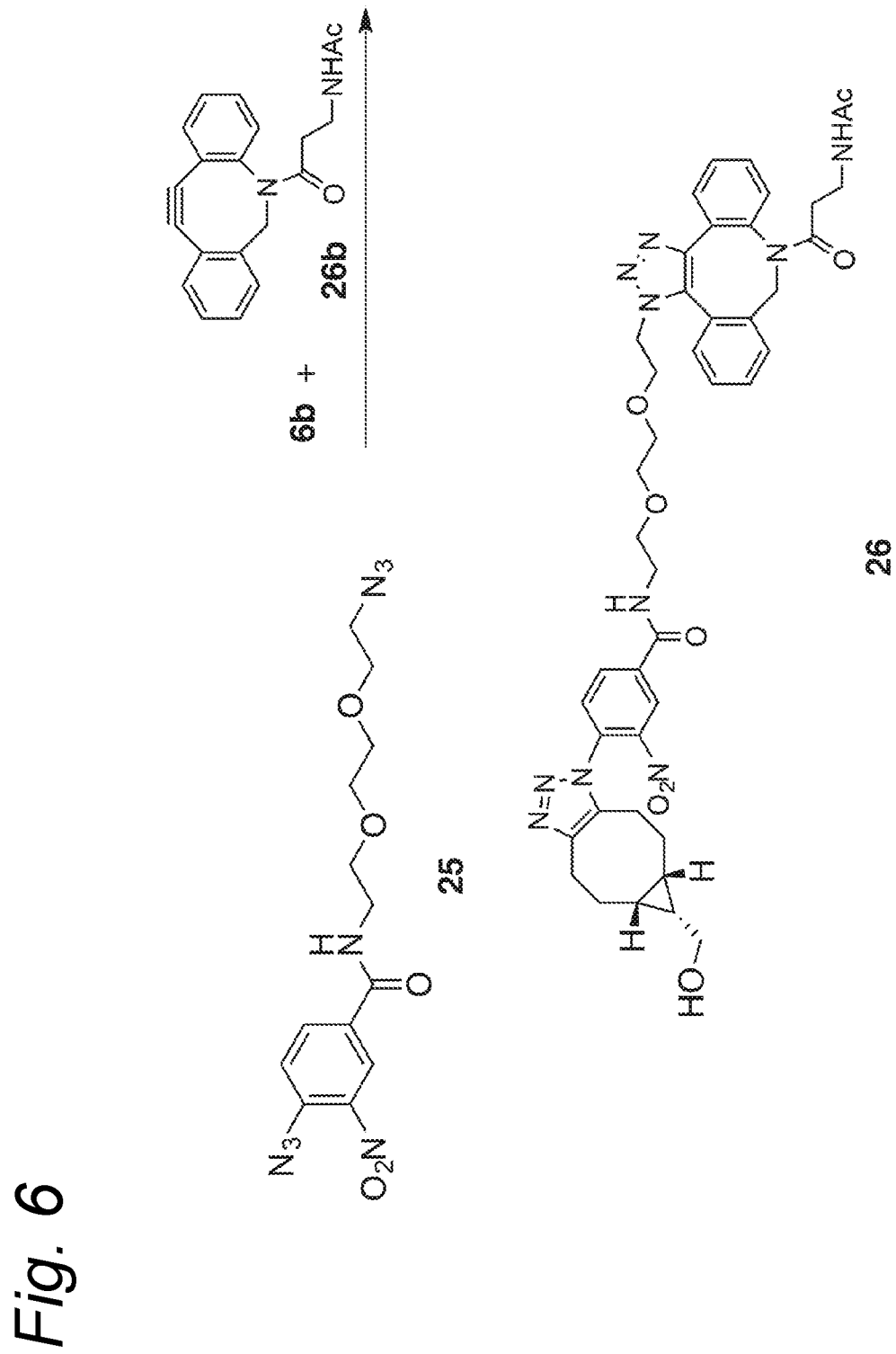
FIG. 6 shows the reaction scheme for the one-pot, chemoselective copper-free click reaction of bisazide 25 with a mixture of BCN-derivative 6b and DIBAC-derivative 26b, leading to bistriazole 26.
Figure 7:
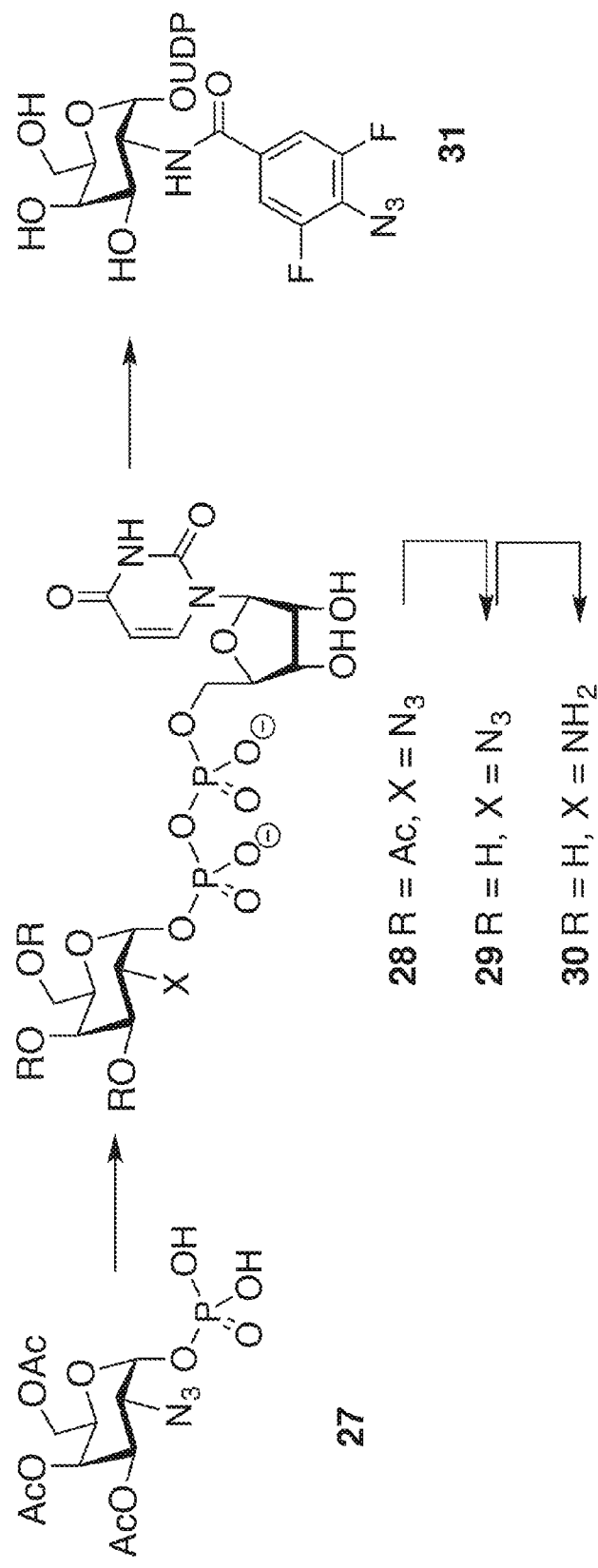
FIG. 7 shows the reaction scheme for the chemical synthesis of bisfluoroazidophenyl derivative of GalNAc (31).

An additional demonstration of enhanced reactivity of electron-poor azides with electron-rich alkynes stems from reaction rate constants of the benzyl carbamate derivative of cyclooct-4-yn-1-ol (FIG. 5, compound 22) with azides. It was established that a competition experiment for cycloaddition of 22 with p-nitrophenylazide (3m) versus benzyl azide shows near exclusive formation (>95%) of the cycloaddition with 3m.

Rate Constant $k_{rel(DIBAC)}$

When the reaction rate of the process according to the invention, i.e. the cycloaddition of (hetero)cycloalkyne according to Formula (1) with a (hetero)aromatic 1,3-dipole compound wherein (i) the (hetero)aryl group is an electron-poor (hetero)aryl group, as defined above, and/or (ii) the (hetero)aryl group of the (hetero)aryl 1,3-dipole compound comprises one or more substituents having a positive value for $\sigma_p$ and/or $\sigma_m$, is compared to e.g. the reaction rate of the cycloaddition of DIBAC (also referred to as DBCO) with the same (hetero)aryl 1,3-dipole compound, the reaction rate of the process according to the invention is higher.

Therefore, in a preferred embodiment of the process according to the invention, the process has a relative rate constant $k_{rel(DIBAC)}$ of 1 or more. The relative rate constant $k_{rel(DIBAC)}$ is defined as the rate constant of the process according to the invention, i.e. the cycloaddition of a (hetero)cycloalkyne according to Formula (1) with a (hetero)aryl 1,3-dipole compound comprising one or more substituents having a positive value for $\sigma_p$ and/or $\sigma_m$, divided by the rate constant of the cycloaddition of DIBAC with the same (hetero)aryl 1,3-dipole compound. Relative rate constants $k_{rel(DIBAC)}$ for the cycloaddition of (hetero)aryl 1,3-dipole compounds (3k)-(3p), with (hetero)cycloalkyne (6b) are also shown in Table 3. In order to determine $k_{rel(DIBAC)}$, the rate constants k of the cycloaddition of benzyl azide (entry 1) and phenyl azide (entry 2) are also shown in Table 3.

TABLE 3

Rate constants k of the cycloaddition of (hetero)aryl 1,3-dipole compounds (3k)-(3p), phenyl azide and benzyl azide with (hetero)cycloalkyne (6b) and with DIBAC derivative, and $k_{rel(DIBAC)}$. All experiments performed in THF/H$_2$O = 9/1.

| Entry | azide | Column 3 Cycloalkyne (6b) k (M$^{-1}$ s$^{-1}$) | Column 4 DIBAC derivative 26a k (M$^{-1}$ s$^{-1}$) | $k_{rel(DIBAC)}$ |
|---|---|---|---|---|
| 1 | Benzyl azide (comparative) | 0.070 | 0.24 | 0.29 |
| 2 | Phenyl azide (reference compound) | 0.20 | 0.033 | 6.1 |
| 3 | 3k | 0.41 | 0.28 | 1.5 |
| 4 | 3l | 0.63 | 0.14 | 4.5 |
| 5 | 3m | 0.53 | 0.02 | 27 |
| 6 | 3o | 0.38 | 0.018 | 21 |
| 7 | 3p | 0.73 | 0.11 | 6.6 |

In a further preferred embodiment, $k_{rel(DIBAC)}$ is more than 1. Preferably, $k_{rel(DIBAC)}$ is 1.5 or more, more preferably 2.0 or more, even more preferably 3.0 or more, even more preferably 5.0 or more, even more preferably 10.0 or more, yet even more preferably 15.0 or more and most preferably 20.0 or more.

In a further preferred embodiment of the process according to the invention, the process has a relative rate constant $k_{rel}$ of 1.0 or more and a relative rate constant $k_{rel(DIBAC)}$ of 1.0 or more. In this embodiment it is further preferred that $k_{rel(DIBAC)}$ is 1.5 or more, more preferably $k_{rel(DIBAC)}$ is 2.0 or more, even more preferably $k_{rel(DIBAC)}$ is 3.0 or more, even more preferably $k_{rel(DIBAC)}$ is 5.0 or more, even more preferably $k_{rel(DIBAC)}$ is 10.00 or more, yet even more preferably $k_{rel(DIBAC)}$ is 15.0 or more and most preferably $k_{rel(DIBAC)}$ is 20.0 or more.

In yet a further preferred embodiment of the process according to the invention, the process has a relative rate constant $k_{rel}$ of 1.3 or more and a relative rate constant $k_{rel(DIBAC)}$ of 1.5 or more. In this embodiment it is further preferred that $k_{rel(DIBAC)}$ is 2.0 or more, even more preferably $k_{rel(DIBAC)}$ is 3.0 or more, even more preferably $k_{rel(DIBAC)}$ is 5.0 or more, even more preferably $k_{rel(DIBAC)}$ is 10.0 or more, yet even more preferably $k_{rel(DIBAC)}$ is 15.0 or more and most preferably $k_{rel(DIBAC)}$ is 20.0 or more.

In yet a further preferred embodiment of the process according to the invention, the process has a relative rate constant $k_{rel}$ of 1.5 or more and a relative rate constant $k_{rel(DIBAC)}$ of 1.5 or more. In this embodiment it is further preferred that $k_{rel(DIBAC)}$ is 2.0 or more, even more preferably $k_{rel(DIBAC)}$ is 3.0 or more, even more preferably $k_{rel(DIBAC)}$ is 5.0 or more, even more preferably $k_{rel(DIBAC)}$ is 10.0 or more, yet even more preferably $k_{rel(DIBAC)}$ is 15.0 or more and most preferably $k_{rel(DIBAC)}$ is 20.0 or more.

In yet a further preferred embodiment of the process according to the invention, the process has a relative rate constant $k_{rel}$ of 1.7 or more and a relative rate constant $k_{rel(DIBAC)}$ of 1.5 or more. In this embodiment it is further preferred that $k_{rel(DIBAC)}$ is 2.0 or more, even more preferably $k_{rel(DIBAC)}$ is 3.0 or more, even more preferably $k_{rel(DIBAC)}$ is 5.0 or more, even more preferably $k_{rel(DIBAC)}$ is 10.0 or more, yet even more preferably $k_{rel(DIBAC)}$ is 15.0 or more and most preferably $k_{rel(DIBAC)}$ is 20.0 or more.

In yet a further preferred embodiment of the process according to the invention, the process has a relative rate constant $k_{rel}$ of 2.0 or more and a relative rate constant $k_{rel(DIBAC)}$ of 1.5 or more. In this embodiment it is further preferred that $k_{rel(DIBAC)}$ is 2.0 or more, even more preferably $k_{rel(DIBAC)}$ is 3.0 or more, even more preferably $k_{rel(DIBAC)}$ is 5.0 or more, even more preferably $k_{rel(DIBAC)}$ is 10.0 or more, yet even more preferably $k_{rel(DIBAC)}$ is 15.0 or more and most preferably $k_{rel(DIBAC)}$ is 20.0 or more.

In yet a further preferred embodiment of the process according to the invention, the process has a relative rate constant $k_{rel}$ of 2.2 or more and a relative rate constant $k_{rel(DIBAC)}$ of 1.5 or more. In this embodiment it is further preferred that $k_{rel(DIBAC)}$ is 2.0 or more, even more preferably $k_{rel(DIBAC)}$ is 3.0 or more, even more preferably $k_{rel(DIBAC)}$ is 5.0 or more, even more preferably $k_{rel(DIBAC)}$ is 10.0 or more, yet even more preferably $k_{rel(DIBAC)}$ is 15.0 or more and most preferably $k_{rel(DIBAC)}$ is 20.0 or more.

In yet a further preferred embodiment of the process according to the invention, the process has a relative rate constant $k_{rel}$ of 2.5 or more and a relative rate constant $k_{rel(DIBAC)}$ of 1.5 or more. In this embodiment it is further preferred that $k_{rel(DIBAC)}$ is 2.0 or more, even more preferably $k_{rel(DIBAC)}$ is 3.0 or more, even more preferably $k_{rel(DIBAC)}$ is 5.0 or more, even more preferably $k_{rel(DIBAC)}$ is 10.0 or more, yet even more preferably $k_{rel(DIBAC)}$ is 15.0 or more and most preferably $k_{rel(DIBAC)}$ is 20.0 or more.

To summarize, in contrast to dibenzoannulated cyclooctynes, the reaction rate of a (hetero)cycloalkyne according to Formula (1), in particular when the (hetero)cycloalyne is an aliphatic (hetero)cycloalkyne as defined above and more in particular when the (hetero)cycloalkyne is according to Formula (4), with a (hetero)aryl 1,3-dipole compound, e.g. an aryl azide or a (hetero)aryl azide, is higher than with an aliphatic 1,3-dipole compound, e.g. an aliphatic azide.

In addition, the reaction rate of an aryl azide or a (hetero)aryl azide with an aliphatic cyclooctyne can be increased by introduction of electron-withdrawing substituents on the aryl moiety. Furthermore, judicious choice of these substituents enables the selective reaction of an aryl azide or a (hetero)aryl azide with an aliphatic cyclooctyne versus reaction with an aromatic cyclooctyne, with selectivity factors exceeding 20.

Cycloaddition Products

The present invention further relates to the cycloaddition products obtainable by the process according to the invention, said process comprising the step of reacting a (hetero)aryl 1,3-dipole compound with a (hetero)cycloalkyne, wherein the (hetero)aryl group of the (hetero)aryl 1,3-dipole compound (i) is an electron-poor (hetero)aryl group, as defined above, and/or (ii) comprises one or more substituents having a positive value for the para-Hammett substituent constant $\sigma_p$ and/or the meta-Hammett substituent constant $\sigma_m$, and wherein the (hetero)cycloalkyne is according to Formula (1). The (hetero)cycloalkyne according to Formula (1) and preferred embodiments thereof, and the (hetero)aryl 1,3-dipole compound and preferred embodiments thereof are described in more detail above.

The invention therefore also relates to a compound obtainable by the process according to the invention.

The invention relates to a compound obtainable by the process according to the invention, wherein the compound is according to Formula (12a), (12b), (12c) or (12d) as defined below. The invention also relates to a compound obtainable by the process according to the invention, wherein the compound is according to Formula (12e), (12f), (12g) or (12h) as defined below.

The invention also relates to a compound obtainable by the process according to the invention, wherein the compound is according to Formula (13a), (13b), (13c) or (13d) as defined below.

The invention also relates to a compound obtainable by the process according to the invention, wherein the compound is according to Formula (14a), (14b), (14c) or (14d) as defined below. The invention also relates to a compound obtainable by the process according to the invention, wherein the compound is according to Formula (14e), (14f), (14g) or (14h) as defined below.

As described above, the process according to the invention particularly relates to a process comprising the step of reacting a (hetero)aryl 1,3-dipole compound with a (hetero)cycloalkyne, wherein the (hetero)aryl 1,3-dipole compound is a (hetero)aryl azide or a (hetero)aryl diazo compound; wherein the (hetero)aryl group of the (hetero)aryl 1,3-dipole compound (i) is an electron-poor (hetero)aryl group, as defined above, and/or (ii) comprises one or more substituents having a positive value for the para-Hammett substituent constant $\sigma_p$ and/or the meta-Hammett substituent constant $\sigma_m$; and wherein the (hetero)cycloalkyne is an aliphatic (hetero)cyclooctyne according to Formula (1) or an aliphatic (hetero)cyclononyne according to Formula (1). The aliphatic (hetero)cyclooctyne and aliphatic (hetero)cyclononyne according to Formula (1) and preferred embodiments thereof, and the (hetero)aryl azide and (hetero)aryl diazo compound and preferred embodiments thereof are described in more detail above.

The invention therefore particularly relates to a compound obtainable by the process according to the invention, wherein the compound is according to Formula (12a) or (12d) as defined below. The invention also particularly relates to a compound obtainable by the process according to the invention, wherein the compound is according to Formula (12e) or (12h) as defined below.

The invention also relates to a compound obtainable by the process according to the invention, wherein the compound is according to Formula (13a) or (13d) as defined below.

The invention also relates to a compound obtainable by the process according to the invention, wherein the compound is according to Formula (14a) or (14d) as defined below.

The invention also relates to a compound obtainable by the process according to the invention, wherein the compound is according to Formula (14e) or (14h) as defined below.

The invention further relates to a compound obtainable by the process according to the invention, wherein the compound is according to Formula (12i) or (12j) as defined below.

The invention further relates to a compound obtainable by the process according to the invention, wherein the compound is according to Formula (13e) as defined below.

The invention further relates to a compound obtainable by the process according to the invention, wherein the compound is according to Formula (14i) or (14j) as defined below.

The invention also relates to the cycloaddition product of a (hetero)cycloalkyne according to Formula (1) and a (hetero)aryl 1,3-dipole compound according to Formula (2). The invention further relates to a compound, wherein the compound is according to Formula (12a), (12b), (12c) or (12d):

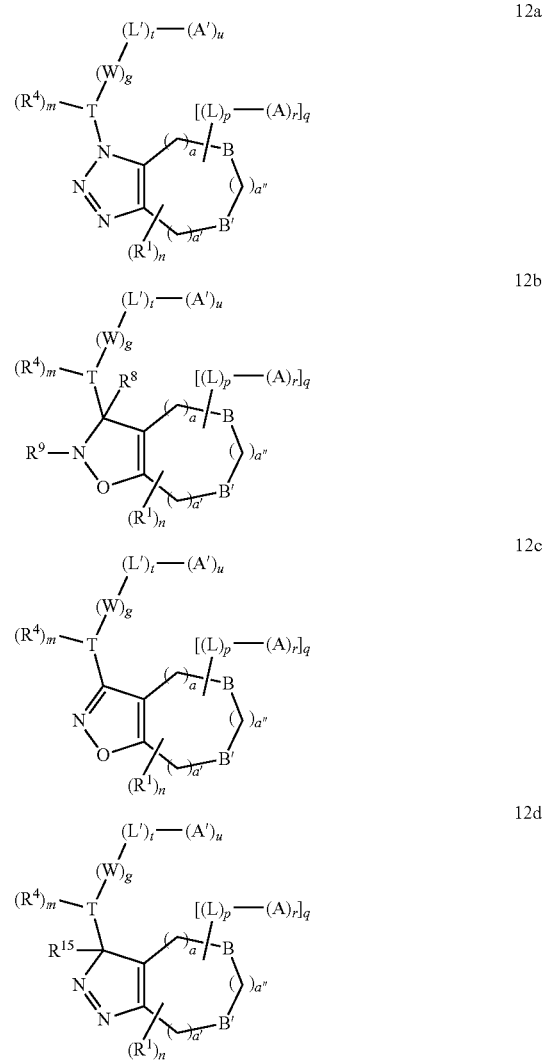

wherein:
$R^1$, n, B, B', a, a', a'', L, p, q, r and A are as defined above for (1);
L', A', T, $R^4$, W, g, t, u and m are as defined above for (2);
$R^8$ is selected from the group consisting of hydrogen, $C_1$-$C_{12}$ alkyl groups and $(L'')_iA''$, wherein L'' is as defined for L', A'' is as defined for A', i is 0 or 1, wherein L'' is selected independently from L' and L''' and wherein A'' is selected independently from A' and A''';
$R^9$ is selected from the group consisting of $C_1$-$C_{12}$ alkyl groups and $(L''')_wA'''$, wherein L''' is as defined for L', A''' is as defined for A', w is 0 or 1, wherein L''' is selected independently from L' and L'' and wherein A''' is selected independently from A' and A'';
optionally $R^8$ and $R^9$ may together form a (hetero)cycloalkyl group, the (hetero)cycloalkyl group optionally being substituted; and
$R^{15}$ is selected from the group consisting of hydrogen, $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N.

The invention particularly relates to a compound according to Formula (12a) or (12d) as defined above.

In the process according to the invention, when the (hetero)aryl 1,3-dipole compound is a diazo compound, an isomer (12i) of compound (12d) may be formed when $R^{15}$ is hydrogen. The invention therefore further relates to a compound according to Formula (12i):

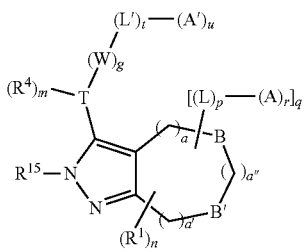

12i wherein:
$R^1$, n, B, B', a, a', a'', L, p, q, r and A are as defined above for (1);
L', A', T, $R^4$, W, g, t, u and m are as defined above for (2); and
$R^{15}$ is H.

In the compounds according to Formula (12a), (12b), (12c) or (12d), or the compound according to Formula (12i), it is preferred that a+a'+a'' is 4. In a further preferred embodiment, a and a' are 1 and a'' is 2. In another preferred embodiment, a and a' are 2 and a'' is 0.

The invention particularly relates to a compound according to Formula (12a), (12d) or (12i), wherein a, a' and a'' are independently 1, 2, 3 or 4, with the proviso that a+a'+a''=4; and n is 0-8; or wherein a, a' and a'' are independently 1, 2, 3, 4 or 5, with the proviso that a+a'+a''=5; and n is 0-10.

In another preferred embodiment of the process according to the invention, the (hetero)cycloalkyne is an aliphatic (hetero)cycloalkyne according to Formula (4). The invention therefore also relates to the cycloaddition product of a (hetero)cycloalkyne according to Formula (4) and a (hetero)aryl 1,3-dipole compound according to Formula (2). The invention further relates to a compound, wherein the compound is according to Formula (12e), (12f), (12g), or (12h):

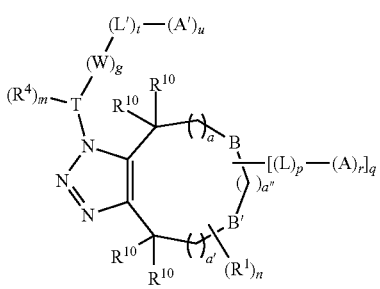

12e

-continued

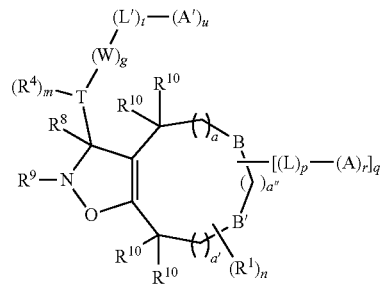

12f

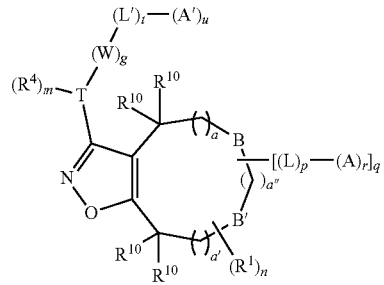

12g

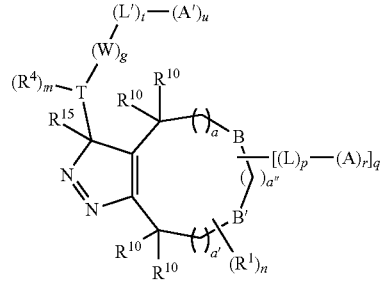

12h wherein:
a, a', a'', n, $R^1$, $R^{10}$, B, B', p, r, L, A, q, D, E and Q are as defined above for (4);
L', A', T, $R^4$, W, g, t, u and m are as defined above for (2);
$R^8$, $R^9$ are as defined above for (12b); and
$R^{15}$ is as defined above for (12d).

The invention particularly relates to a compound according to Formula (12e) or (12h) as defined above.

In the process according to the invention, when the (hetero)aryl 1,3-dipole compound is a diazo compound, an isomer (12j) of compound (12h) may be formed when $R^{15}$ is hydrogen. The invention therefore further relates to a compound according to Formula (12j):

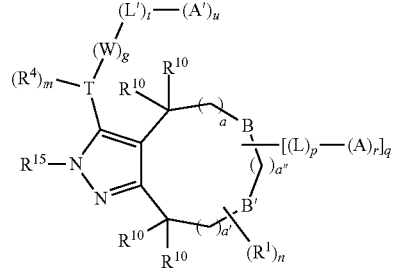

12j wherein:
a, a', a'', n, $R^1$, $R^{10}$, B, B', p, r, L, A, q, D, E and Q are as defined above for (4);

L', A', T, $R^4$, W, g, t, u and m are as defined above for (2); and $R^{15}$ is H.

The invention particularly relates to a compound according to Formula (12e) or (12h) or (12j), wherein a, a' and a" are independently 0, 1 or 2, with the proviso that a+a'+a"=2; and n is 0-4; or wherein a, a' and a" are independently 0, 1, 2 or 3, with the proviso that a+a'+a"=3; and n is 0-6.

The preferred embodiments for $R^1$, L' and A' as described above for a (hetero)cycloalkyne according to Formula (1) also apply to the preferred embodiments of $R^1$, L and A (hetero)cycloalkyne according to Formula (4). It is further preferred that r is 1 or 2. In the aliphatic (hetero)cycloalkyne according to Formula (4), a+a'+a" is 2, 3, 4, 5 or 5. Preferably, a+a'+a" is 2, i.e. the (hetero)cycloalkyne preferably is a (hetero)cyclooctyne.

In one embodiment, it is further preferred that a is 0, a' is 0 and a" is 2. In this embodiment, it is further preferred that B is O and B' is O. In a further preferred embodiment, a is 0, a' is 0 and a" is 2, B is O and B' is O, and even more preferably $[(L)_p\text{-}(A)_r]$ is present on one of the a"-C-atoms. In another further preferred embodiment, a is 0, a' is 0 and a" is 2, B is $C(R^3)_2$ and B' is $C(R^3)_2$, and $[(L)_p\text{-}(A)_r]$ is present on one of the a"-C-atoms.

In another preferred embodiment, a is 1, a' is 1 and a" is 0. In this embodiment it is further preferred that B is $C(R^3)[(L)_p\text{-}(A)_r]$ and B' is $C(R^3)_2$, or that B is $N[(L)_p\text{-}(A)_r]$ and B' is $C(R^3)_2$.

Preferably, n is 0, 1, 2, 3, 4, 5, 6, 7 or 8, more preferably n is 0, 1, 2, 3, 4, 5 or 6, even more preferably n is 0, 1, 2, 3 or 4 and most preferably n is 0, 1 or 2.

In this embodiment it is further preferred that $R^{10}$ is hydrogen or $C_1$-$C_{24}$ alkyl groups, more preferably hydrogen or $C_1$-$C_{12}$ alkyl groups, even more preferably hydrogen or $C_1$-$C_6$ alkyl groups, more preferably hydrogen or $C_1$-$C_4$ alkyl groups. Most preferably, $R^{10}$ is hydrogen.

The invention also relates to the cycloaddition product of a (hetero)cycloalkyne according to Formula (5) and a (hetero)aryl 1,3-dipole compound according to Formula (2). The invention therefore also relates to a compound according to claim 12 or claim 13, wherein the compound is according to Formula (13a), (13b), (13c) or (13d):

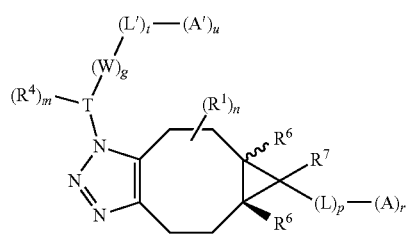

13a

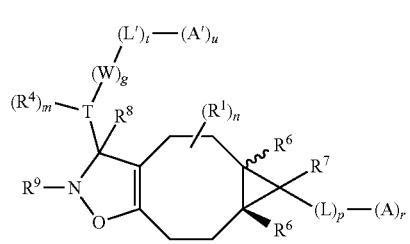

13b

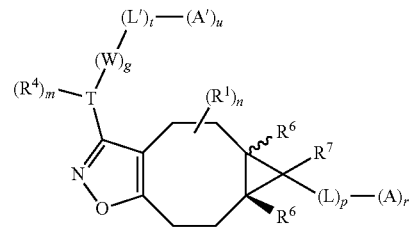

13c

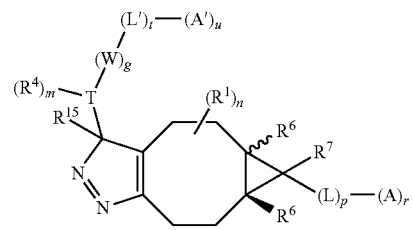

13d wherein:
L, p, q, r and A are as defined above for (1);
L', A', T, $R^4$, W, g, t, u and m are as defined in above for (2);
$R^1$, n, $R^6$ and $R^7$ are as defined above for (5); and
$R^8$, $R^9$ and $R^{15}$ are as defined above.

In the process according to the invention, when the (hetero)aryl 1,3-dipole compound is a diazo compound, an isomer (13e) of compound (13d) may be formed when $R^{15}$ is hydrogen. The invention therefore further relates to a compound according to Formula (13e):

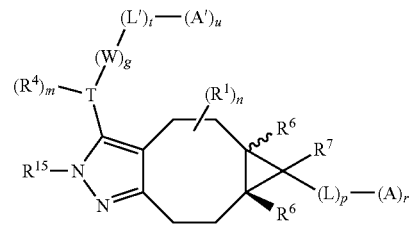

13e wherein:
L, p, q, r and A are as defined above for (1);
L', A', T, $R^4$, W, g, t, u and m are as defined in above for (2);
$R^1$, n, $R^6$ and $R^7$ are as defined above for (5); and
$R^{15}$ is H.

In the compounds according to Formula (13a), (13b), (13c), (13d) or (13e), it is preferred that n is 0, and $R^6$ and $R^7$ are H. Most preferably, n is 0, and $R^6$ and $R^7$ are H. In another preferred embodiment, $(L)_p\text{-}(A)_r$ is $(L)_p\text{-}(Q)$, wherein Q is a functional group as defined above. In a further preferred embodiment, $(L)_p\text{-}(A)_r$ is OH, i.e. p is 0 and A is Q, wherein Q is OH.

The invention particularly relates to a compound according to Formula (13a), (13d) or (13e), as defined above. Preferably, n is 0 and both $R^6$ and $R^7$ are H.

The invention also relates to the cycloaddition product of a (hetero)cycloalkyne according to Formula (1) and a (hetero)aryl 1,3-dipole compound according to Formula (3). In a preferred embodiment, the (hetero)aryl 1,3-dipole compound is according to Formula (3a). The invention also relates to a compound according to any one of claims 12-14, wherein the compound is according to Formula (14a), (14b), (14c) or (14d):

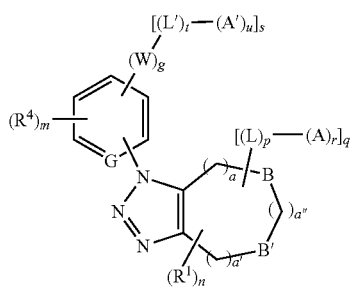

14a

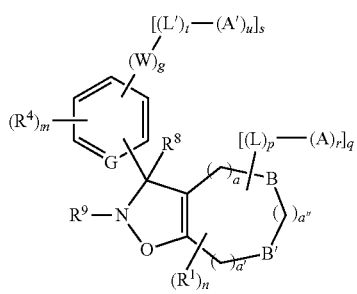

14b

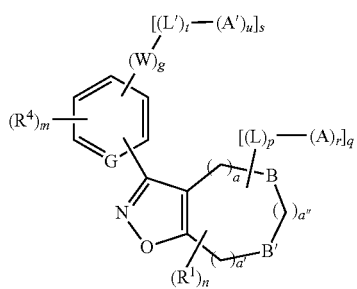

14c

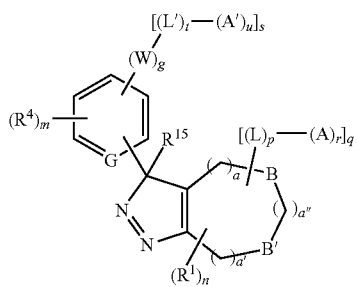

14d wherein:
R¹, n, B, B', a, a', a", L, p, q, r and A are as defined above;
L', A', R⁴, W, g, t, u and m are as defined above;
G and s are as defined above; and
R⁸, R⁹ and R¹⁵ are as defined above.

In the compounds according to Formula (14a), (14b), (14c) or (14d), it is preferred that a+a'+a" is 4. In a further preferred embodiment, a and a' are 1 and a" is 2.

In the process according to the invention, when the (hetero)aryl 1,3-dipole compound is a diazo compound, an isomer (14i) of compound (14d) may be formed when R¹⁵ is hydrogen. The invention therefore further relates to a compound according to Formula (14i):

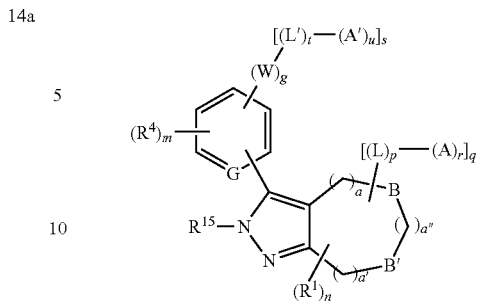

14i wherein:
R¹, n, B, B', a, a', a", L, p, q, r, A L', A', R⁴, W, g, t, u, m, G and s are as defined above for (14d); and
R¹⁵ is H.

The invention particularly relates to a compound according to Formula (14a), (14d) or (14i) wherein a, a' and a" are independently 1, 2, 3 or 4, with the proviso that a+a'+a"=4; and n is 0-8; or wherein a, a' and a" are independently 1, 2, 3, 4 or 5, with the proviso that a+a'+a"=5; and n is 0-10.

Preferred embodiments for the (hetero)aryl group are described in more detail above. In a further preferred embodiment, the heteroaryl group is selected from the group consisting of phenyl groups, pyridinyl groups, pyridiniumyl groups, pyrimidinyl groups, pyrimidinium groups, pyrazinyl groups, pyradizinyl groups, pyrrolyl groups, pyrrolium groups, furanyl groups, thiophenyl groups, diazolyl groups, quinolinyl groups, imidazolyl groups, oxazolyl groups and oxazolium groups, more preferably from the group consisting of phenyl groups, pyridinyl groups, pyridiniumyl groups, pyrimidinyl groups, pyrimidinium groups pyrrolyl groups, furanyl groups and thiophenyl groups, all groups optionally substituted with one or more substituents as defined above.

Most preferably, the (hetero)aryl group is selected from the group consisting of phenyl groups, pyridinyl groups and pyridiniumyl groups, all groups optionally substituted with one or more substituents as defined above.

R⁴ is preferably a halogen (F, Cl, Br or I), more preferably R⁴ is F, Cl or Br, most preferably F or Cl.

In another preferred embodiment the invention relates to the 1,3-cycloaddition product of an aliphatic (hetero)cycloalkyne according to Formula (4) and a (hetero)aryl 1,3-dipole compound according to Formula (3a), (3b), (3c), (3d), (3e) or (3f). In a further preferred embodiment the (hetero)aryl 1,3-dipole compound is according to Formula (3a). Therefore the invention further relates to a compound according to Formula (14e), (14f), (14g) or (14h):

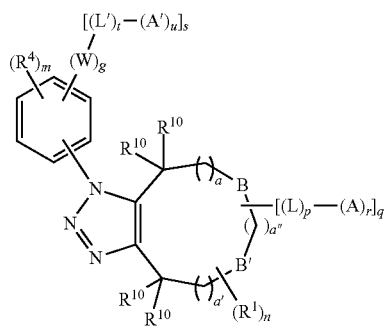

14e

-continued

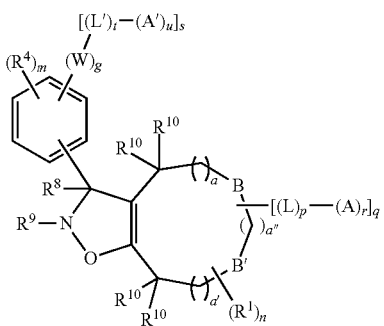

14f

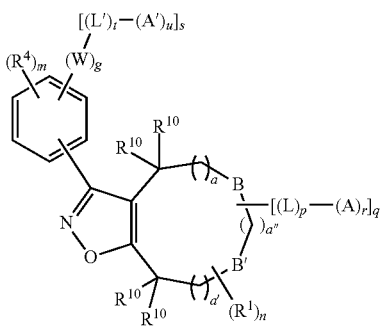

14g

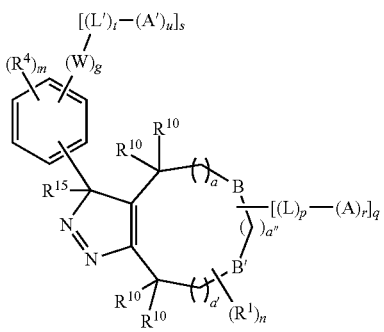

14h wherein:
a, a', a", n, $R^1$, $R^{10}$, B, B', p, r, L, A, q, D, E and Q are as defined above for (4);
$R^4$, m, W, g, L', t, A', u and s are as defined above for (3a); and
$R^8$, $R^9$ and $R^{15}$ are as defined above.

In the process according to the invention, when the (hetero)aryl 1,3-dipole compound is a diazo compound, an isomer (14j) of compound (14h) may be formed when $R^{15}$ is hydrogen. The invention therefore further relates to a compound according to Formula (14j):

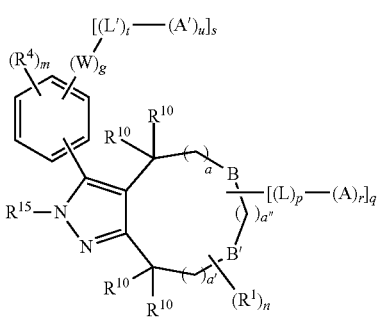

14j wherein:
a, a', a", n, $R^1$, $R^{10}$, B, B', p, r, L, A, q, D, E and Q are as defined above for (4);
$R^4$, m, W, g, L', t, A', u and s are as defined above for (3a); and
$R^{15}$ is hydrogen.

In this embodiment it is preferred that a+a'+a" is 2, in other words, it is preferred that the (hetero)cycloalkyne is a (hetero)cyclooctyne. It is further preferred that a is 0, a" is 1 and a' is 1.

It is also preferred that the (hetero)aryl group is a phenyl group, a pyridinyl group or pyridiniumyl group.

In this embodiment it is further preferred that $R^{10}$ is hydrogen or $C_1$-$C_{24}$ alkyl groups, more preferably hydrogen or $C_1$-$C_{12}$ alkyl groups, even more preferably hydrogen or $C_1$-$C_6$ alkyl groups, more preferably hydrogen or $C_1$-$C_4$ alkyl groups. Most preferably, $R^{10}$ is hydrogen.

The invention particularly relates to a compound according to Formula (14e), (14h) or (14j), wherein a, a' and a" are independently 0, 1 or 2, with the proviso that a+a'+a"=2; and n is 0-4; or wherein a, a' and a" are independently 1, 2 or 3, with the proviso that a+a'+a"=3; and n is 0-10.

In cycloadducts according to Formula (12a), (12b), (12c), (12d), (12e), (12f), (12g), (12h), (13a), (13b), (13c), (13d), (14a), (14b), (14c), (14d), (14e) and (14f), (14g), and in cycloadducts according to Formula (14h), (12i), (12j), (13e), (14i), (14j), (hetero)aryl group T may be any (hetero)aryl group. Preferred embodiments for T are described above. More preferably, (hetero)aryl group T is selected from the group consisting of phenyl groups, pyridinyl groups, pyridiniumyl groups, pyrimidinyl groups, pyrimidinium groups, pyrazinyl groups, pyradizinyl groups, pyrrolyl groups, pyrrolium groups, furanyl groups, thiophenyl groups, diazolyl groups, quinolinyl groups, imidazolyl groups, oxazolyl groups and oxazolium groups, more preferably from the group consisting of phenyl groups, pyridinyl groups, pyridiniumyl groups, pyrimidinyl groups, pyrimidinium groups pyrrolyl groups, furanyl groups and thiophenyl groups, all groups optionally substituted with one or more substituents as defined above.

More preferably, the (hetero)aryl group is selected from the group consisting of phenyl groups, pyridinyl groups and pyridiniumyl groups, all groups optionally substituted with one or more substituents as defined above.

In cycloadducts according to Formula (12a), (12b), (12c), (12d), (12e), (12f), (12g), (12h), (13a), (13b), (13c), (13d), (14a), (14b), (14c), (14d), (14e) and (14f), (14g) and in cycloadducts according to Formula (14h), (12i), (12j), (13e), (14i), (14j), $R^4$, if present, is defined as above. More preferably, the (hetero)aryl group of the (hetero)aryl group in the cycloadduct comprises one or more substituents independently selected from the group consisting of —$OR^{11}$, halogen (—F, —Cl, —Br, —I, more preferably —F, —Cl, —I), $C_1$-$C_6$ haloalkyl (preferably $C_1$-$C_6$ chloroalkyl or $C_1$-$C_6$ fluoroalkyl, e.g. —$CF_3$, —$C_2F_5$, —$CCl_3$, —$C_2Cl_5$), —CN, —NC, —$NO_2$, —NCO, —OCN, —NCS, —SCN, —$N^+(R^{11})_3$—C(O)N$(R^{11})_2$, —C(O)$R^{11}$, —C(O)X$R^{11}$, —S(O)$R^{11}$, —S(O)$_2R^{11}$, —S(O)O$R^{11}$, —S(O)$_2$O$R^{11}$, —S(O)N$(R^{11})_2$, —S(O)$_2$N$(R^{11})_2$, —OS(O)$_2R^{11}$, —OC(O)$R^{11}$, —OC(O)O$R^{11}$, —OC(O)N$(R^{11})_2$, wherein $R^{11}$, and the preferred embodiments of $R^{11}$, are as defined above.

Even more preferably, the cycloadducts comprise one or more substituents independently selected from the group consisting of O$R^{11}$, halogen (preferably —F, —Cl), —$NO_2$, —CN, —$N^+(R^{11})_3$, —C(O)$R^{11}$, —C(O)O$R^{11}$, —C(O)N$(R^{11})_2$, —S(O)$R^{11}$ and —S(O)$_2R^{11}$, wherein $R^{11}$ and preferred embodiments of $R^{11}$ are as defined above.

Most preferably, the (hetero)aryl group comprises one or more substituents independently selected from the group consisting of $OR^{11}$, halogen (preferably —F, —Cl), —$NO_2$, —CN, —N+$(R^{11})_3$, —C(O)$R^{11}$, —C(O)O$R^{11}$, —C(O)N$(R^{11})_2$, —S(O)$R^{11}$ and —S(O)$_2R^{11}$, wherein $R^{11}$ is hydrogen or a $C_1$-$C_{12}$ alkyl group.

Preferably, m is 0, 1, 2, 3 or 4, preferably 0, 1 or 2, most preferably 0, when the (hetero)aryl group is an electron-poor (hetero)aryl group as defined above. When the (hetero)aryl group is electron-rich, m is preferably 1, 2, 3 or 4.

As will be clear to a person skilled in the art, m and $R^4$ in the cycloaddition product correspond to m and $R^4$ in the (hetero)aryl 1,3-dipole compound that reacted with the (hetero)cycloalkyne in the process according to the invention. Therefore, the preferred embodiments of m and $R^4$ in the cycloadduct corresponds to the preferred embodiments of the (hetero)aryl 1,3-dipole compound that were described in more detail above.

In a further preferred embodiment, the (hetero)aryl part of the cycloadduct according to Formula (12a), (12b), (12c), (12d), (12e), (12f), (12g), (12h), (13a), (13b), (13c), (13d), (14a), (14b), (14c), (14d), (14e) and (14f), (14g), and in cycloadducts according to Formula (14h), (12i), (12j), (13e), (14i), (14j), is 2,5-dichlorophenyl or 2,5-difluorophenyl.

EXAMPLES

Synthesis of Azides

Example 1. Synthesis of Phenyl Azide (Azidobenzene)

Phenyl azide was prepared according to a literature procedure: S W. Kwok et al., *Org. Synth.* 2010, 12, 4217, incorporated by reference.

Example 2. Synthesis of 1-azido-2,6-dichlorobenzene (3k)

Synthesized according procedure in patent WO2007/140174 A2, 2007, incorporated by reference.

Example 3. Synthesis of 1-azido-2,6-difluorobenzene (3l)

Synthesized according literature procedure: L. Jin et al., *Angew. Chem. Int. Ed.*, 2013, 52, 5309, incorporated by reference.

Example 4. Synthesis of 1-azido-4-nitrobenzene (3m)

Synthesized according literature procedure: S. W. Kwok et al., *Org. Synth.* 2010, 12, 4217, incorporated by reference.

Figure 4:
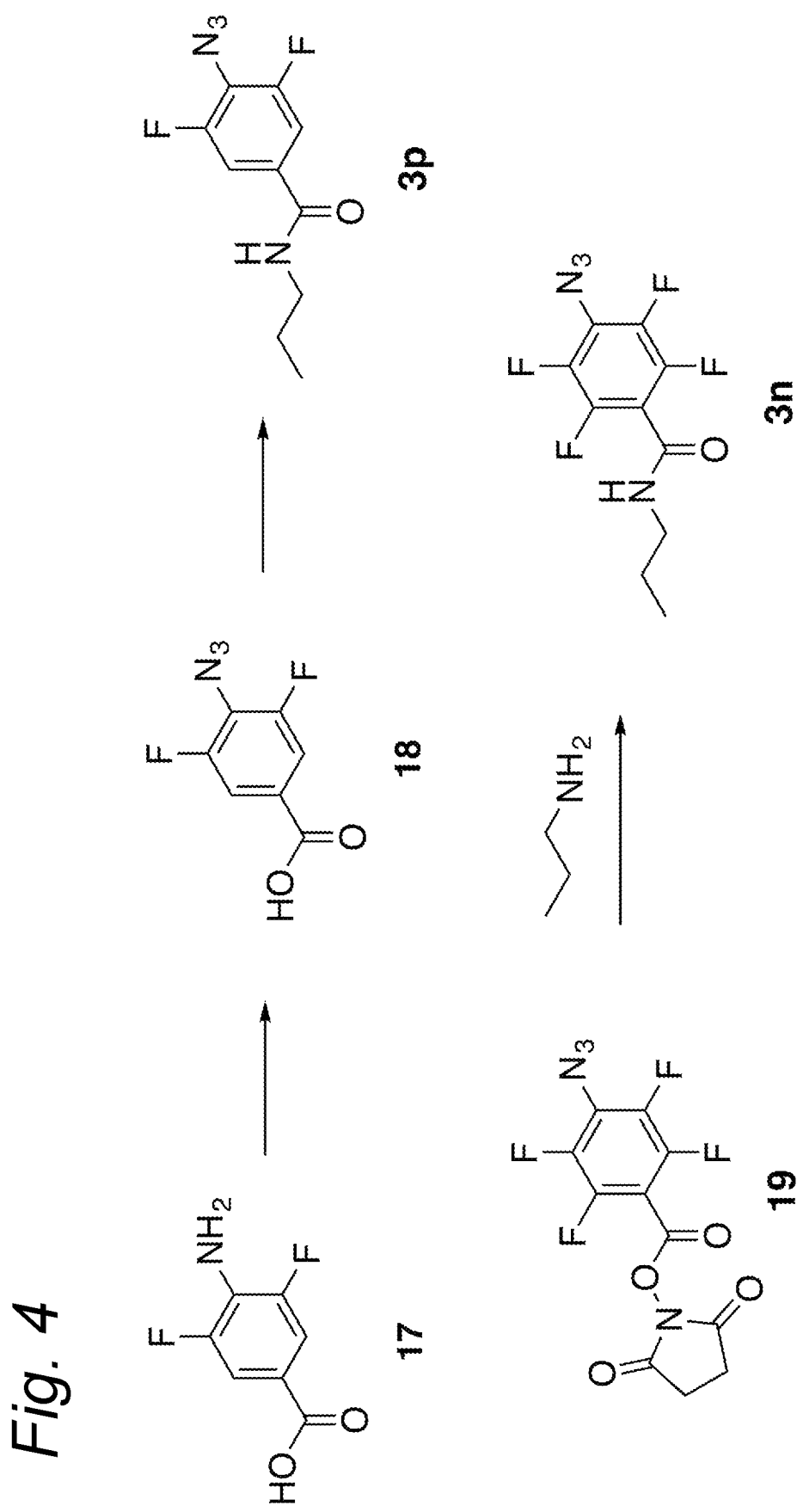
FIG. 4 shows the synthetic schemes for the preparation of compound 3p and 3n.

Example 5. Synthesis of 1-azido-2,3,5,6-tetrafluoro-4-(n-propylcarboxamido)benzene (3n), depicted in FIG. 4 (bottom)

To a solution of the N-succinimidyl 4-azido-2,3,5,6-tetrafluorobenzoate (19, 250 mg, 0.753 mmol) in DCM (5 mL) was added $nPrNH_2$ (620 mL, 7.53 mmol). The mixture was stirred at rt for 15 min. The excess $nPrNH_2$ was evaporated, the residue was dissolved in DCM and washed with $H_2O$. The organic layer was dried ($Na_2SO_4$), filtered and concentrated in vacuo. The residue was purified by column chromatography (EtOAc/pentane, 1:4) to afford the product (173 mg, 83%) as a white solid.

$^1$H NMR (CDCl$_3$, 400 MHz): δ 5.95 (bs, 1H), 3.46-3.41 (m, 2H), 1.69-1.60 (m, 2H), 0.99 (t, 3H) ppm.

Figure 3:
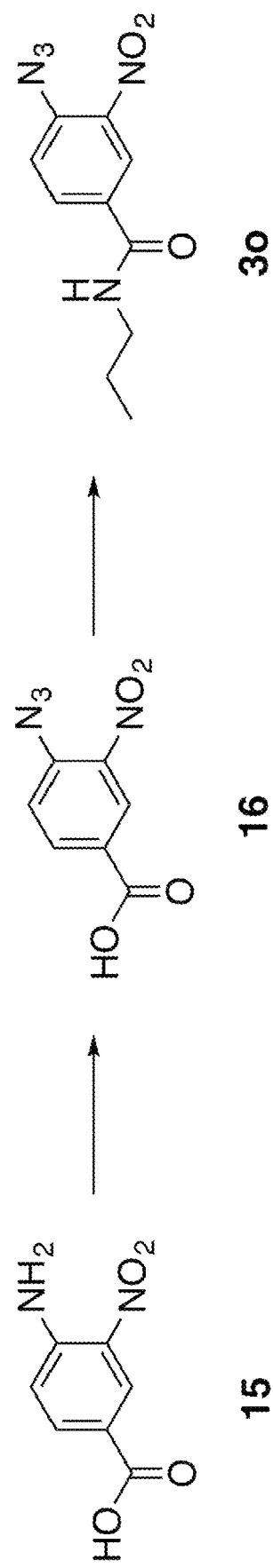
FIG. 3 shows the synthetic scheme for the preparation of compound 3o.

Example 6. Synthesis of 1-azido-2-nitro-4-(n-propylcarboxamido)benzene (3o), Depicted in FIG. 3

To a solution of 4-amino-3-nitrobenzoic acid (15, 4.55 g, 25.0 mmol) in a mixture of HOAc (50 mL) and conc. $H_2SO_4$ (50 mL) was added slowly at 0° C. a solution of $NaNO_2$ (1.80 g, 26 mmol) in conc. $H_2SO_4$ (25 mL). After stirring for 1.5 h at 0° C. the mixture was poured in ice (100 g) and filtered. The filtrate was added to a solution of $NaN_3$ (115 mmol) in $H_2O$ (25 mL). The azide was precipitated, filtered and dried to afford a yellow solid (16, 5.10 g, 98%).

To a solution of the azide (16, 250 mg, 1.20 mmol) in THF (10 mL) was added at 0° C. ClCO$_2$iBu (171 mL, 1.32 mmol) and NEt$_3$ (184 mL, 1.32 mmol). The mixture was stirred for 0.5 h at 0° C. A solution of $nPrNH_2$ (148 mL, 1.80 mmol) in THF (2 mL) was added dropwise at 0° C. After stirring for 1 h at 0° C., the mixture was quenched with $H_2O$ (20 mL), and extracted with EtOAc (3×30 mL). The organic layer was washed with sat. NaHCO$_3$, dried (Na$_2$SO$_4$), filtered and concentrated in vacuo. The residue was purified by column chromatography (EtOAc/DCM, 1:7) to afford the propyl amide (3p, 180 mg, 60%) as pale yellow solid.

$^1$H NMR (CDCl$_3$, 400 MHz): δ 8.30 (s, 1H), 8.08 (d, 1H), 7.40 (d, 1H), 6.35 (bs, 1H), 3.47-3.41 (m, 2H), 1.71-1.62 (m, 2H), 1.02 (t, 3H) ppm.

Example 7. Synthesis of 1-azido-2,6-difluoro-4-(n-propylcarboxamido)benzene (3p), Depicted in FIG. 4 (Top)

First, 4-amino-3,5-difluorobenzoic acid (17) was prepared according literature procedure: Bléger et al., *J. Am. Chem. Soc.* 2012, 134, 20597. Then, to a solution of 4-amino-3,5-difluorobenzoic acid (17, 1 g, 4.77 mmol) in TFA (25 mL) was added slowly at 0° C. NaNO$_2$ (658 mg, 9.54 mmol). The mixture was stirred for 1 h at 0° C. NaN$_3$ (3.10 g, 47.7 mmol) was added in small portions to keep the temperature below 5° C. Et$_2$O (20 mL) was added and the solution was stirred 2 h at rt. The reaction mixture was quenched with $H_2O$ (30 mL) and extracted with Et$_2$O. The organic layer was washed with sat. NaCl, dried (Na$_2$SO$_4$), filtered and concentrated in vacuo. The product 18 was used without further purification in the next step.

$^1$H NMR (CDCl$_3$, 400 MHz): δ 7.70-7.63 (m, 2H) ppm.

Next, to a solution of 4-azido-3,5-difluorobenzoic acid (18, 250 mg, 1.26 mmol) in THF (10 mL) was added at 0° C. ClCO$_2$iBu (179 mL, 1.38 mmol) and NEt$_3$ (192 mL, 1.38 mmol). The mixture was stirred for 0.5 h at 0° C. A solution of $nPrNH_2$ (155 mL, 1.88 mmol) in THF (2 mL) was added dropwise at 0° C. After stirring for 1 h at 0° C., the mixture was quenched with $H_2O$ (20 mL), and extracted with EtOAc (3×30 mL). The organic layer was washed with sat. NaHCO$_3$, dried (Na$_2$SO$_4$), filtered and concentrated in vacuo. The residue was purified by column chromatography (EtOAc/heptane, 1:1) to afford the product (230 mg, 76%) as a white solid.

$^1$H NMR (CDCl$_3$, 400 MHz): δ 7.38-7.32 (m, 2H), 6.10 (bs, 1H), 3.43-3.38 (m, 2H), 1.68-1.59 (m, 2H), 0.99 (t, 3H) ppm.

Example 8. Synthesis of 4-azido-1-methylpyridine (3q)

Synthesized according literature procedure: Z. Yia and Q. Zhu, *Bioorg. & Med. Chem. Lett.* 2010, 20, 6222, incorporated by reference.

Example 9. Synthesis of 4-azido-1-methylpyridinium iodide (3r)

Synthesized according literature procedure: Z. Yia and Q. Zhu, *Bioorg. & Med. Chem. Lett.* 2010, 20, 6222, incorporated by reference.

Example 9-1

Synthesis of 3-azidopyridine (3zh)

To a solution of 3-aminopyridine (250 mg, 2.66 mmol) in MeOH (15 mL) were added CuSO4 (33 mg, 0.13 mmol) and 1H-imidazole-1-sulfonyl azide, HCl salt (1.19 g, 5.31 mmol) and the resulting suspension was stirred at r.t. for 2 d. The reaction was diluted with EtOAc (30 mL) and washed with $H_2O$:brine 1:1 (15 mL). The organic layer was dried over $Na_2SO_4$, and concentrated in vacuo. Flash chromatography (15:1-2:1 pent:EtOAc) afforded 3zh (44 mg, 0.37 mmol, 14%). $^1$H-NMR (400 MHz, $CDCl_3$): δ 8.41-8.36 (m, 2H), 7.40-7.29 (m, 2H) ppm.

Example 9-2

Synthesis of 2-azido-4,6-dichlorocyranuric acid (3zi)

Prepared according to Bucher, G.; Siegler, F.; Wolff, J. J.; *Chem Commun*, 1999, 2113-2114.

To a solution of trichlorocyanuric acid (0.5 g, 2.7 mmol) in acetone (5 mL) in a separation funnel was added a solution of sodium azide (160 mg, 2.5 mmol) in water (2 mL). The mixture was shaken for 5 min followed by layer separation. The organic layer was partly concentrated followed by the addition of DCM (5 mL) and water (5 mL). The water layer was extracted with DCM (2×5 mL) and the combined organic layers were dried over $Na_2SO_4$, filtrated and concentrated. Purification via flash chromatography (pentane:DCM 100:0→1:2) gave 3zi (120 mg, 0.63 mmol, 23%). $^{13}$C-NMR (100 MHz, $CDCl_3$): δ 172.6, 171.4 ppm.

Example 9-3

Synthesis of methyl 5-azidofuran-2-carboxylate (3zj)

Methyl 5-nitrofuran-2-carboxylate (250 mg, 1.46 mmol) was dissolved in DMSO (6 mL) followed by the addition of $NaN_3$ (238 mg, 3.65 mmol). After stirring overnight, additional $NaN_3$ (238 mg, 3.65 mmol) was added and the mixture was stirred overnight again. Subsequently, DCM (20 mL) and water (20 mL) were added and the water layer was extracted with DCM (1×10 mL). The organic layer was washed with water (3×10 mL), dried over $Na_2SO_4$, filtrated and concentrated under reduced pressure. Purification via flash chromatography (pentane: EtOAc 100:0→4:1) gave the product (155 mg, 0.93 mmol, 64%). $^1$H-NMR (400 MHz, $CDCl_3$): δ 7.17 (d, J=3.6 Hz, 1H), 5.89 (d, J=3.6 Hz, 1H), 3.88 (s, 3H) ppm.

Example 9-4

Synthesis of 3-azido-7-(methylcarboxymethoxy)coumarin (3zk)

3-azido-7-hydroxy-coumarin was prepared according to a literature procedure (Sivakumar, K.; Xie, F.; Cash, B. M.; Long, S.; Barnhill, H. N.; Wang, Q. *Org. Lett.* 2004, 6, 4603).

3-Azido-7-hydroxy-coumarin (190 mg, 0.93 mmol) and $K_2CO_3$ (190 mg, 1.12 mmol) were suspended in DMF (5 mL) and stirred for 10 minutes followed by the addition of methyl bromoacetate (81 μL, 0.93 mmol). The mixture was heated to 40° C. for 3 h followed by cooling down to room temperature and the addition of water (15 mL) and EtOAc (15 mL). The waterlayer was extracted with EtOAc (3×15 mL) and the combined organic layers were dried over $Na_2SO_4$, filtrated and concentrated under reduced pressure. Purification via flash chromatography (heptane: EtOAc 100: 0→5:1) gave 3zk (95 mg, 0.36 mmol, 40%). $^1$H-NMR (300 MHz, $CDCl_3/CD_3OD$): δ 7.39 (d, J=8.8 hz, 1H), 7.30 (s, 1H), 6.91-6.88 (m, 1H), 6.83-6.82 (m, 1H), 4.73 (s, 2H), 3.76 (s, 3H) ppm.

Example 9-5

Synthesis of 4-azido-N-benzyl-3,5-difluorobenzamide (3zl)

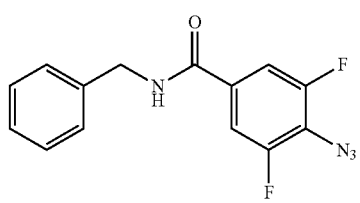

3zl 2,5-Dioxopyrrolidin-1-yl 4-azido-3,5-difluorobenzoate (77 mg, 0.259 mmol) was dissolved in DCM (3 mL) and benzylamine (34 μL, 0.312 mmol) and $Et_3N$ (54 μL, 0.389 mmol) were added. The reaction was stirred for 4 days at r.t. after which the solvent was removed under reduced pressure. Flash chromatography (4:1-1:1 pent:EtOAC) afforded 3zl (61 mg, 0.211 mmol, 82%).

$^1$H-NMR (400 MHz, $CDCl_3$): δ 7.30-7.17 (m, 7H), 6.79 (br s, 1H), 4.45 (d, J=5.6 Hz, 2H) ppm. LRMS (ESI+) calcd for $C_{14}H_{10}N_4O$ (M+H$^+$) 289.09. found 289.26.

Synthesis of Cyclooctyne Derivatives

Example 10. Synthesis of Cyclooctyn Derivative 22

Cyclooct-4-yn-1-ol 20 was prepared according to a literature procedure: J. L. Jessen et al. *Chem. Ber.,* 1986, 119, 297, incorporated by reference.

To a solution of 20 (14 mg, 0.113 mmol) in DCM (3 mL) was added pyridine (18 mL, 0.226 mmol) and 4-nitrophenoxy chloroformate (28 mg, 0.141 mmol). The mixture was stirred at rt for 2 h and quenched with sat. $NH_4Cl$. The $H_2O$ layer was extracted with DCM. The organic layer was dried ($Na_2SO_4$), filtered and concentrated in vacuo. The residue was purified by column chromatography (EtOAc/heptane, 4:1) to afford the carbonate 21 (16 mg, 49%).

To a solution of the carbonate (21, 16 mg, 0.055 mmol) in DCM (2 mL) was added nPrNH$_2$ (45 mL, 0.553 mmol). After stirring for 1 h at rt the solvent was evaporated. The residue was purified by column chromatography (EtOAc/pentane, 1:5) to afford the product 22 as a colourless oil (7 mg, 61%).

$^1$H NMR (CDCl$_3$, 400 MHz): δ 4.74-4.60 (m, 2H), 3.16-3.11 (m, 2H), 2.52-2.44 (m, 1H), 2.22-1.95 (m, 8H), 1.88-1.81 (m, 1H), 1.56-1.47 (m, 2H), 0.92 (t, 3H) ppm.

Example 11. Synthesis of Cyclooctyn Derivative 24

To a solution of succinimide 23 (20 mg, 0.052 mmol), commercially available from Jena Bioscience, in DCM (1 mL) was added n-PrNH$_2$ (43 mL, 0.52 mmol). After stirring for 0.5 h at rt DCM was added (10 mL) and the mixture was washed with H$_2$O (1 mL). The organic layer was dried (Na$_2$SO$_4$), filtered and concentrated in vacuo. The residue was purified by column chromatography (EtOAc/heptane, 4:1) to afford the product 24 (14 mg, 82%).

$^1$H NMR (CDCl$_3$, 400 MHz): δ 6.41 (bs, 1H), 5.55 (bs, 1H), 3.56-3.19 (m, 4H), 2.48-2.22 (m, 4H), 2.17 (t, 2H), 2.11-1.82 (m, 4H), 1.71-1.63 (m, 3H), 1.60-1.44 (m, 5H), 1.39-1.32 (m, 2H), 0.92 (t, 3H) ppm.

General Procedure Kinetic Experiments by IR
IR Experiments

To a solution of azide (1 mL, 20 mM) in a mixture of THF and H$_2$O (9:1) was added a solution of cyclooctyn (1 mL, 26 mM) in a mixture of THF and H$_2$O (9:1). To follow the reaction, the solution was transferred to an IR-cell (CaF$_2$) and IR-spectra were taken of specific wavelength area (2300-1900 cm$^{-1}$) at preset time-intervals. Kinetics of the reaction were determined by measuring the decrease of the integral of the signal caused by the azide. From the conversion plots thus obtained, the second order rate plots were calculated according to equation:

$$kt = \frac{1}{[B]_0 - [A]_0} \times \ln\frac{[A]_0([B]_0 - [P])}{([A]_0 - [P])[B]_0}$$

with k=2$^{nd}$ order rate constant (M$^{-1}$s$^{-1}$), t=reaction time (s), [A]$_0$=the initial concentration of substrate A (mmol/mL), [B]$_0$=the initial concentration of substrate B (mmol/mL) and [P]=the concentration of product (mmol/mL).

All experiments were performed in duplo.

Example 12. Synthesis of Bis-Azide 25

To a solution of 16 (416 mg, 2.00 mmol) in THF (10 mL) was added ClCO$_2$i-Bu (285 μL, 2.20 mmol) and NEt$_3$ (306 μL, 2.20 mmol) at 0° C. The mixture was stirred for 0.5 h at 0° C. A solution of H$_2$N—(POE)$_3$-N$_3$ (523 mg, 3.00 mmol) in THF (2 mL) was added dropwise at 0° C. After stirring for 1 h at 0° C., the mixture was quenched with H$_2$O (20 mL), and extracted with DCM (3×30 mL). The organic layer was dried (Na$_2$SO$_4$), filtered and concentrated in vacuo. The residue was purified by column chromatography (EtOAc/DCM, 1:3) to afford 25 (540 mg, 74%) as a yellow viscous oil. R$_f$ 0.20 (EtOAc/DCM, 1:3). $^1$H NMR (CDCl$_3$, 400 MHz): δ 8.35 (d, J=2.0 Hz, 1H), 8.09 (dd, J=8.5, 2.1 Hz, 1H), 7.39 (d, J=8.4 Hz, 1H), 7.27-7.26 (m, 1H), 3.73-3.68 (m, 10H), 3.41-3.38 (m, 2H) ppm. $^{13}$C NMR (CDCl$_3$, 125 MHz): δ 164.4, 140.4, 137.7, 132.8, 131.4, 124.9, 121.0, 70.6, 70.4, 70.4, 70.2, 69.7, 69.5, 50.7, 40.2. HRMS (ESI+) m/z calcd for C$_{13}$H$_{16}$N$_8$NaO$_5$ (M+Na)$^+$: 387.1141. found: 387.1137.

Example 13. Synthesis of Compound 26b

To a solution of DIBAC-NH$_2$ 26a (100 mg, 0.362 mmol) in DCM (5 mL) was added Ac$_2$O (51 μL, 0.543 mmol), NEt$_3$ (101 μL, 0.724 mmol) and a cat. amount of DMAP. After stirring for 16 h at rt water (5 mL) was added and the mixture was extracted with DCM (3×10 mL). The organic layer was dried (Na$_2$SO$_4$), filtered and concentrated in vacuo. The residue was purified by column chromatography (MeOH/DCM, 1:19) to afford 26b (106 mg, 92%) as a white solid. R$_f$ 0.32 (MeOH/DCM, 1:19). $^1$H NMR (CDCl$_3$, 400 MHz): δ 7.68 (d, J=7.5 Hz, 1H), 7.42-7.26 (m, 7H), 6.07-6.02 (m, 1H), 5.14 (d, J=13.9 Hz, 1H), 3.70 (d, J=13.9 Hz, 1H), 3.38-3.30 (m, 1H), 3.24-3.16 (m, 1H), 2.46 (ddd, J=16.6, 7.7, 4.0 Hz, 1H), 1.96 (ddd, J=16.6, 7.3, 3.7 Hz, 1H), 1.81 (s, 3H) ppm. $^{13}$C NMR (CDCl$_3$, 125 MHz): δ 172.5, 170.0, 151.2, 148.1, 132.2, 129.2, 128.7, 128.6, 128.5, 128.0, 127.4, 125.7, 123.1, 122.7, 114.9, 107.9, 55.7, 35.4, 34.9, 23.3. HRMS (ESI+) m/z calcd for C$_{20}$H$_{18}$N$_2$NaO$_2$ (M+Na)$^+$: 341.1266. found: 341.1275.

Example 14. Reaction of Bisazide 25 with 6b and 26b

To a solution of BCN alcohol 6b (28 mg, 0.188 mmol) and DIBAC derivative 26b (60 mg, 0.188 mmol) in THF (2 mL) was added a solution of bisazide 25 (34 mg, 0.094 mmol) in THF (1 mL). The mixture was stirred at rt for 3 h, when TLC analysis indicated complete conversion. LCQ analysis of the crude reaction mixture indicated the formation of three new products, with the major peak corresponding to that of compound 26 (M+H$^+$=833) and minor peaks indicative of double SPAAC of 25 with 6b (M+H$^+$=665) and double SPAAC of 25 with 26b (M+H$^+$=1001). The reaction mixture was concentrated and purified by two consecutive silica gel column chromatography purifications (column 1: MeOH/DCM/PhCH$_3$ 1:10:4, column 2: MeOH/DCM/PhCH$_3$ 1:8:1), leading to the isolation of 26 as a pure compound (65 mg, 83%). R$_F$ 0.26 (MeOH/DCM/PhCH$_3$ 1:8:1). $^1$H NMR (CDCl$_3$, 400 MHz): δ 8.79, 8.77, 8.72 (3×d, J=1.9 Hz, 1H), 8.37-8.33 (m, 1H), 8.19-8.15 (m, 1H), 7.65-7.23 (m, 8H), 7.16-7.10 (m, 1H), 6.36-6.27 (m, 1H), 6.11-5.97 (m, 1H), 4.74-3.95 (m, 4H), 3.83-3.47 (m, 10H), 3.29-3.13 (m, 2H), 3.01-2.89 (m, 1H), 2.78-2.48 (m, 2H), 2.36-2.26 (m, 1H), 2.19-1.73 (m, 8H), 1.65-1.52 (m, 2H), 1.26-0.98 (m, 3H) ppm. $^{13}$C NMR (CDCl$_3$, 125 MHz): δ 171.7, 171.3, 170.5, 170.4, 164.4, 164.1, 145.7, 145.6, 145.3, 145.2, 144.9, 144.8, 143.3, 141.2, 139.8, 138.0, 137.7, 136.3, 136.2, 136.1, 135.5, 135.2, 133.4, 133.3, 133.2, 133.1, 132.8, 132.1, 131.9, 131.8, 131.7, 131.5, 131.3, 131.0, 130.5, 130.4, 130.3, 130.1, 129.9, 129.8, 129.7, 129.5, 128.9, 128.7, 128.6, 128.4, 127.9, 127.7, 127.3, 124.8, 124.7, 124.6, 70.6, 70.4, 70.3, 70.1, 69.8, 69.5, 69.3, 68.4, 68.3, 59.7, 52.8, 51.6, 49.1, 48.5, 40.7, 40.5, 35.0, 34.9, 34.2, 34.0, 26.2, 26.1, 23.6, 23.5, 23.4, 23.3, 23.0, 22.8, 22.7, 22.3, 22.2, 21.6, 21.5, 20.1, 20.0, 19.9. HRMS (ESI+) m/z calcd for C$_{43}$H$_{49}$N$_{10}$O$_8$(M+H)$^+$: 833.3735. found: 833.3739. Besides 26 also bis-BCN (6b) and bis-DIBAC (26b) adducts were isolated. Bis-BCN adduct (26+2×6b, 4.0 mg, 6%): R$_f$0.19 (MeOH/DCM/PhCH$_3$ 1:8:1). $^1$H NMR (CDCl$_3$, 400 MHz): δ 8.72 (dd, J=1.8, 1.1 Hz, 1H), 8.41 (dd, J=8.2, 2.0 Hz, 1H), 8.05-8.01 (m, 1H), 7.52 (d, J=8.2 Hz, 1H), 4.47-4.39 (m, 2H), 3.94 (t, J=5.4 Hz, 2H), 3.81-3.53 (m, 12H), 3.26 (ddd, J=15.8, 7.6, 3.2 Hz, 1H), 3.07 (ddd, J=15.7, 7.9, 3.3 Hz, 1H), 3.00-2.93 (m, 2H), 2.85-2.66 (m, 3H), 2.60 (ddd, J=16.1, 10.3, 3.2 Hz), 2.36-2.12 (m, 4H), 1.58-1.47 (m, 3H), 1.25-0.98 (m, 7H) ppm. HRMS (ESI+) m/z calcd for $C_{33}H_{45}N_5O_7$ (M+H)$^+$: 665.3411. found: 665.3439. Bis-DIBAC adduct (26+2×26b, 5 mg, 5%): $R_f$ 0.31 (MeOH/DCM/PhCH$_3$ 1:8:1). $^1$H NMR (CDCl$_3$, 400 MHz): δ 8.77-8.64 (m, 1H), 8.34-8.11 (m, 1H), 8.09 (d, J=1.4 Hz, 1H), 7.92-7.83 (m, 1H), 7.67-6.92 (m, 16H), 6.45-5.89 (m, 2H), 5.56-5.51, 5.03-4.90 (2×m, 1H), 4.76-4.65 (m, 2H), 4.58-4.26 (m, 3H), 4.18-3.92 (m, 1H), 3.82-3.08 (m, 12H), 2.82-2.36 (m, 1H), 2.12-1.73 (m, 8H), 1.33-1.25 (m, 2H) ppm. HRMS (ESI+) m/z calcd for $C_{53}H_{52}N_{12}NaO_9$ (M+Na)$^+$: 1023.3878. found: 1023.3856.

Example 15. Synthesis of 2-azidogalactose 1-Phosphate Derivative (27)

Compound 27 was prepared from D-galactosamine according to the procedure described for D-glucosamine in Linhardt et al., *J. Org. Chem.* 2012, 77, 1449-1456.

$^1$H-NMR (300 MHz, CD$_3$OD): δ 5.69 (dd, J=7.2, 3.3 Hz, 1H), 5.43-5.42 (m, 1H), 5.35 (dd, J=11.1, 3.3 Hz, 1H), 4.53 (t, J=7.2 Hz, 1H), 4.21-4.13 (m, 1H), 4.07-4.00 (m, 1H), 3.82 (dt, J=10.8, 2.7 Hz, 1H), 2.12 (s, 3H), 2.00 (s, 3H), 1.99 (s, 3H) ppm. LRMS (ESI−) calcd for $C_{12}H_{17}N_3O_{11}P$ (M−H$^+$) 410.06. found 410.00.

Example 16. Synthesis of 2-azidogalactose UDP Derivative (28)

Compound 27 was attached to UMP according to Baisch et al. *Bioorg. Med. Chem.*, 1997, 5, 383-391.

Thus, a solution of D-uridine-5'-monophosphate disodium salt (1.49 g, 4.05 mmol) in H$_2$O (15 mL) was treated with DOWEX 50W×8 (H$^+$ form) for 30 minutes and filtered. The filtrate was stirred vigorously at room temperature while tributylamine (0.966 mL, 4.05 mmol) was added dropwise. After 30 minutes of further stirring, the reaction mixture was lyophilized and further dried over P$_2$O$_5$ under vacuum for 5 h.

The resulting tributylammonium uridine-5'-monophosphate was dissolved in dry DMF (25 mL) in an argon atmosphere. Carbonyldiimidazole (1.38 g, 8.51 mmol) was added and the reaction mixture was stirred at r.t. for 30 min. Next, dry MeOH (180 μL) was added and stirred for 15 min to remove the excess carbonyldiimidazole. The leftover MeOH was removed under high vacuum for 15 min. Subsequently, 5'-uridine-monophosphate (UMP, 2.0 g, 4.86 mmol) was dissolved in dry DMF (25 mL) and added dropwise to the reaction mixture. The reaction was allowed to stir at rt for 2 d before concentration in vacuo. The consumption of the imidazole-UMP intermediate was monitored by MS. Flash chromatography (7:2:1-5:2:1 EtOAc:MeOH:H$_2$O) afforded product 28 (1.08 g, 1.51 mmol, 37%).

$^1$H-NMR (300 MHz, D$_2$O): δ 7.96 (d, J=8.0 Hz, 1H), 5.98-5.94 (m, 2H), 5.81-5.79 (m, 1H), 5.70 (dd, J=7.1, 3.3 Hz, 1H), 5.49 (dd, J=15.2, 2.6 Hz, 1H), 5.30 (ddd, J=18.5, 11.0, 3.2 Hz, 2H), 4.57 (q, J=6.0 Hz, 2H), 4.35-4.16 (m, 9H), 4.07-3.95 (m, 2H), 2.17 (s, 3H), 2.08 (s, 3H), 2.07 (s, 3H) ppm.

LRMS (ESI−) calcd for $C_{21}H_{29}N_5O_{19}P_2$(M−H$^+$) 716.09. found 716.3.

Example 17. Synthesis of Deacetylated 2-azidogalactose UDP Derivative (29)

Deacetylation was performed according to Kiso et al., *Glycoconj. J.*, 2006, 23, 565. Thus, compound 28 (222 mg, 0.309 mmol) was dissolved in H$_2$O (2.5 mL) and triethylamine (2.5 mL) and MeOH (6 mL) were added. The reaction mixture was stirred for 3 h and then concentrated in vacuo to afford crude UDP-2-azido-2-deoxy-D-galactose (29). $^1$H-NMR (300 MHz, D$_2$O): δ 7.99 (d, J=8.2 Hz, 1H), 6.02-5.98 (m, 2H), 5.73 (dd, J=7.4, 3.4 Hz, 1H), 4.42-4.37 (m, 2H), 4.30-4.18 (m, 4H), 4.14-4.04 (m, 2H), 3.80-3.70 (m, 2H), 3.65-3.58 (m, 1H) ppm.

LRMS (ESI−) calcd for $C_{15}H_{23}N_5O_{16}P_2$(M−H$^+$) 590.05. found 590.2.

Example 18. Synthesis of UDP-Galactosamine (30)

To a solution of compound 29 in H$_2$O:MeOH 1:1 (4 mL) was added Lindlar's catalyst (50 mg). The reaction was stirred under a hydrogen atmosphere for 5 h and filtered over celite. The filter was rinsed with H$_2$O (10 ml) and the filtrate was concentrated in vacuo to afford the UDP-D-galactosamine (UDP-GalNH$_2$, 30) (169 mg, 0.286 mmol, 92% yield over two steps). $^1$H-NMR (300 MHz, D$_2$O): δ 7.93 (d, J=8.1 Hz, 1H), 5.99-5.90 (m, 2H), 5.76-5.69 (m, 1H), 4.39-4.34 (m, 2H), 4.31-4.17 (m, 5H), 4.05-4.01 (m, 1H), 3.94-3.86 (m, 1H), 3.82-3.70 (m, 3H), 3.30-3.16 (m, 1H). LRMS (ESI−) calcd for $C_{15}H_{25}N_3O_{16}P_2$(M−H$^+$) 564.06. found 564.10.

General Protocol for Synthesis of Activated Esters

To a solution of carboxylic acid was added dicyclohexylcarbodiimide (1.1 equiv) and N-hydroxysuccinimide (1.2 equiv) and the resulting suspension was stirred overnight followed by vacuum filtration. The filtrate was concentrated and dissolved in EtOAc followed by washing with saturated NaHCO$_3$ and brine. The organic layer was dried over Na$_2$SO$_4$, filtered and concentrated in vacuo to use crude in the next reaction.

General Protocol for Attaching Activated Esters to UDP-D-Galactosamine (30)

UDP-D-galactosamine (30) was dissolved in 0.1 M NaHCO$_3$ (0.2 M) and activated ester (2 equiv) dissolved in DMF (0.2 M) was added. The reaction was stirred overnight at r.t. and concentrated in vacuo. Flash chromatography (7:2:1-5:2:1 EtOAc:MeOH:H$_2$O) afforded the product.

Example 19. Synthesis of 4-azido-3,5-difluorobenzoyl Derivative of UDP-GalNH$_2$ (31)

4-Azido-3,5-difluorobenzoic acid succinimidyl ester was prepared according to the procedure for pent-4-ynoic acid succinimidyl ester according to Rademann et al., *Angew. Chem. Int. Ed.*, 2012, 51, 9441-9447.

Thus, to a solution of 4-azido-3,5-difluorobenzoic acid (18) was added dicyclohexylcarbodiimide (1.1 equiv) and N-hydroxysuccinimide (1.2 equiv) and the resulting suspension was stirred overnight followed by vacuum filtration. The filtrate was concentrated and dissolved in EtOAc followed by washing with saturated NaHCO$_3$ and brine. The organic layer was dried over Na$_2$SO$_4$, filtered and concentrated in vacuo to use crude in the next reaction.

$^1$H-NMR (300 MHz, CDCl$_3$): δ 7.74-7.66 (m, 2H), 2.91 (s, 4H).

Next, UDP-GalNH$_2$ (30, 30 mg, 0.0531 mmol) was dissolved in 0.1 M NaHCO$_3$ (0.2 M) and the N-hydroxysuccinimide ester of 18 (31 mg, 0.106 mmol, 2 equiv.), dissolved in DMF (0.2 M), was added. The reaction was stirred overnight at r.t. and concentrated in vacuo. Flash chromatography (7:2:1-5:2:1 EtOAc:MeOH:H$_2$O) afforded the product 31 (8 mg, 0.0107 mmol, 20%).

$^1$H-NMR (300 MHz, D$_2$O): δ 7.73 (d, J=8.4 Hz, 1H), 7.52-7.31 (m, 2H), 5.87-5.71 (m, 2H), 5.65-5.57 (m, 1H), 5.47-5.33 (m, 1H), 4.43-3.96 (m, 8H), 3.76-3.60 (m, 2H).

LRMS (ESI−) calcd for C$_{22}$H$_{25}$F$_2$N$_6$O$_{17}$P$_2$(M−H$^+$) 745.07. found 744.9.

Example 20. Synthesis of 4-azido-2,3,5,6-tetrafluorobenzoyl derivative of UDP-GalNH$_2$ UDP-GalNH$_2$ (30, 41 mg, 0.073 mmol) was dissolved in 0.1 M NaHCO$_3$ (0.2 M) and the N-hydroxysuccinimide ester of 4-azido-2,3,5,6-difluorobenzoic acid (19, commercially available from Iris-Biotech) (47 mg, 0.0.145 mmol, 2 equiv.), dissolved in DMF (0.2 M), was added. The reaction was stirred overnight at r.t. and concentrated in vacuo. Flash chromatography (8:2:1-5:2:1 EtOAc:MeOH:H$_2$O) afforded the 4-azido-2,3,5,6-tetrafluorobenzoyl derivative of UDP-GalNH$_2$.

LRMS (ESI−) calcd for C$_{22}$H$_{23}$F$_4$N$_6$O$_{17}$P$_2$(M−H$^+$) 781.05. found 781.0.

Example 21. Synthesis of 4-(1R,8S,9s)-bicyclo[6.1.0]non-4-yn-9-ylmethyl (4-oxo-4-((pyren-1-ylmethyl)amino)butyl)carbamate (BCN-pyrene (36))

36

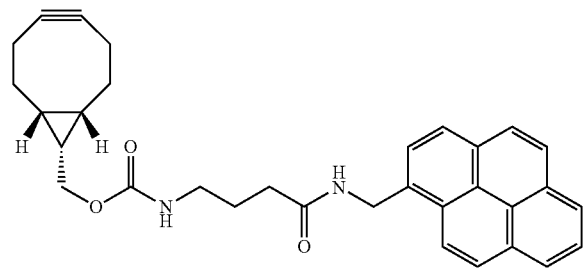

4-(1R,8S,9s)-bicyclo[6.1.0]non-4-yn-9-ylmethoxy)carbonyl)amino)butanoic acid (260 mg, 0.69 mmol) was dissolved in DCM (7 mL) followed by the addition of 1-aminomethyl pyrene HCl (221 mg, 0.83 mmol) and Et$_3$N (143 μL, 1 mmol). The reaction was stirred overnight followed by the addition of water (10 mL) and DCM (10 mL). The organic layer was subsequent washed with saturated aqueous NaHCO$_3$ solution (10 mL) and 0.1 M HCl (10 mL), dried over Na$_2$SO$_4$, filtrated and concentrated under reduced pressure. Purification via flash chromatography (pentane:EtOAc 1:3→1:8) gave the product BCN-pyrene (36) (227 mg, 0.46 mmol, 67%). $^1$H-NMR (400 MHz, CDCl$_3$): δ 8.26-7.95 (m, 9H), 6.34 (bs, 1H), 5.14 (d, J=5.2 Hz, 2H), 4.96 (bs, 1H), 4.05 (d, J=8 Hz, 2H), 3.24-3.19 (m, 2H), 2.28-2.14 (m, 6H), 1.86 (q, J=7.2 Hz, 2H), 1.65-1.62 (m, 1H), 1.53-1.48 (m, 2H), 1.29-1.23 (m, 2H), 0.89-0.85 (m, 2H).

Mass Spectral Analysis of Fabricator-Digested Monoclonal Antibodies

A solution of 20 μg (modified) IgG was incubated for 1 hour at 37° C. with fabricator (commercially available from Genovis, Lund, Sweden) (1.25 U/μL) in phosphate-buffered saline (PBS) pH 6.6 in a total volume of 10 μL. Fabricator-digested samples were washed trice with milliQ using an Amicon Ultra-0.5, Ultracel-10 Membrane (Millipore) resulting in a final sample volume of approximately 40 μL. The Fc/2 fragment was analyzed by electrospray ionization time-of-flight (ESI-TOF) on a JEOL AccuTOF. Deconvoluted spectra were obtained using Magtran software.

Example 22. Preparation of Trimmed Trastuzumab by Endo S Treatment

Glycan trimming of trastuzumab (32) was performed with Endo S from *Streptococcus pyogenes* (commercially available from Genovis, Lund, Sweden). Thus, trastuzumab (10 mg/mL) was incubated with endo S (40 U/mL) in 25 mM Tris pH 8.0 for approximately 16 hours at 37° C. The deglycosylated IgG was concentrated and washed with 10 mM MnCl$_2$ and 25 mM Tris-HCl pH 8.0 using an Amicon Ultra-0.5, Ultracel-10 Membrane (Millipore).

After deconvolution of peaks, the mass spectrum showed one peak of the light chain and two peaks of the heavy chain. The two peaks of heavy chain belonged to one major product (49496 Da, 90% of total heavy chain), resulting from core GlcNAc(Fuc) substituted trastuzumab, and a minor product (49351 Da, +10% of total heavy chain), resulting from deglycosylated trastuzumab.

Figure 8:
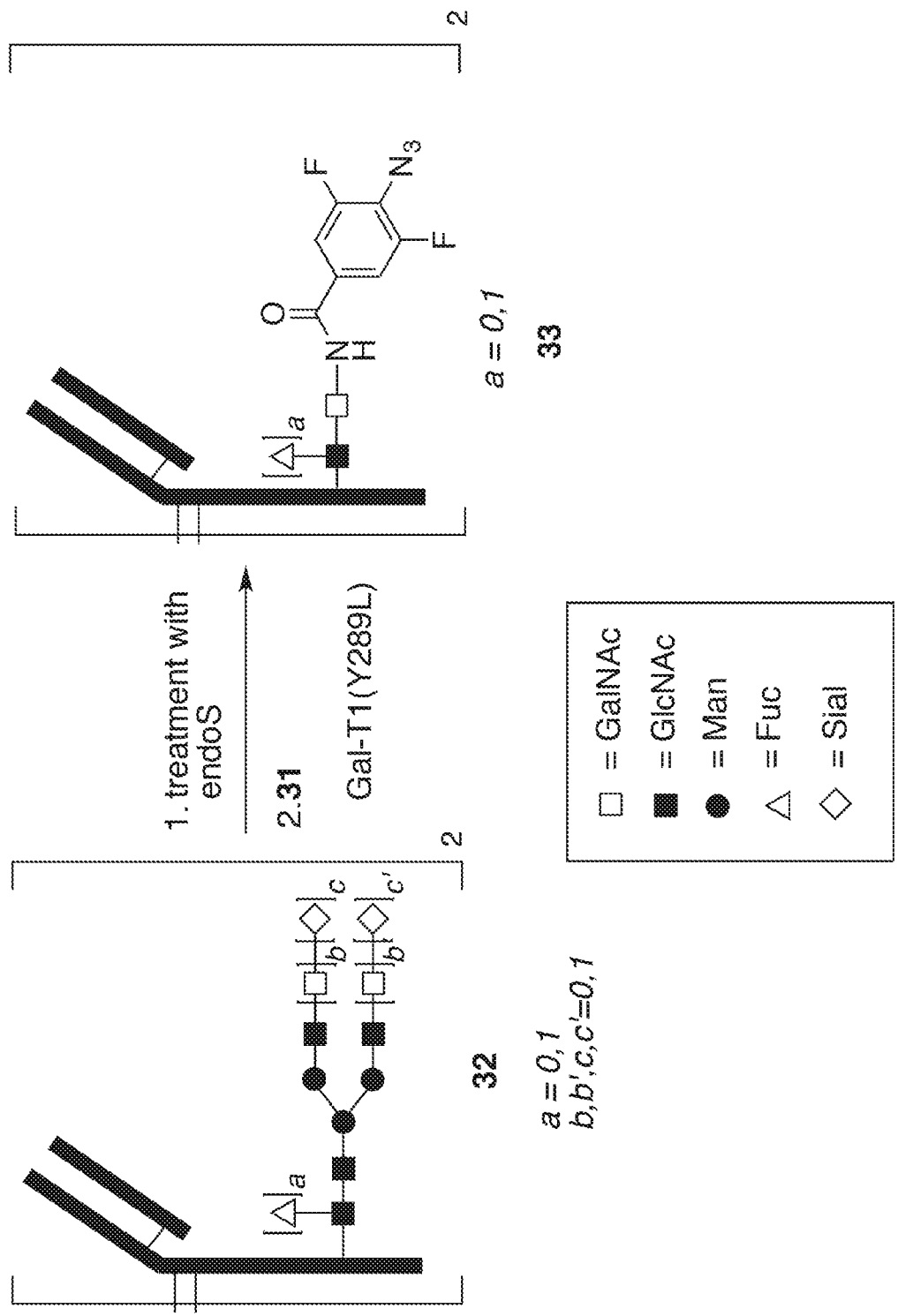
FIG. 8 shows the schematic scheme for the transfer of the modified UDP-GalNAryl substrate 31 onto the core N-GlcNAc of antibody 32 upon subjecting antibody consecutively to trimming with endoS, then GalT(Y289L), leading to modified antibodies 33.

Example 23. Protocol for Glycosyltransfer of Galactosamine Derivative UDP-GalNAz with Gal-T (Y289L). See FIG. 8

Enzymatic introduction of UDP-GalNAz (Carbosynth, Compton, Berkshire, UK) onto trimmed trastuzumab was effected with Gal-T1(Y289L), which is the catalytic domain consisting of residues 130-402 of a mutant of bovine β(1, 4)-galactosyltransferase [β(1,4)-Gal-T1] with the Y289L and C342T mutations. GalT(Y289L) was expressed, isolated and refolded from inclusion bodies according to the reported procedure by Qasba et al. (*Prot. Expr. Pur.* 2003, 30, 219-76229). Trimmed trastuzumab (10 mg/mL) was incubated with 31 (0.7 mM) and Gal-T1(Y289L) (2 mg/mL) in 10 mM MnCl$_2$ and 25 mM Tris-HCl pH 8.0 at 30° C. overnight. Next, the functionalized trastuzumab was incubated with protein A agarose (40 μL per mg IgG) for 2 hours at 4° C. The protein A agarose was washed three times with PBS and the IgG was eluted with 100 mM glycine-HCl pH 2.7. The eluted IgG was neutralized with 1 M Tris-HCl pH 8.0 and concentrated and washed with PBS using an Amicon Ultra-0.5, Ultracel-10 Membrane (Millipore) to a concentration of 15-20 mg/mL.

Mass spectral analysis of the reduced sample indicated the formation of a one major product (49813 Da, approximately 90% of total heavy chain), resulting from transfer of 31 to core GlcNAc(Fuc)-substituted trastuzumab heavy chain.

Example 24. Glycosyltransfer of 4-azido-3,5-difluorobenzoyl Derivative of UDP-galactosamine to Trimmed Trastuzumab Under the Action of Gal-T (Y289L)

Trimmed trastuzumab (10 mg/mL, 66 μM), obtained by endo S treatment of trastuzumab, was incubated with the 4-azido-3,5-difluorobenzoyl derivative of UDP-galactosamine (31, 1 mM) and Gal-T1(Y289L) (1.0 mg/mL) in 10 mM MnCl2 and 25 mM Tris-HCl pH 8.0 at 30° C. overnight. Mass spectral analysis of the reduced sample indicated a complete conversion of core GlcNac(Fuc)-substituted trastuzumab (observed mass 49502 Da, calculated mass of 49506 Da for the heavy chain) into trast(F$_2$-GalNBAz)$_2$ 33 (observed mass 49818 Da, calculated mass of 49822 Da for the heavy chain), resulting from transfer of 31 to core GlcNAc(Fuc)-substituted trastuzumab heavy chain followed by reduction of the azide during sample preparation.

Example 25. Glycosyltransfer of 4-Azido-2,3,5,6-Tetrafluorobenzoyl Derivative of UDP-Galactosamine to Trimmed Trastuzumab Under the Action of Gal-T1(Y289L)

Trimmed trastuzumab (10 mg/mL, 66 µM), obtained by endo S treatment of trastuzumab, was incubated with the 4-azido-2,3,5,6-tetrafluorobenzoyl derivative of UDP-galactosamine (1 mM) and Gal-T1(Y289L) (1.0 mg/mL) in 10 mM MnCl2 and 25 mM Tris-HCl pH 8.0 at 30° C. overnight. Mass spectral analysis of the fabricator-digested sample indicated a partial conversion of core GlcNac(Fuc)-substituted trastuzumab (observed mass 24139 Da, calculated mass of 24136 Da) into trast($F_4$-GalNBAz)$_2$ (observed mass 24518 Da, calculated mass of 24514 Da, approximately 10% of total Fc/2 fragment), resulting from transfer of the 4-azido-2,3,5,6-tetrafluorobenzoyl derivative of UDP-galactosamine to core GlcNAc(Fuc)-substituted trastuzumab.

Example 26. Conjugation of trast($F_2$-GalNBAz)$_2$ 33 with BCN-pyrene

Trast($F_2$-GalNBAz)$_2$ 33 (15 mg/mL, 100 µM) was incubated with BCN-pyrene 36 (1 mM) in phosphate-buffered saline (PBS) pH 7.4 with 50% DMA at room temperature overnight. Mass spectral analysis of the fabricator-digested sample indicated a complete conversion of Trast($F_2$-GalNBAz)$_2$ 33 (observed mass 24481 Da, calculated mass of 24479 Da) into the corresponding triazole derivative with BCN-pyrene (observed mass 24975 Da, calculated mass of 24971 Da).

Example 27. Conjugation of trast($F_4$-GalNBAz)$_2$ with BCN-pyrene

Trast($F_4$-GalNBAz)$_2$ 33 (15 mg/mL, 100 µM) was incubated with BCN-pyrene 36 (1 mM) in phosphate-buffered saline (PBS) pH 7.4 with 50% DMA at room temperature overnight. Mass spectral analysis of the fabricator-digested sample indicated a complete conversion of Trast($F_4$-GalNBAz)$_2$ (observed mass 24518 Da, calculated mass of 24514 Da) into the corresponding triazole derivative with BCN-pyrene (observed mass 25009 Da, calculated mass of 25006 Da).

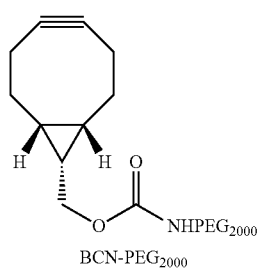

BCN-PEG$_{2000}$ (38)

Example 28. Conjugation of trast-(GalNAz)$_2$ and trast($F_2$-GalNBAz)$_2$ 33 with BCN-PEG$_{2000}$ 38 at Variable Concentrations of BCN-PEG$_{2000}$ Trast-(GalNAz)$_2$ or trast-($F_2$-GalNBAz)$_2$ (33) (10 µM IgG) in PBS were incubated overnight at room temperature with 0 to 20 equivalents of BCN-PEG$_{2000}$ (38) (0 to 200 µM). Reaction products were separated by reducing SDS-PAGE followed by coomassie staining.

Figure 9:
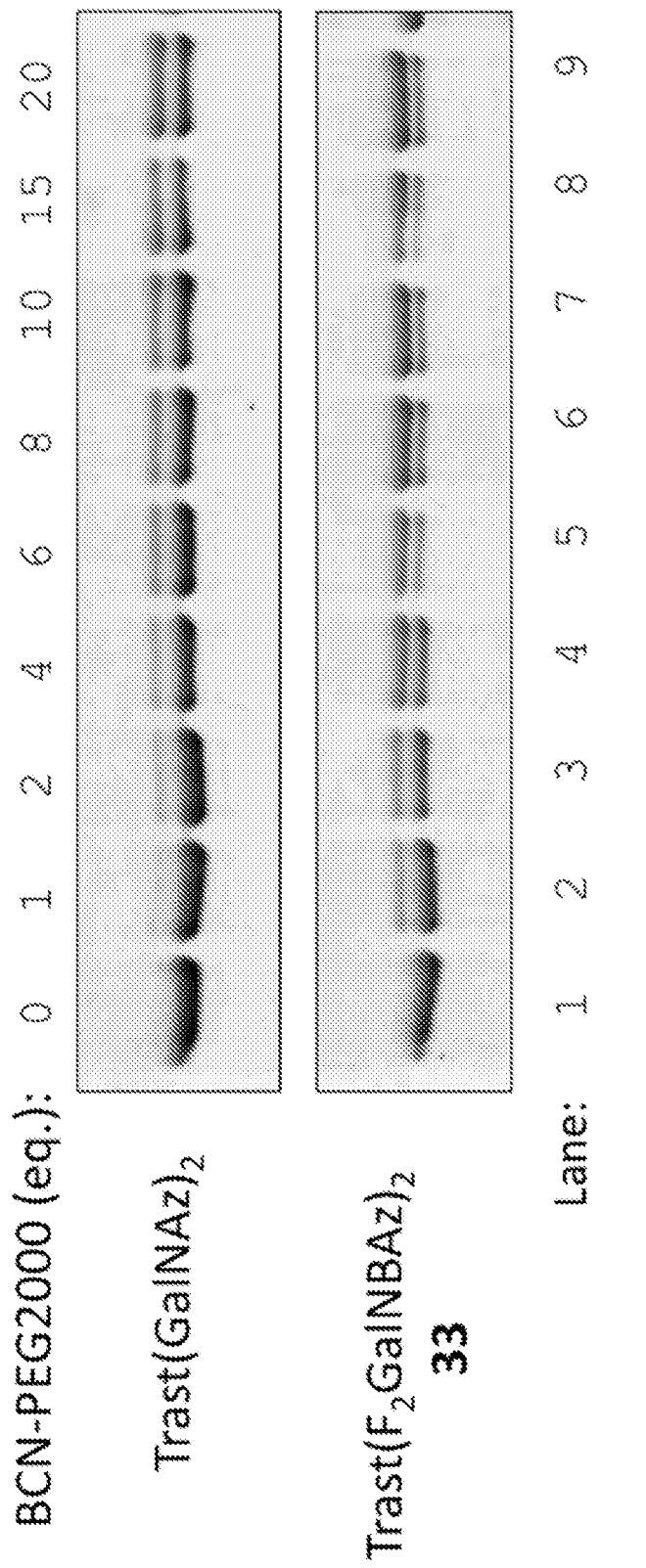
FIG. 9 shows the SDS-PAGE of the heavy chain of deglycosylated azido-derivative of trastuzumab modified with N-azidoacetyl-D-galactosamine (trast-(GalNAz)$_2$, top gel) and 33 (trast-(GalNBAz)$_2$, lower gel) before conjugation to BCN-PEG$_{2000}$ (lower band in gel) and after conjugation to BCN-PEG$_{2000}$ (upper band in gel).
Figure 10:
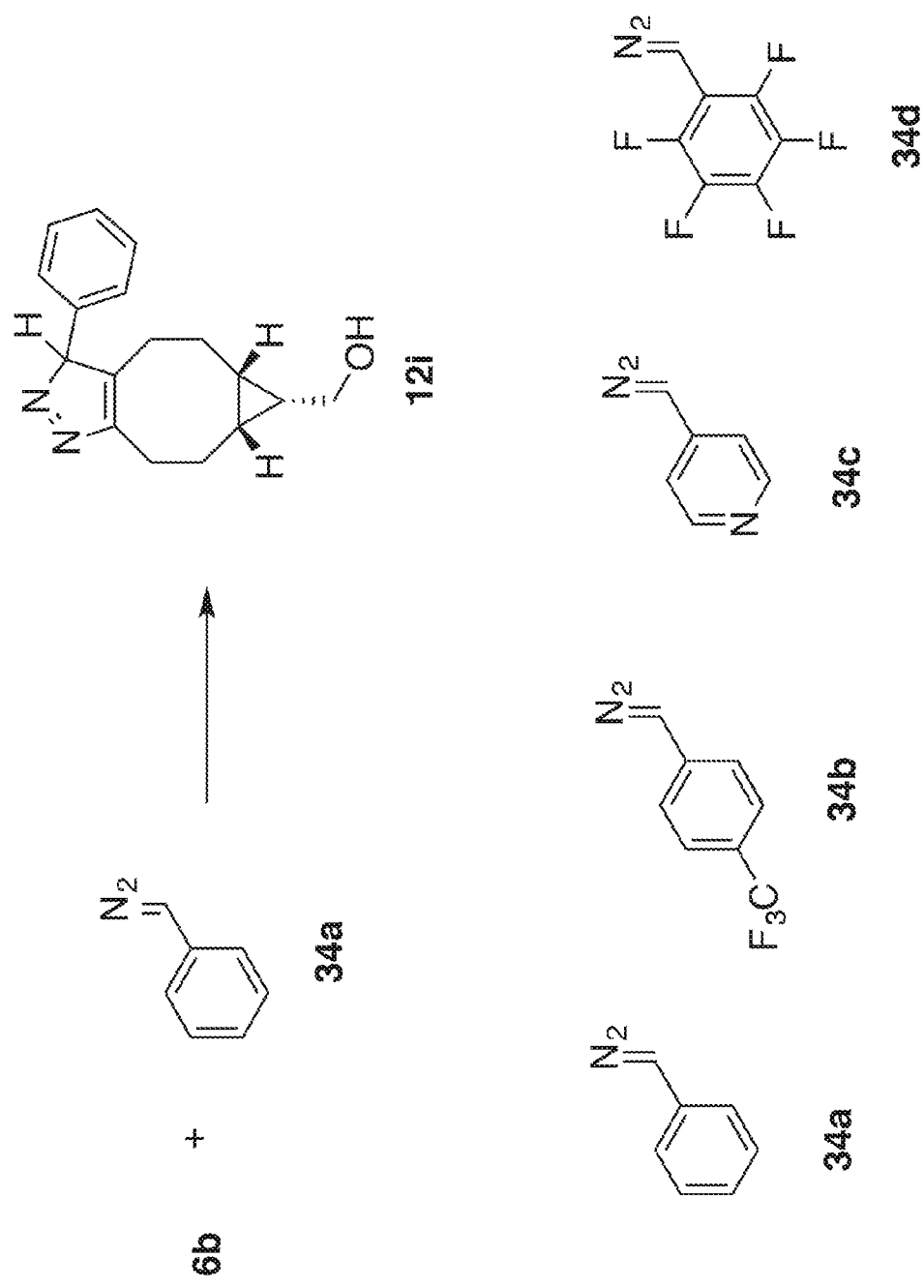
FIG. 10 shows the schematic scheme for strain-promoted cycloaddition of diazomethylbenzene (34a) with BCN-derivative 6b, leading to cycloadduct 12i. Also shown are the structures of diazo-compounds 34b, 34c and 34d.

FIG. 9 shows the heavy chain of trastuzumab-(GalNAz)$_2$ (top panel) and trastuzumab-($F_2$-GalNBAz)$_2$ 33 (lower panel) before conjugation to BCN-PEG$_{2000}$ (lower band) and after conjugation to BCN-PEG$_{2000}$ (upper band). Trast-(GalNAz)$_2$ shows less than 50% conversion when incubated with 20 equivalents BCN-PEG$_{2000}$ (upper panel, lane 9) while trast-($F_2$-GalNBAz)$_2$ shows >50% conversion when incubated with only 4 equivalents BCN-PEG$_{2000}$ (lower panel, lane 4).

Example 29. Reaction Speed Comparison for Phenyl Azide and Azides (3zh-Zk) with BCN-pyrene 36

In a sample jar BCN-pyrene stock (20 µL of a 10 mM stock solution in DMF) was added to MeCN (550 µL) and subsequently H$_2$O (325 µL) and azide (100 µL of a stock solution of 10 mM azide in MeCN) were added (final concentration 0.2 mM BCN-pyrene, 1 mM azide). The reaction was incubated at room temperature and at indicated time points a HPLC measurement (with a Phenomenex Luna 5u C18 column and H$_2$O/MeCN+0.1% TFA as eluens) was performed. The intensity of the peaks of the product and starting material at 340 nm were used to calculate the conversion.

TABLE 4

Time-resolved conversion of BCN-pyrene upon incubation with excess (5 equiv.) of azide 3zh-3zk.

| Time (min) | Phenyl azide | 3zh | 3zi | 3zj | 3zk |
|---|---|---|---|---|---|
| 15 | 41% | 56% | 58% | 58% | 66% |
| 35 | 63% | 79% | 85% | 85% | 92% |

From Table 4, it becomes clear that azides 3zh-3zk in all cases display an accelerated reaction rate for cycloaddition with BCN-pyrene with respect to phenyl azide.

Example 30. Reaction Speed Comparison for Phenyl Azide and Azide 3zl with Cyclooctyne In a sample jar cyclooctyne (50 µL of a 100 mM stock solution in DMF) was added to MeCN (533 µL) and subsequently H$_2$O (316 µL) and azide (100 µL of a 10 mM stock solution of azide in MeCN) were added (final concentration 5 mM cyclooctyne, 1 mM azide). The reaction was incubated at room temperature and at indicated time points a HPLC measurement (with a Phenomenex Luna 5u C18 column and H$_2$O/MeCN+0.1% TFA as eluens) was performed. The intensity of the peaks of the product and starting material at 340 nm were used to calculate the conversion.

TABLE 5

Time-resolved conversion of phenyl azide or azide 3zl upon incubation with excess cyclooctyne (5 equiv).

| Time (min) | Phenyl azide | 3zl |
|---|---|---|
| 50 | 0% | 28% |
| 105 | 9% | 78% |
| 240 | 23% | 94% |

From Table 5, it becomes clear that 3zl displays a significantly accelerated reaction rate (>3 times faster) for cycloaddition with cyclooctyne with respect to phenyl azide.

Example 31. Reaction Speed Comparison for Phenyl Azide and Azide 3zl with COMBO In a sample jar COMBO (as its free carboxylate (37), 25 μL from a 10 mM stock solution in DMF) was added to MeCN (140 μL) and subsequently, H₂O (70 μL) and azide (5 μL of 10 mM stock solution of azide in MeCN) were added (final concentration 1 mM COMBO, 0.2 mM azide, approximately 5 equivalents COMBO with respect to azide). The reaction was incubated at room temperature and at indicated time points a HPLC measurement (with a Phenomenex Luna 5u C18 column and H₂O/MeCN+0.1% TFA as eluens) was performed. The intensity of the peaks of the product and starting material at 340 nm were used to calculate the conversion.

TABLE 6

Time-resolved conversion of phenyl azide or azide 3zl upon incubation with excess COMBO-derivative 37 (5 equiv).

| Time (min) | Phenyl azide | 3zl |
|---|---|---|
| 15 | 27% | 80% |
| 45 | 53% | 90% |

From Table 6, it becomes clear that 3zl displays a significantly accelerated reaction rate (2-3 times faster) for cycloaddition with COMBO-derivative 37 with respect to phenyl azide.

Example 32. Synthesis of 2,4,6-triisopropylbenzenesulfonyl Hydrazone of Benzaldehyde 2,4,6-Triisopropylbenzenesulfonyl hydrazine (300 mg, 1 mmol) was dissolved in methanol (10 mL) followed by the addition of benzaldehyde (102 μL, 1 mmol). A white precipitate was formed after 5 minutes, the reaction was stirred for 1 h followed by filtration. The precipitate was dried under vacuum to yield the product (233 mg. 0.6 mmol, 60%) which was used crude in the next reaction. ¹H-NMR (400 MHz, DMSO-d6): 10.88 (bs, 1H), 7.63 (s, 1H), 7.30-7.26 (m, 2H), 7.05-7.03 (m, 3H), 6.89 (m, 2H), 4.09-4.04 (m, 2H), 2.70-2.61 (m, 1H), 1.03-1.01 (m, 12H), 0.99-0.97 (m, 6H) ppm.

Example 33. Synthesis of 2,4,6-triisopropylbenzenesulfonyl Hydrazone of 4-(trifluoromethyl)-benzaldehyde 2,4,6-Triisopropylbenzenesulfonyl hydrazine (300 mg, 1 mmol) was dissolved in methanol (10 mL) followed by the addition of 4-(trifluoromethyl)benzaldehyde (172 mg, 1 mmol). A white precipitate was formed after 5 minutes, the reaction was stirred for 1 h followed by filtration. The precipitate was dried under vacuum to yield the product (237 mg. 0.59 mmol, 59%) which was used crude in the next reaction. ¹H-NMR (400 MHz, DMSO-d6): 11.47 (bs, 1H), 7.92-7.89 (m, 1H), 7.67-7.51 (m, 4H), 7.18-7.13 (m, 2H), 4.32-4.27 (m, 2H), 2.91-2.87 (m, 1H), 1.32-1.20 (m, 18H) ppm.

Example 34. Protocol for the Generation of Diazo Compounds 3zd or 3Ze

To a suspension of an appropriate 2,4,6-triisopropylbenzenesulphonyl hydrazone in methanol (0.1 M) was added KOH (2 equiv) and the reaction was heated to 50° C. for until full disappears of the starting material was observed on TLC (about 10 min). The clear solution (dark red) was quenched with water (2 mL) and subsequently extracted with DCM (2×1 mL). The combined organic layers were kept in the dark and used without further purification in the cycloaddition reactions.

Example 35. Synthesis of Cyclooctyne

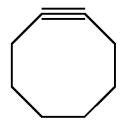

Synthesis according to procedure described in: L. Brandsma, H. D. Verkruijsse, Synthesis, 1978, 290.

Example 36. Synthesis of Benzo-Annulated Cyclooctyne (COMBO) 37

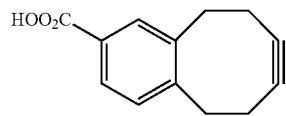

Synthesis according to a procedure described in B. R. Varga, M. Kállay, K. Hegyi, S. Béni, P. Kele, Chem. Eur. J. 2012, 18, 822-828.

In the last step of the synthesis the benzoic acid derivative of COMBO was obtained instead of COMBO-methyl ester. Followed procedure: 18-crown-6 (27 mg, 0.10 mmol) was placed under a nitrogen atmosphere. Hexane (30 mL) and KOtBu (75 mg, 0.67 mmol) were added and the resulting mixture was heated to 59° C. A solution of (E)-methyl 8-bromo-5,6,9,10-tetrahydrobenzo[8]annulene-2-carboxylate (79 mg, 0.27 mmol) in hexane (12 mL) and dichloromethane (3 mL) was added, followed by addition of 1 mL of dichloromethane. The reaction mixture was stirred for 30 min before extra KOtBu was added (1M solution in THF, 0.67 mL, 0.67 mmol). After 20 min, saturated aqueous NH₄Cl (50 mL) and EtOAc (50 mL) were added. After separation, the aqueous phase was extracted with EtOAc (50 mL). The combined organics were dried (Na₂SO₄) and concentrated. The residue was purified by column chromatography (EtOAc in heptane 0→20%), followed by reversed phase HPLC (C18, 5→95% MeCN in water (0.1% formic acid). The product containing fractions were pooled, neutralized with saturated aqueous NaHCO₃ and extracted with dichloromethane (30 mL). After separation, the organic phase was washed with sat. aqueous NH₄Cl, dried (Na₂SO₄) and concentrated. The product was obtained as a colourless film (16 mg, 0.074 mmol, 27%). ¹H NMR data were in accordance with literature data. 1H NMR (400 MHz, CDCl₃): δ 7.95-7.91 (m, 2H), 7.28 (d, J=8.5 Hz, 1H), 3.47 (q, J=12.1 Hz, 2H), 2.92 (t, J=14.0 Hz, 2H), 2.54-2.45 (m, 2H), 2.37-2.28 (m, 2H) ppm.

Example 37. Synthesis of Benzo-Annulated Cyclononynone 35a

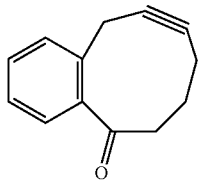 [SMILES: O=C1CCCC#CCc2ccccc21]

Synthesis according to procedure described in J. Tummatorn, G. B. Dudley, *Org. Lett.* 2011, 13, 1572-1575.

$^1$H-NMR (400 MHz, CDCl$_3$): δ 7.28-7.23 (m, 2H), 7.18-7.15 (m, 2H), 3.91 (br s, 1H), 3.22 (br s, 1H), 2.84 (br s, 1H); 2.71 (br s, 2H), 2.23 (br s, 2H), 2.08 (br s, 1H) ppm.

The invention claimed is:

1. A compound according to Formula (12):

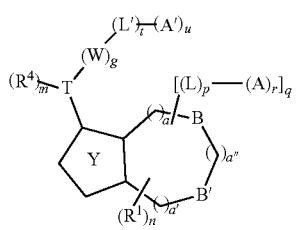

wherein:
a is 1, 2, 3 or 4;
a' is 1, 2, 3 or 4;
a" is 1, 2, 3 or 4;
with the proviso that a+a'+a"=4; and
n is 0-8; or
a is 1, 2, 3, 4 or 5;
a' is 1, 2, 3, 4 or 5;
a" is 1, 2, 3, 4 or 5;
with the proviso that a+a'+a"=5; and
n is 0-10;
each atom of ring Y is selected from C, N, and O atoms and the ring is selected from the group consisting of

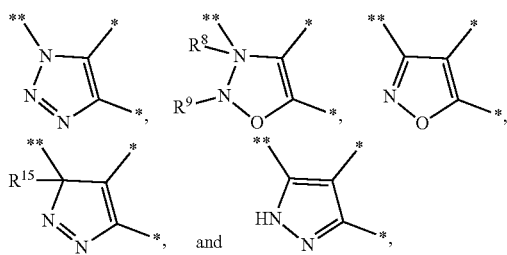

wherein ** is the connection to T and * are the connections to the fused ring containing B and B';

R$^1$ is independently selected from the group consisting of —OR$^2$, —NO$_2$, —CN, —S(O)$_2$R$^2$, C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups, wherein the alkyl groups, cycloalkyl groups, (hetero)aryl groups, alkyl(hetero) aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein R$^2$ is independently selected from the group consisting of hydrogen, halogen, C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups;

B and B' are independently selected from the group consisting of O, S, C(O), NR$^3$ and C(R$^3$)$_2$, wherein R$^3$ is independently selected from the group consisting of hydrogen, R$^1$ or (L)$_p$-(A)$_r$;

optionally, when n is 2 or more, two R$^1$ groups may together form a (hetero)cycloalkyl group, the (hetero)cycloalkyl group optionally being substituted with an (L)$_p$-(A)$_r$ substituent;

optionally, when a" is 2 or more and n is 2 or more, two R$^1$ groups present on adjacent a"-C-atoms may together form a (hetero)aryl group, the (hetero)aryl group optionally being substituted with an (L)$_p$-(A)$_r$ substituent;

p is 0 or 1;
r is 1-4;
L is a linker;
A and A' are independently selected from the group consisting of D, E and Q, wherein D, E and Q are as defined below;
q is 0-4;

with the proviso that if q is 0, then B and/or B' is NR$^3$ wherein R$^3$ is (L)$_p$-(A)$_r$, and/or B and/or B' is C(R$^3$)$_2$ wherein one or more R$^3$ is (L)$_p$-(A)$_r$, and/or n is 2 or more and two R$^1$ groups together form a (hetero) cycloalkyl group wherein the (hetero)cycloalkyl group is substituted with an (L)$_p$-(A)$_r$ substituent, and/or a" is 2 or more and n is 2 or more and two R$^1$ groups present on adjacent a"-C-atoms together form a (hetero)aryl group wherein the (hetero)aryl group is substituted with an (L)$_p$-(A)$_r$ substituent;

t is 0 or 1;
u is 1-4;
g is 0 or 1;
m is 0-8;

with the proviso that when m is 0, then T is an electron-poor (hetero)aryl group, wherein an electron-poor (hetero)aryl group is:
(a) a (hetero)aryl group wherein the (hetero)aromatic ring system is bearing a positive charge, and/or
(b) a (hetero)aryl group wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring;

L' is a linker;
T is selected from the group consisting of (hetero)aryl groups;
R$^4$ is independently selected from the group consisting of electron-withdrawing substituents having a positive value for the para-Hammett substituent constant σ$_p$ and/or the meta-Hammett substituent constant σ$_m$;
W is selected from the group consisting of C$_1$-C$_{24}$ alkylene groups, C$_2$-C$_{24}$ alkenylene groups, C$_3$-C$_{24}$ cycloalkylene groups, C$_2$-C$_{24}$ (hetero)arylene groups, C$_3$-C$_{24}$ alkyl(hetero)arylene groups and C$_3$-C$_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N;

$R^8$ is selected from the group consisting of hydrogen, $C_1$-$C_{12}$ alkyl groups and $(L'')_i A''$, wherein $L''$ is as defined for $L'$, $A''$ is as defined for $A'$, i is 0 or 1, wherein $L''$ is selected independently from $L'$ and $L'''$ and wherein $A''$ is selected independently from $A'$ and $A'''$;

$R^9$ is selected from the group consisting of $C_1$-$C_{12}$ alkyl groups and $(L''')_w A'''$, wherein $L'''$ is as defined for $L'$, $A'''$ is as defined for $A'$, w is 0 or 1, wherein $L'''$ is selected independently from $L'$ and $L''$ and wherein $A'''$ is selected independently from $A'$ and $A''$;

optionally $R^8$ and $R^9$ may together form a (hetero)cycloalkyl group, the (hetero)cycloalkyl group optionally being substituted;

$R^{15}$ is selected from the group consisting of hydrogen, $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N;

D is a molecule of interest;
E is a solid surface; and
Q is a functional group.

2. The compound according to claim 1, wherein the compound is according to Formula (12a):

wherein:
a' is 1, 2, 3 or 4;
a" is 1, 2, 3 or 4;
with the proviso that a+a'+a"=4; and
n is 0-8; or
when the (hetero)cycloalkyne is a (hetero)cyclononyne:
a is 1, 2, 3, 4 or 5;
a' is 1, 2, 3, 4 or 5;
a" is 1, 2, 3, 4 or 5;
with the proviso that a+a'+a"=5; and
n is 0-10;

$R^1$ is independently selected from the group consisting of —$OR^2$, —$NO_2$, —CN, —$S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein $R^2$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups;

B and B' are independently selected from the group consisting of O, S, C(O), $NR^3$ and $C(R^3)_2$, wherein $R^3$ is independently selected from the group consisting of hydrogen, $R^1$ or $(L)_p$-$(A)_r$;

optionally, when n is 2 or more, two $R^1$ groups may together form a (hetero)cycloalkyl group, the (hetero)cycloalkyl group optionally being substituted with an $(L)_p$-$(A)_r$ substituent;

optionally, when a" is 2 or more and n is 2 or more, two $R^1$ groups present on adjacent a"-C-atoms may together form a (hetero)aryl group, the (hetero)aryl group optionally being substituted with an $(L)_p$-$(A)_r$ substituent;

p is 0 or 1;
r is 1-4;
L is a linker;
A is independently selected from the group consisting of D, E and Q, wherein D is a molecule of interest, E is a solid surface, and Q is a functional group;
q is 0-4;
t is 0 or 1;
u is 1-4;
g is 0 or 1;
m is 0-8;

with the proviso that when m is 0, then T is an electron-poor (hetero)aryl group, wherein an electron-poor (hetero)aryl group is:
(ii-a) a (hetero)aryl group wherein the (hetero)aromatic ring system is bearing a positive charge, and/or
(ii-b) a (hetero)aryl group wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring;

L' is a linker;
A' is independently selected from the group consisting of D, E and Q, wherein D is a molecule of interest, E is a solid surface, and Q is a functional;
T is selected from the group consisting of (hetero)aryl groups;
$R^4$ is independently selected from the group consisting of electron-withdrawing substituents having a positive value for the para-Hammett substituent constant $\sigma_p$ and/or the meta-Hammett substituent constant $\sigma_m$;
W is selected from the group consisting of $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl (hetero)arylene groups and (hetero)arylalkylene groups are optionally interrupted by one or more heteroatoms selected from the group consisting of O, S and N; and
$R^{15}$ is selected from the group consisting of hydrogen, $C_1$-$C_{24}$ alkyl groups, $C_2$-$C_{24}$ alkenyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkenyl groups, cycloalkyl groups, (hetero)aryl groups, alkyl(hetero)aryl groups and (hetero)arylalkyl groups are optionally substituted, and wherein the alkyl groups, alkenyl groups, cycloalkyl groups, (hetero)aryl groups, alkyl(hetero)aryl groups and (hetero)arylalkyl groups are optionally interrupted by one or more heteroatoms selected from the group consisting of O, S and N.

3. The compound according to claim 1, wherein the compound is according to Formula (13a):

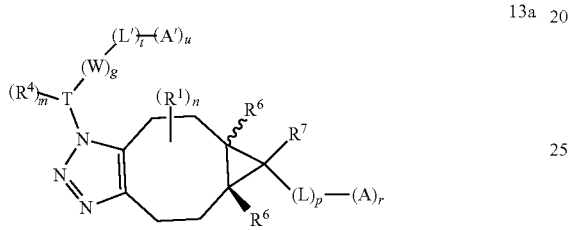

13a wherein:
$R^1$ is independently selected from the group consisting of —$OR^2$, —$NO_2$, —CN, —$S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein $R^2$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups;
optionally, when n is 2 or more, two $R^1$ groups may together form a (hetero)cycloalkyl group, the (hetero)cycloalkyl group optionally being substituted with an $(L)_p$-$(A)_r$ substituent;
optionally, when a" is 2 or more and n is 2 or more, two $R^1$ groups present on adjacent a"-C-atoms may together form a (hetero)aryl group, the (hetero)aryl group optionally being substituted with an $(L)_p$-$(A)_r$ substituent;
p is 0 or 1;
r is 1-4;
L is a linker;
q is 0-4;
t is 0 or 1;
u is 1-4;
g is 0 or 1;
n is 0-8;
m is 0-8;
with the proviso that when m is 0, then T is an electron-poor (hetero)aryl group, wherein an electron-poor (hetero)aryl group is:

(ii-a) a (hetero)aryl group wherein the (hetero)aromatic ring system is bearing a positive charge, and/or
(ii-b) a (hetero)aryl group wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring;
L' is a linker;
A and A' are independently selected from the group consisting of D, E and Q, wherein D is a molecule of interest, E is a solid surface, and Q is a functional;
T is selected from the group consisting of (hetero)aryl groups;
$R^4$ is independently selected from the group consisting of electron-withdrawing substituents having a positive value for the para-Hammett substituent constant $\sigma_p$ and/or the meta-Hammett substituent constant $\sigma_m$;
W is selected from the group consisting of $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N;
$R^6$ is independently selected from the group consisting of hydrogen, halogen, $C_1$-$C_{24}$ alkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkyl(hetero)aryl groups and (hetero)arylalkyl groups optionally are independently optionally interrupted by one of more hetero-atoms selected from the group consisting of O, N and S, and wherein the alkyl groups, (hetero)aryl groups, alkyl(hetero)aryl groups and (hetero)arylalkyl groups are independently optionally substituted;
$R^7$ is selected from the group consisting of hydrogen, $(L)_p$-$(A)_r$, halogen, $C_1$-$C_{24}$ alkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkyl(hetero)aryl groups and (hetero)arylalkyl groups optionally are independently optionally interrupted by one of more hetero-atoms selected from the group consisting of O, N and S, and wherein the alkyl groups, (hetero)aryl groups, alkyl(hetero)aryl groups and (hetero)arylalkyl groups are independently optionally substituted; and
$R^{15}$ is selected from the group consisting of hydrogen, $C_1$-$C_{24}$ alkyl groups, $C_2$-$C_{24}$ alkenyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkenyl groups, cycloalkyl groups, (hetero)aryl groups, alkyl(hetero)aryl groups and (hetero)arylalkyl groups are optionally substituted, and wherein the alkyl groups, alkenyl groups, cycloalkyl groups, (hetero)aryl groups, alkyl(hetero)aryl groups and (hetero)arylalkyl groups are optionally interrupted by one or more heteroatoms selected from the group consisting of O, S and N.

4. The compound according to claim 1, wherein the compound is according to Formula (14a):

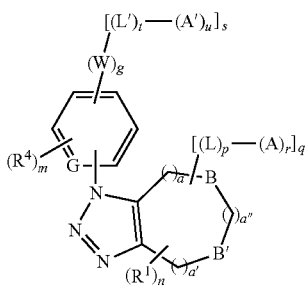

wherein:
a' is 1, 2, 3 or 4;
a" is 1, 2, 3 or 4;
with the proviso that a+a'+a"=4; and
n is 0-8; or
when the (hetero)cycloalkyne is a (hetero)cyclononyne:
a is 1, 2, 3, 4 or 5;
a' is 1, 2, 3, 4 or 5;
a" is 1, 2, 3, 4 or 5;
with the proviso that a+a'+a"=5; and
n is 0-10;
$R^1$ is independently selected from the group consisting of $-OR^2$, $-NO_2$, $-CN$, $-S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero) aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein $R^2$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups;
B and B' are independently selected from the group consisting of O, S, C(O), $NR^3$ and $C(R^3)_2$, wherein $R^3$ is independently selected from the group consisting of hydrogen, $R^1$ or $(L)_p$-$(A)_r$;
optionally, when n is 2 or more, two $R^1$ groups may together form a (hetero)cycloalkyl group, the (hetero) cycloalkyl group optionally being substituted with an $(L)_p$-$(A)_r$ substituent;
optionally, when a" is 2 or more and n is 2 or more, two $R^1$ groups present on adjacent a"-C-atoms may together form a (hetero)aryl group, the (hetero)aryl group optionally being substituted with an $(L)_p$-$(A)_r$ substituent;
p is 0 or 1;
r is 1-4;
L is a linker;
A is independently selected from the group consisting of D, E and Q, wherein D is a molecule of interest, E is a solid surface, and Q is a functional group;
q is 0-4;
t is 0 or 1;
u is 1-4;
g is 0 or 1;
m is 0-8;

with the proviso that when m is 0, then T is an electron-poor (hetero)aryl group, wherein an electron-poor (hetero)aryl group is:
(ii-a) a (hetero)aryl group wherein the (hetero)aromatic ring system is bearing a positive charge, and/or
(ii-b) a (hetero)aryl group wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring;
L' is a linker;
A' is independently selected from the group consisting of D, E and Q, wherein D is a molecule of interest, E is a solid surface, and Q is a functional group;
$R^4$ is independently selected from the group consisting of electron-withdrawing substituents having a positive value for the para-Hammett substituent constant $\sigma_p$ and/or the meta-Hammett substituent constant $\sigma_m$;
W is selected from the group consisting of $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero) arylene groups, alkyl(hetero)arylene groups and (hetero)arylalkylene groups are optionally substituted, and wherein the alkylene groups, alkenylene groups, cycloalkylene groups, (hetero)arylene groups, alkyl (hetero)arylene groups and (hetero)arylalkylene groups are optionally interrupted by one or more heteroatoms selected from the group consisting of O, S and N;
s is 0 or 1;
G is independently selected from the group consisting of N, CH, $CR^4$, $CR^5$, $C-(W)_g$-$[(L')_t$-$(A')_u]$, $N^+R^5$ and $N^+(W)_g$-$[(L)_r$-$(A)_u]$, wherein $R^5$ is selected from the group consisting of $C_1$-$C_{24}$ alkyl groups; and
$R^{15}$ is selected from the group consisting of hydrogen, $C_1$-$C_{24}$ alkyl groups, $C_2$-$C_{24}$ alkenyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkenyl groups, cycloalkyl groups, (hetero)aryl groups, alkyl(hetero) aryl groups and (hetero)arylalkyl groups are optionally substituted, and wherein the alkyl groups, alkenyl groups, cycloalkyl groups, (hetero)aryl groups, alkyl (hetero)aryl groups and (hetero)arylalkyl groups are optionally interrupted by one or more heteroatoms selected from the group consisting of O, S and N.

5. The compound according to claim 1, wherein the compound is according to Formula (12a):

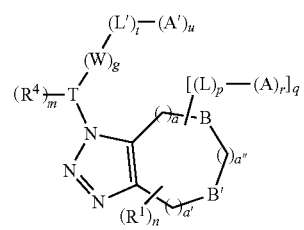

wherein:
a is 1, 2, 3 or 4;
a' is 1, 2, 3 or 4;
a" is 1, 2, 3 or 4;

with the proviso that a+a'+a"=4; and
n is 0-8; or
a is 1, 2, 3,4 or 5;
a' is 1, 2, 3, 4 or 5;
a" is 1, 2, 3, 4 or 5;
with the proviso that a+a'+a"=5; and
n is 0-10;
$R^1$ is independently selected from the group consisting of
—$OR^2$,
—$NO_2$, —CN, —$S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein $R^2$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups;
B and B' are independently selected from the group consisting of O, S, C(O), $NR^3$ and $C(R^3)_2$, wherein $R^3$ is independently selected from the group consisting of hydrogen, $R^1$ or $(L)_p$-$(A)_r$;
optionally, when n is 2 or more, two $R^1$ groups may together form a (hetero)cycloalkyl group, the (hetero)cycloalkyl group optionally being substituted with an $(L)_p$-$(A)_r$ substituent;
optionally, when a" is 2 or more and n is 2 or more, two $R^1$ groups present on adjacent a"-C-atoms may together form a (hetero)aryl group, the (hetero)aryl group optionally being substituted with an $(L)_p$-$(A)_r$ substituent;
p is 0 or 1;
r is 1-4;
L is a linker;
A and A' are independently selected from the group consisting of D, E and Q, wherein D is a molecule of interest, E is a solid surface, and Q is a functional group;
q is 0-4;
with the proviso that if q is 0, then B and/or B' is $NR^3$ wherein $R^3$ is $(L)_p$-$(A)_r$, and/or B and/or B' is $C(R^3)_2$ wherein one or more $R^3$ is $(L)_p$-$(A)_r$, and/or n is 2 or more and two $R^1$ groups together form a (hetero)cycloalkyl group wherein the (hetero)cycloalkyl group is substituted with an $(L)_p$-$(A)_r$ substituent, and/or a" is 2 or more and n is 2 or more and two $R^1$ groups present on adjacent a"-C-atoms together form a (hetero)aryl group wherein the (hetero)aryl group is substituted with an $(L)_p$-$(A)_r$ substituent;
t is 0 or 1;
u is 1-4;
g is 0 or 1;
m is 0-8;
with the proviso that when m is 0, then T is an electron-poor (hetero)aryl group, wherein an electron-poor (hetero)aryl group is:
(a) a (hetero)aryl group wherein the (hetero)aromatic ring system is bearing a positive charge, and/or
(b) a (hetero)aryl group wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring;

L' is a linker;

T is selected from the group consisting of (hetero)aryl groups;

$R^4$ is independently selected from the group consisting of electron-withdrawing substituents having a positive value for the para-Hammett substituent constant $\square_p$ and/or the meta-Hammett substituent constant $\square_m$;

W is selected from the group consisting of $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N; and $R^{15}$ is selected from the group consisting of hydrogen, $C_1$-$C_{24}$ alkyl groups, $C_2$-$C_{24}$ alkenyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkenyl groups, cycloalkyl groups, (hetero)aryl groups, alkyl(hetero)aryl groups and (hetero)arylalkyl groups are optionally substituted, and wherein the alkyl groups, alkenyl groups, cycloalkyl groups, (hetero)aryl groups, alkyl(hetero)aryl groups and (hetero)arylalkyl groups are optionally interrupted by one or more heteroatoms selected from the group consisting of O, S and N.

6. The compound according to claim 1, wherein A and A' are molecules of interest independently selected from the group consisting of a reporter molecule, an active substance, an enzyme, a protein, a glycoprotein, an antibody, a peptide, a polypeptide, an oligonucleotide, a monosaccharide, an oligosaccharide, a polysaccharide, a glycan, an amino acid, a (poly)ethylene glycol diamine, a polyethylene glycol chain, a polyethylene oxide chain, a polypropylene glycol chain, a polypropylene oxide chain and a 1,x-diaminoalkane (wherein x is the number of carbon atoms in the alkane).

7. The compound according to claim 6, wherein A' is a glycoprotein or an, optionally substituted, saccharide moiety.

8. The compound according to claim 1, wherein the compound is according to Formula (13a) or (13d):

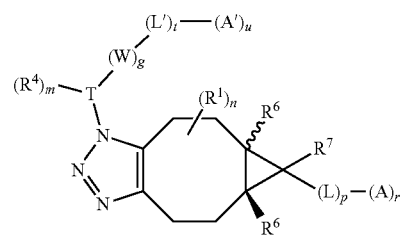

13a

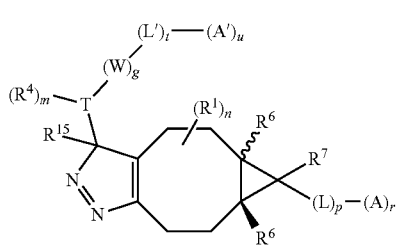

(13d)

wherein:
$R^1$ is independently selected from the group consisting of —$OR^2$, —$NO_2$, —CN, —$S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero) aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein $R^2$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups;

optionally, when n is 2 or more, two $R^1$ groups may together form a (hetero)cycloalkyl group, the (hetero) cycloalkyl group optionally being substituted with an $(L)_p$-$(A)_r$ substituent;

optionally, when a" is 2 or more and n is 2 or more, two $R^1$ groups present on adjacent a"-C-atoms may together form a (hetero)aryl group, the (hetero)aryl group optionally being substituted with an $(L)_p$-$(A)_r$ substituent;

p is 0 or 1;
r is 1-4;
L is a linker;
q is 0-4;
t is 0 or 1;
u is 1-4;
g is 0 or 1;
n is 0-8;
m is 0-8;

with the proviso that when m is 0, then T is an electron-poor (hetero)aryl group, wherein an electron-poor (hetero)aryl group is:
(ii-a) a (hetero)aryl group wherein the (hetero)aromatic ring system is bearing a positive charge, and/or
(ii-b) a (hetero)aryl group wherein the ratio {number π-electrons present in the (hetero)aromatic ring system}:{number of protons present in the nuclei of the (hetero)aromatic ring system} is lower than 0.167 for a 6-membered ring, or lower than 0.200 for a 5-membered ring;

L' is a linker;
A and A' are independently selected from the group consisting of D, E and Q, wherein D is a molecule of interest, E is a solid surface, and Q is a functional;
T is selected from the group consisting of (hetero)aryl groups;
$R^4$ is independently selected from the group consisting of electron-withdrawing substituents having a positive value for the para-Hammett substituent constant $\sigma_p$ and/or the meta-Hammett substituent constant $\sigma_m$;

W is selected from the group consisting of $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N;

$R^6$ is independently selected from the group consisting of hydrogen, halogen, $C_1$-$C_{24}$ alkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkyl(hetero)aryl groups and (hetero)arylalkyl groups optionally are independently optionally interrupted by one of more hetero-atoms selected from the group consisting of O, N and S, and wherein the alkyl groups, (hetero)aryl groups, alkyl(hetero)aryl groups and (hetero)arylalkyl groups are independently optionally substituted;

$R^7$ is selected from the group consisting of hydrogen, $(L)_p$-$(A)_r$, halogen, $C_1$-$C_{24}$ alkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkyl(hetero)aryl groups and (hetero)arylalkyl groups optionally are independently optionally interrupted by one of more hetero-atoms selected from the group consisting of O, N and S, and wherein the alkyl groups, (hetero)aryl groups, alkyl(hetero)aryl groups and (hetero)arylalkyl groups are independently optionally substituted; and $R^{15}$ is selected from the group consisting of hydrogen, $C_1$-$C_{24}$ alkyl groups, $C_2$-$C_{24}$ alkenyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkenyl groups, cycloalkyl groups, (hetero)aryl groups, alkyl(hetero) aryl groups and (hetero)arylalkyl groups are optionally substituted, and wherein the alkyl groups, alkenyl groups, cycloalkyl groups, (hetero)aryl groups, alkyl (hetero)aryl groups and (hetero)arylalkyl groups are optionally interrupted by one or more heteroatoms selected from the group consisting of O, S and N.

9. The compound according to claim 1, wherein the compound is according to Formula (14a) or (14d):

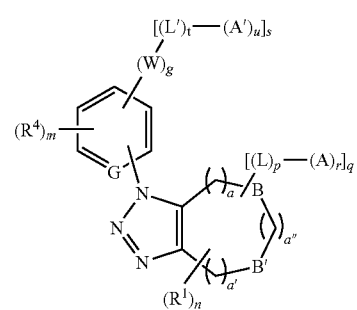

(14a)

-continued

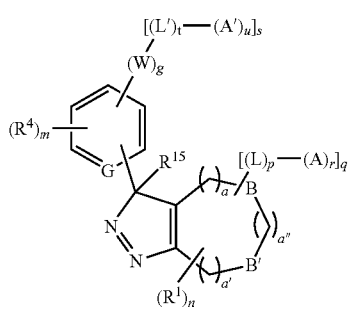

14d wherein:
a' is 1, 2, 3 or 4;
a" is 1, 2, 3 or 4;
with the proviso that a+a'+a"=4; and
n is 0-8; or
when the (hetero)cycloalkyne is a (hetero)cyclononyne:
a is 1, 2, 3, 4 or 5;
a' is 1, 2, 3, 4 or 5;
a" is 1, 2, 3, 4 or 5;
with the proviso that a+a'+a"=5; and
n is 0-10;
$R^1$ is independently selected from the group consisting of —$OR^2$, —$NO_2$, —CN, —$S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein $R^2$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups;
B and B' are independently selected from the group consisting of O, S, C(O), $NR^3$ and $C(R^3)_2$, wherein $R^3$ is independently selected from the group consisting of hydrogen, $R^1$ or $(L)_p$-$(A)_r$;
optionally, when n is 2 or more, two $R^1$ groups may together form a (hetero)cycloalkyl group, the (hetero)cycloalkyl group optionally being substituted with an $(L)_p$-$(A)_r$ substituent;
optionally, when a" is 2 or more and n is 2 or more, two $R^1$ groups present on adjacent a"-C-atoms may together form a (hetero)aryl group, the (hetero)aryl group optionally being substituted with an $(L)_p$-$(A)_r$ substituent;
p is 0 or 1;
r is 1-4;
L is a linker;
q is 0-4;
t is 0 or 1;
u is 1-4;
g is 0 or 1;
m is 0-8;
with the proviso that when m is 0, then T is an electron-poor (hetero)aryl group, wherein an electron-poor (hetero)aryl group is:

(ii-a) a (hetero)aryl group wherein the (hetero)aromatic ring system is bearing a positive charge, and/or
(ii-b) a (hetero)aryl group wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring;
L' is a linker;
A and A' are independently selected from the group consisting of D, E and Q, wherein D is a molecule of interest, E is a solid surface, and Q is a functional;
$R^4$ is independently selected from the group consisting of electron-withdrawing substituents having a positive value for the para-Hammett substituent constant $\sigma_p$ and/or the meta-Hammett substituent constant $\sigma_m$;
W is selected from the group consisting of $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N;
s is 0 or 1;
G is independently selected from the group consisting of N, CH, $CR^4$, $CR^5$, C—$(W)_g$-$[(L')_t$-$(A')_u]$, $N^+R^5$ and $N^+$—$(W)_g$-$[(L')_t$-$(A')_u]$, wherein $R^5$ is selected from the group consisting of $C_1$-$C_{24}$ alkyl groups; and
$R^{15}$ is selected from the group consisting of hydrogen, $C_1$-$C_{24}$ alkyl groups, $C_2$-$C_{24}$ alkenyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkenyl groups, cycloalkyl groups, (hetero)aryl groups, alkyl(hetero)aryl groups and (hetero)arylalkyl groups are optionally substituted, and wherein the alkyl groups, alkenyl groups, cycloalkyl groups, (hetero)aryl groups, alkyl(hetero)aryl groups and (hetero)arylalkyl groups are optionally interrupted by one or more heteroatoms selected from the group consisting of O, S and N.

10. The compound according to claim 1, wherein the compound is according to Formula (12i), (13e) or (14i):

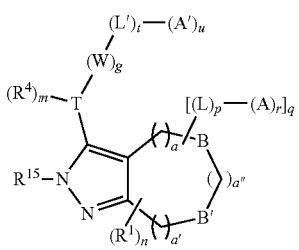

12i

91

-continued

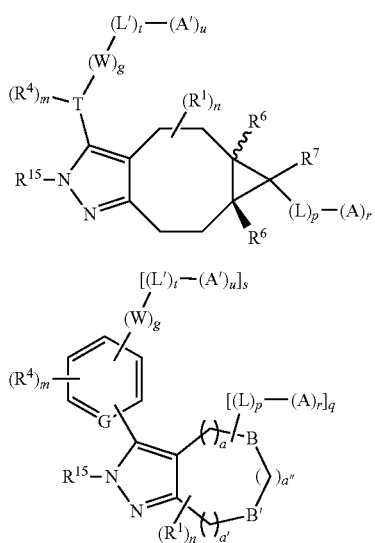

13e

14i wherein:
a' is 1, 2, 3 or 4;
a" is 1, 2, 3 or 4;
with the proviso that a+a'+a"=4; and
n is 0-8; or
when the (hetero)cycloalkyne is a (hetero)cyclononyne:
a is 1, 2, 3, 4 or 5;
a' is 1, 2, 3, 4 or 5;
a" is 1, 2, 3, 4 or 5;
with the proviso that a+a'+a"=5; and
n is 0-10;
$R^1$ is independently selected from the group consisting of —$OR^2$, —$NO_2$, —CN, —$S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein $R^2$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups;
B and B' are independently selected from the group consisting of O, S, C(O), $NR^3$ and $C(R^3)_2$, wherein $R^3$ is independently selected from the group consisting of hydrogen, $R^1$ or $(L)_p$-$(A)_r$;
optionally, when n is 2 or more, two $R^1$ groups may together form a (hetero)cycloalkyl group, the (hetero)cycloalkyl group optionally being substituted with an $(L)_p$-$(A)_r$ substituent;
optionally, when a" is 2 or more and n is 2 or more, two $R^1$ groups present on adjacent a"-C-atoms may together form a (hetero)aryl group, the (hetero)aryl group optionally being substituted with an $(L)_p$-$(A)_r$ substituent;
p is 0 or 1;
r is 1-4;
L is a linker;

92

A and A' are independently selected from the group consisting of D, E and Q, wherein D is a molecule of interest, E is a solid surface, and Q is a functional group;
q is 0-4;
with the proviso that if q is 0, then B and/or B' is $NR^3$ wherein $R^3$ is $(L)_p$-$(A)_r$, and/or B and/or B' is $C(R^3)_2$ wherein one or more $R^3$ is $(L)_p$-$(A)_r$, and/or n is 2 or more and two $R^1$ groups together form a (hetero)cycloalkyl group wherein the (hetero)cycloalkyl group is substituted with an $(L)_p$-$(A)_r$ substituent, and/or a" is 2 or more and n is 2 or more and two $R^1$ groups present on adjacent a"-C-atoms together form a (hetero)aryl group wherein the (hetero)aryl group is substituted with an $(L)_p$-$(A)_r$ substituent;
t is 0 or 1;
u is 1-4;
g is 0 or 1;
m is 0-8;
with the proviso that when m is 0, then T is an electron-poor (hetero)aryl group, wherein an electron-poor (hetero)aryl group is:
(a) a (hetero)aryl group wherein the (hetero)aromatic ring system is bearing a positive charge, and/or
(b) a (hetero)aryl group wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring;
L' is a linker;
T is selected from the group consisting of (hetero)aryl groups;
$R^4$ is independently selected from the group consisting of electron-withdrawing substituents having a positive value for the para-Hammett substituent constant $\sigma_p$ and/or the meta-Hammett substituent constant $\sigma_m$;
W is selected from the group consisting of $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N;
$R^6$ is independently selected from the group consisting of hydrogen, halogen, $C_1$-$C_{24}$ alkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkyl(hetero)aryl groups and (hetero)arylalkyl groups optionally are independently optionally interrupted by one of more hetero-atoms selected from the group consisting of O, N and S, and wherein the alkyl groups, (hetero)aryl groups, alkyl(hetero)aryl groups and (hetero)arylalkyl groups are independently optionally substituted; and
$R^7$ is selected from the group consisting of hydrogen, $(L)_p$-$(A)_r$, halogen, $C_1$-$C_{24}$ alkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkyl(hetero)aryl groups and (hetero)arylalkyl groups optionally are independently optionally interrupted by one of more hetero-atoms selected from the group consisting of O, N and S, and wherein the alkyl groups, (hetero)aryl groups, alkyl(hetero)aryl groups and (hetero)arylalkyl groups are independently optionally substituted; and $R^{15}$ is H.

11. A process for preparing a compound according to claim 1 comprising reacting a (hetero)aryl 1,3-dipole compound with a (hetero)cycloalkyne, wherein:
the (hetero)aryl 1,3-dipole compound is defined as a compound comprising a 1,3-dipole functional group, wherein the 1,3-dipole functional group is bonded to a (hetero)aryl group, and wherein the (hetero)aryl 1,3-dipole compound is a (hetero)aryl azide or a (hetero)aryl diazo compound; wherein:
(i) the (hetero)aryl group of the (hetero)aryl 1,3-dipole compound comprises one or more substituents having a positive value for the para-Hammett substituent constant $\sigma_p$ and/or the meta-Hammett substituent constant am, and/or
(ii) the (hetero)aryl group of the (hetero)aryl 1,3-dipole compound is an electron-poor (hetero)aryl group, wherein an electron-poor (hetero)aryl group is:
(ii-a) a (hetero)aryl group wherein the (hetero)aromatic ring system is bearing a positive charge, and/or
(ii-b) a (hetero)aryl group wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring;
the (hetero)cycloalkyne is an aliphatic (hetero)cycloalkyne, wherein an aliphatic (hetero)cycloalkyne is defined as a (hetero)cycloalkyne wherein both $sp^1$ C-atoms of the (hetero)cycloalkyne carbon-carbon triple bond are bonded to an $sp^3$ C-atom;
wherein the (hetero)cycloalkyne is a (hetero)cyclooctyne or a (hetero)cyclononyne according to Formula (1):

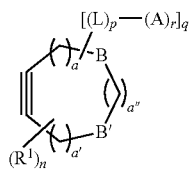

wherein:
when the (hetero)cycloalkyne is a (hetero)cyclooctyne: a is 1, 2, 3 or 4;
a' is 1, 2, 3 or 4;
a" is 1, 2, 3 or 4;
with the proviso that a+a'+a"=4; and
n is 0-8; or
when the (hetero)cycloalkyne is a (hetero)cyclononyne:
a is 1, 2, 3, 4 or 5;
a' is 1, 2, 3, 4 or 5;
a" is 1, 2, 3, 4 or 5;
with the proviso that a+a'+a"=5; and
n is 0-10;
$R^1$ is independently selected from the group consisting of —$OR^2$, —$NO_2$, —CN, —$S(O)_2R^2$, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted, wherein the alkyl groups, cycloalkyl groups, alkyl (hetero)aryl groups and (hetero)arylalkyl groups are optionally interrupted by one or more heteroatoms selected from the group consisting of O, S and N, and wherein $R^2$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups;
B and B' are independently selected from the group consisting of O, S, C(O), $NR^3$ and $C(R^3)_2$, wherein $R^3$ is independently selected from the group consisting of hydrogen, $R^1$ or $(L)_p$-$(A)_r$;
optionally, when n is 2 or more, two $R^1$ groups may together form a (hetero)cycloalkyl group, the (hetero)cycloalkyl group optionally being substituted with an $(L)_p$-$(A)_r$ substituent;
optionally, when a" is 2 or more and n is 2 or more, two $R^1$ groups present on adjacent a"-C-atoms may together form a (hetero)aryl group, the (hetero)aryl group optionally being substituted with an $(L)_p$-$(A)_r$ substituent;
p is 0 or 1,
r is 1-4;
L is a linker;
A is independently selected from the group consisting of D, E and Q, wherein D, E and Q are as defined below;
q is 0-4;
with the proviso that if q is 0, then B and/or B' is $NR^3$ wherein $R^3$ is $(L)_p$-$(A)_r$, and/or B and/or B' is $C(R^3)_2$ wherein one or more $R^3$ is $(L)_p$-$(A)_r$, and/or n is 2 or more and two $R^1$ groups together form a (hetero)cycloalkyl group wherein the (hetero)cycloalkyl group is substituted with an $(L)_p$-$(A)_r$ substituent, and/or a" is 2 or more and n is 2 or more and two $R^1$ groups present on adjacent a"-C-atoms together form a (hetero)aryl group wherein the (hetero)aryl group is substituted with an $(L)_p$-$(A)_r$ substituent;
D is a molecule of interest;
E is a solid surface; and
Q is a functional group.

12. The process according to claim 11, wherein the molecule of interest is selected from the group consisting of a reporter molecule, a diagnostic compound, an active substance, an enzyme, an amino acid, a (non-catalytic) protein, a peptide, a polypeptide, an oligonucleotide, a monosaccharide, an oligosaccharide, a polysaccharide, a glycan, a (poly)ethylene glycol diamine, a polyethylene glycol chain, a polyethylene oxide chain, a polypropylene glycol chain, a polypropylene oxide chain and a 1,x-diaminoalkane, wherein x is the number of carbon atoms in the alkane.

13. The process according to claim 11, wherein the solid surface is selected from the group consisting of a functional surface, a nanomaterial, a carbon nanotube, a fullerene, a virus capsid, a metal surface, a metal alloy surface and a polymer surface.

14. The process according to claim 11, wherein Q is selected from the groups consisting of hydrogen, halogen, $R^{11}$, —CH=C($R^{11}$)$_2$, —C≡C$R^{11}$, —[C($R^{11}$)$_2$C($R^{11}$)$_2$O]$_q$—$R^{11}$ wherein q is in the range of 1 to 200, —CN, —N$_3$, —NCX, —XCN, —X$R^{11}$, —N($R^{11}$)$_2$, —$^+$N($R^{11}$)$_3$, —C(X)N($R^{11}$)$_2$, —C($R^{11}$)$_2$X$R^{11}$, —C(X)$R^{11}$, —C(X)X$R^{11}$, —S(O)$R^{11}$, —S(O)$_2$$R^{11}$, —S(O)O$R^{11}$, —S(O)$_2$O$R^{11}$, —S(O)N($R^{11}$)$_2$, —S(O)$_2$N($R^{11}$)$_2$, —OS(O)$R^{11}$, —OS(O)$_2$$R^{11}$, —OS(O)O$R^{11}$, —OS(O)$_2$O$R^{11}$, —P(O)($R^{11}$)(O$R^{11}$), —P(O)(O$R^{11}$)$_2$, —OP(O)(O$R^{11}$)$_2$, —Si($R^{11}$)$_3$, —XC(X)$R^{11}$, —XC(X)X$R^{11}$, —XC(X)N($R^{11}$)$_2$, —N($R^{11}$)C(X)$R^{11}$, —N($R^{11}$)C(X)X$R^{11}$ and —N($R^{11}$)C(X)N($R^{11}$)$_2$, wherein X is oxygen or sulphur and wherein $R^{11}$ is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O and N.

15. The process according to claim 11, wherein the (hetero)aryl 1,3-dipole compound is according to Formula (2):

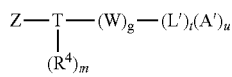

wherein:
t is 0 or 1;
u is 1-4;
g is 0 or 1;
m is 0-8;
with the proviso that when m is 0, then T is an electron-poor (hetero)aryl group, wherein an electron-poor (hetero)aryl group is:
  (ii-a) a (hetero)aryl group wherein the (hetero)aromatic ring system is bearing a positive charge, and/or
  (ii-b) a (hetero)aryl group wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring;
Z is an azide functional group or a diazo functional group;
L' is a linker;
A' is independently selected from the group consisting of D, E and Q, wherein D is a molecule of interest, E is a solid surface, and Q is a functional group;
T is selected from the group consisting of (hetero)aryl groups;
$R^4$ is independently selected from the group consisting of electron-withdrawing substituents having a positive value for the para-Hammett substituent constant σ$_p$ and/or the meta-Hammett substituent constant σ$_m$; and
W is selected from the group consisting of $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N.

16. The process according to claim 11, wherein T is selected from the group consisting of phenyl groups, pyridinyl groups, pyridiniumyl groups, pyrimidinyl groups, pyrimidinium groups, pyrazinyl groups, pyradizinyl groups, pyrrolyl groups, pyrrolium groups, furanyl groups, thiophenyl groups, diazolyl groups, quinolinyl groups, imidazolyl groups, oxazolyl groups and oxazolium groups, said groups optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, amino groups and silyl groups, wherein the silyl groups can be represented by the formula ($R^{Si}$)$_3$Si—, wherein $R^{Si}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S.

17. The process according to claim 11, wherein the (hetero)aryl 1,3-dipole compound is according to Formula (3a), (3b), (3c), (3d), (3e) or (3f):

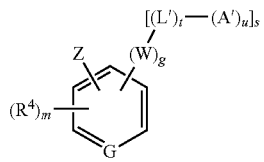

3a

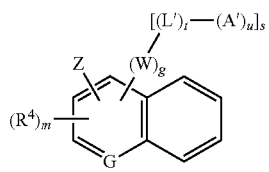

3b

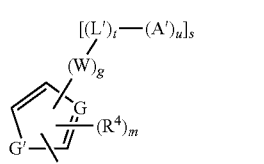

3c

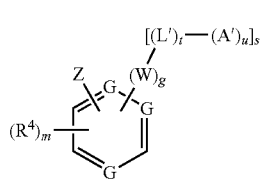

3d

97

-continued

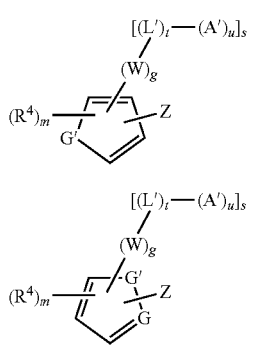

3e

3f wherein:
s is 0 or 1;
t is 0 or 1;
u is 1-4;
g is 0 or 1;
m is 0-8;
with the proviso that when m is 0, then T is an electron-poor (hetero)aryl group, wherein an electron-poor (hetero)aryl group is:
  (ii-a) a (hetero)aryl group wherein the (hetero)aromatic ring system is bearing a positive charge, and/or
  (ii-b) a (hetero)aryl group wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring;
Z is an azide functional group or a diazo functional group;
L' is a linker;
A' is independently selected from the group consisting of D, E and Q, wherein D is a molecule of interest, E is a solid surface, and Q is a functional;
$R^4$ is independently selected from the group consisting of electron-withdrawing substituents having a positive value for the para-Hammett substituent constant $\sigma_p$ and/or the meta-Hammett substituent constant $\sigma_m$;
W is selected from the group consisting of $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N;
G is independently selected from the group consisting of N, CH, $CR^4$, $CR^5$, C—$(W)_g$-[(L')$_t$-(A')$_u$],
$N^+R^5$ and $N^+$—$(W)_g$-[(L')$_t$-(A')$_u$], wherein $R^5$ is selected from the group consisting of $C_1$-$C_{24}$ alkyl groups;
G' is independently selected from the group consisting of O, S, $NR^{12}$, and $N^+(R^{12})_2$ wherein $R^{12}$ is independently selected from the group consisting of hydrogen, $R^4$, $R^5$ and $(W)_g$-[(L')$_t$-(A')$_u$]; and
with the proviso that when s is 0, G is C—$(W)_g$-[(L')$_t$-(A')$_u$] or $N^+$-$(W)_g$-[(L')$_t$-(A')$_u$], and G' is N-$(W)_g$-[(L')$_t$-(A')$_u$] or $N^+(R^{12})$ {-$(W)_g$-[(L')$_t$-(A')$_u$]}.

98

18. The process according to claim 11, wherein the (hetero)aryl 1,3-dipole compound is according to Formula (3za), (3zb), (3zc), (3zd), (3ze), (3zf) or (3zg):

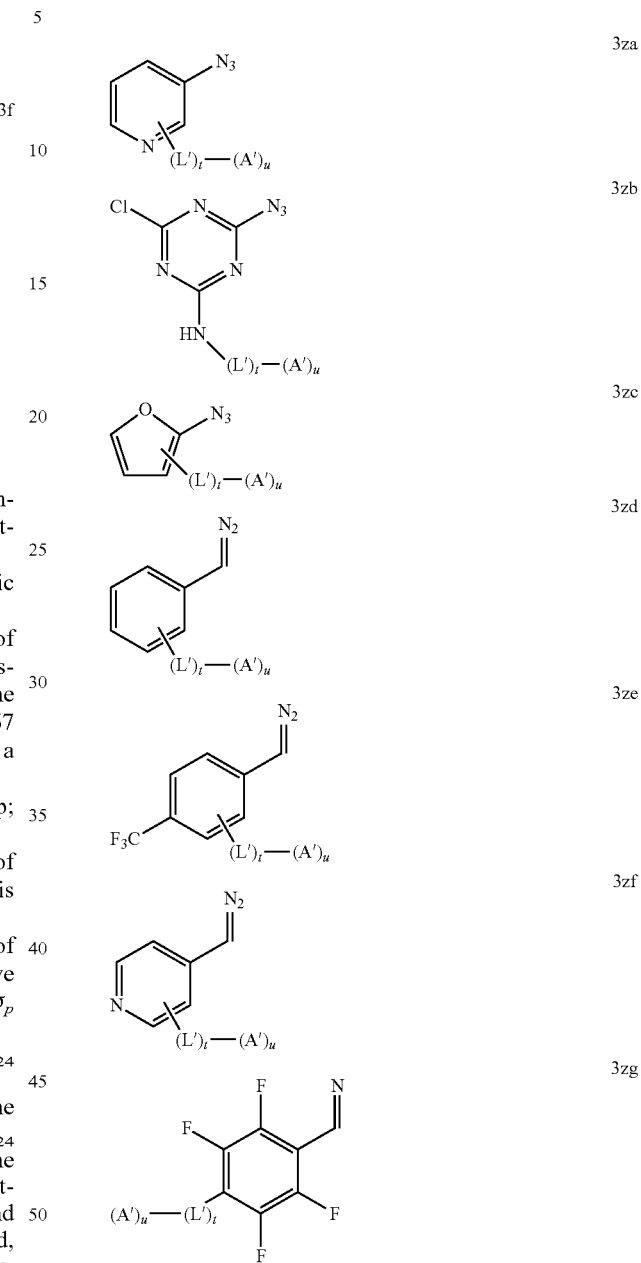

wherein:
t is 0 or 1;
u is 1-4;
L' is a linker; and
A' is independently selected from the group consisting of D, E and Q, wherein D is a molecule of interest, E is a solid surface, and Q is a functional.

19. The process according to claim 11, wherein A' is a glycoprotein or an, optionally substituted, saccharide moiety.

20. The process according to claim 19, wherein the (hetero)aryl 1,3-dipole compound is according to Formula (2b) or (2c):

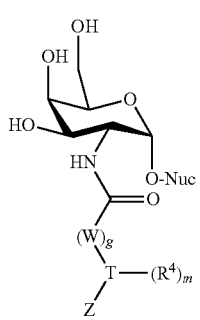

2b

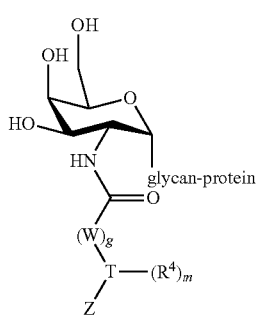

2c wherein:
g is 0 or 1;
m is 0-8;
with the proviso that when m is 0, then T is an electron-poor (hetero)aryl group, wherein an electron-poor (hetero)aryl group is:
  (ii-a) a (hetero)aryl group wherein the (hetero)aromatic ring system is bearing a positive charge, and/or
  (ii-b) a (hetero)aryl group wherein the ratio {number of π-electrons present in the (hetero)aromatic ring system}:{number of protons present in the nuclei of the (hetero)aromatic ring system} is lower than 0.167 for a 6-membered ring, or lower than 0.200 for a 5-membered ring;
Z is an azide functional group or a diazo functional group;
T is selected from the group consisting of (hetero)aryl groups;
$R^4$ is independently selected from the group consisting of electron-withdrawing substituents having a positive value for the para-Hammett substituent constant $\sigma_p$ and/or the meta-Hammett substituent constant $\sigma_m$;
W is selected from the group consisting of $C_1$-$C_{24}$ alkylene groups, $C_2$-$C_{24}$ alkenylene groups, $C_3$-$C_{24}$ cycloalkylene groups, $C_2$-$C_{24}$ (hetero)arylene groups, $C_3$-$C_{24}$ alkyl(hetero)arylene groups and $C_3$-$C_{24}$ (hetero)arylalkylene groups, wherein the alkylene groups, alkenylene groups, cycloalkylene groups, (hetero)arylene groups, alkyl(hetero)arylene groups and (hetero)arylalkylene groups are optionally substituted, and wherein the alkylene groups, alkenylene groups, cycloalkylene groups, (hetero)arylene groups, alkyl(hetero)arylene groups and (hetero)arylalkylene groups are optionally interrupted by one or more heteroatoms selected from the group consisting of O, S and N; and
Nuc is a nucleotide.

21. The process according to claim 19, wherein the (hetero)aryl 1,3-dipole compound is according to Formula (2d), (2e), (2f) or (2g):

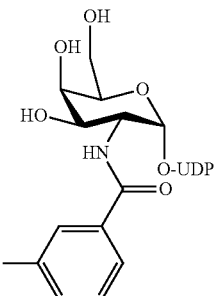

2d

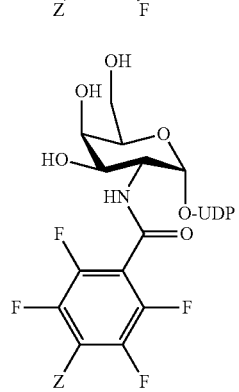

2e

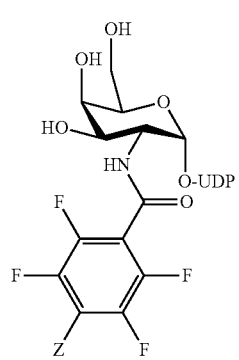

2f

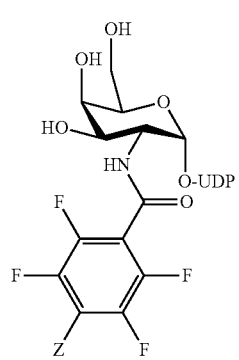

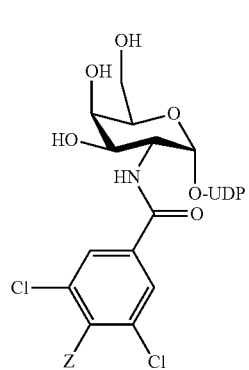

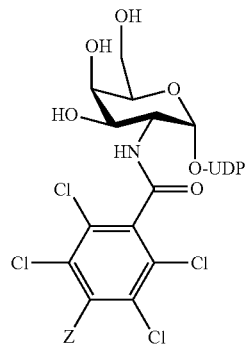

2g wherein Z is an azide group or a diazo group.

22. The process according to claim 11, wherein the (hetero)aryl 1,3-dipole compound is a (hetero)aryl azide.

23. The process according to claim 11, wherein the (hetero)cycloalkyne is a (hetero)cyclooctyne.

24. The process according to claim 23, wherein the (hetero)cyclooctyne is according to Formula (5):

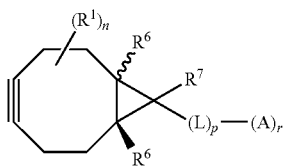

5 wherein:
is independently selected from the group consisting of —OR², —NO₂, —CN, —S(O)₂R², $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, cycloalkyl groups, (hetero)aryl groups, alkyl(hetero)aryl groups and (hetero)arylalkyl groups are optionally substituted, wherein the alkyl groups, cycloalkyl groups, alkyl(hetero)aryl groups and (hetero)arylalkyl groups are optionally interrupted by one or more heteroatoms selected from the group consisting of O, S and N, and wherein R² is independently selected from the group consisting of hydrogen, halogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups;
optionally, when n is 2 or more, two $R^1$ groups may together form a (hetero)cycloalkyl group, the (hetero)cycloalkyl group optionally being substituted with an $(L)_p$-$(A)_r$ substituent;
optionally, when a" is 2 or more and n is 2 or more, two $R^1$ groups present on adjacent a"-C-atoms may together form a (hetero)aryl group, the (hetero)aryl group optionally being substituted with an $(L)_p$-$(A)_r$ substituent;
p is 0 or 1;
r is 1-4;
L is a linker;
A is independently selected from the group consisting of D, E and Q, wherein D is a molecule of interest, E is a solid surface, and Q is a functional group;
n is 0-8;
$R^6$ is independently selected from the group consisting of hydrogen, halogen, $C_1$-$C_{24}$ alkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkyl(hetero)aryl groups and (hetero)arylalkyl groups optionally are independently optionally interrupted by one of more hetero-atoms selected from the group consisting of O, N and S, and wherein the alkyl groups, (hetero)aryl groups, alkyl(hetero)aryl groups and (hetero)arylalkyl groups are independently optionally substituted; and
$R^7$ is selected from the group consisting of hydrogen, $(L)_p$-$(A)_r$, halogen, $C_1$-$C_{24}$ alkyl groups, $C_2$-$C_{24}$ (hetero)aryl groups, $C_3$-$C_{24}$ alkyl(hetero)aryl groups and $C_3$-$C_{24}$ (hetero)arylalkyl groups, wherein the alkyl groups, alkyl(hetero)aryl groups and (hetero)arylalkyl groups optionally are independently optionally interrupted by one of more hetero-atoms selected from the group consisting of O, N and S, and wherein the alkyl groups, (hetero)aryl groups, alkyl(hetero)aryl groups and (hetero)arylalkyl groups are independently optionally substituted.

25. The process according to claim 24, wherein n is 0, $R^6$ is H, $R^7$ is H and p is 1.

26. The process according to claim 23, wherein the (hetero)cyclooctyne is according to Formula (7), (8), (9), (10) or (11):

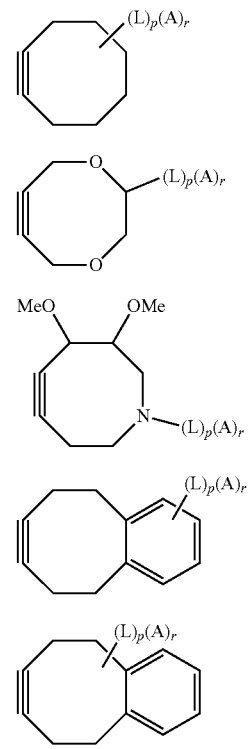

wherein:
p is 0 or 1;
r is 1-4;
L is a linker; and
A is independently selected from the group consisting of D, E and Q, wherein D is a molecule of interest, E is a solid surface, and Q is a functional group.

27. The process according to claim 11, wherein the (hetero)cycloalkyne is a (hetero)cyclononyne according to Formula (35a) or (35b):

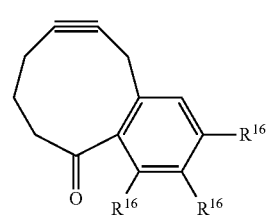

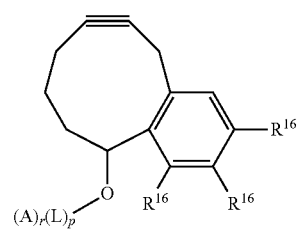

wherein:
is 0 or 1;
r is 1-4;
L is a linker;

A is independently selected from the group consisting of D, E and Q, wherein D is a molecule of interest, E is a solid surface, and Q is a functional group; and $R^{16}$ is $-(L)_p(A)_r$, H or —OMe.

28. The process according to claim 11, wherein A and A' are molecules of interest independently selected from the group consisting of a reporter molecule, an active substance, an enzyme, a protein, a glycoprotein, an antibody, a peptide, a polypeptide, an oligonucleotide, a monosaccharide, an oligosaccharide, a polysaccharide, a glycan, an amino acid, a (poly)ethylene glycol diamine, a polyethylene glycol chain, a polyethylene oxide chain, a polypropylene glycol chain, a polypropylene oxide chain and a 1,x-diaminoalkane (wherein x is the number of carbon atoms in the alkane).

\* \* \* \* \*